(12) United States Patent
Bresnick

(10) Patent No.: US 11,596,441 B2
(45) Date of Patent: Mar. 7, 2023

(54) BIOFILM PROTECTION IMPLANT SHIELD

(71) Applicant: Stephen David Bresnick, Encino, CA (US)

(72) Inventor: Stephen David Bresnick, Encino, CA (US)

( * ) Notice: Subject to any disclaimer, the term of this patent is extended or adjusted under 35 U.S.C. 154(b) by 0 days.

(21) Appl. No.: 17/135,242

(22) Filed: Dec. 28, 2020

(65) Prior Publication Data

US 2021/0137557 A1 May 13, 2021

Related U.S. Application Data

(63) Continuation of application No. 16/709,785, filed on Dec. 10, 2019, now Pat. No. 10,874,430.

(60) Provisional application No. 62/847,151, filed on May 13, 2019.

(51) Int. Cl.
  *A61F 2/12* (2006.01)
  *A61B 17/34* (2006.01)
  *A61L 27/54* (2006.01)

(52) U.S. Cl.
  CPC .......... *A61B 17/3468* (2013.01); *A61F 2/12* (2013.01); *A61L 27/54* (2013.01); *A61F 2230/0067* (2013.01); *A61F 2250/0003* (2013.01)

(58) Field of Classification Search
  CPC ... A61F 2/12; A61B 17/3468; A61B 17/3423; A61B 17/02; A61B 2017/3492; A61B 19/08; A61B 2017/00792; A61B 2017/00796; A61B 17/0293; A61B 17/3421; A61B 2017/00287
  See application file for complete search history.

(56) References Cited

U.S. PATENT DOCUMENTS

| | | | | |
|---|---|---|---|---|
| 4,035,850 A | * | 7/1977 | Cresswall | A61F 2/12 606/1 |
| 4,188,945 A | * | 2/1980 | Wenander | A61B 46/00 128/850 |
| 4,641,648 A | * | 2/1987 | Shapiro | A61B 90/00 623/7 |
| 4,754,750 A | * | 7/1988 | Imonti | A61F 15/008 D24/189 |
| 4,790,309 A | * | 12/1988 | Becker | A61F 2/12 606/1 |

(Continued)

FOREIGN PATENT DOCUMENTS

WO    2018199929 A1    11/2018

*Primary Examiner* — Seema Mathew
(74) *Attorney, Agent, or Firm* — Womble Bond Dickinson (US) LLP

(57) ABSTRACT

Apparatus, systems, and methods for inserting prosthesis implants into surgically-created implant pockets in a subject and for preventing capsular contracture resulting from surgical insertion of prosthesis implants. The apparatus includes a base having an upper surface and a lower surface and having an aperture formed therein which extends through the upper surface and the lower surface of the base. The apparatus also includes a tubular member that is coupled to the base. The inner bore of the tubular member is operable to receive the implant and has a substantially uniform cross-sectional width over the predetermined length. The apparatus is capable of shielding the implant from microbial contamination, including contamination by the endogenous flora of the subject, during insertion of the implant into the surgically-created implant pocket.

30 Claims, 20 Drawing Sheets

(56) References Cited

U.S. PATENT DOCUMENTS

| | | | |
|---|---|---|---|
| 4,998,538 A * | 3/1991 | Charowsky | A61B 90/40 128/917 |
| 5,522,791 A * | 6/1996 | Leyva | A61B 17/0293 600/207 |
| 5,649,550 A * | 7/1997 | Crook | A61B 46/00 128/853 |
| 5,741,298 A * | 4/1998 | MacLeod | A61B 42/10 604/338 |
| 5,947,922 A * | 9/1999 | MacLeod | A61B 17/00234 604/35 |
| 6,122,542 A * | 9/2000 | Lee | A61B 90/17 128/915 |
| 6,146,418 A | 11/2000 | Berman | |
| 6,589,211 B1 * | 7/2003 | MacLeod | A61B 42/10 604/164.06 |
| 6,814,700 B1 * | 11/2004 | Mueller | A61B 17/0293 600/206 |
| 8,206,443 B2 | 6/2012 | Preissman | |
| 8,211,173 B2 | 7/2012 | Keller et al. | |
| 8,315,700 B2 | 11/2012 | Citron et al. | |
| 8,409,279 B2 | 4/2013 | Freund | |
| 8,550,090 B2 | 10/2013 | Keller et al. | |
| 8,555,893 B2 | 10/2013 | Keller et al. | |
| 8,641,758 B1 * | 2/2014 | Anderson | A61F 2/12 623/7 |
| 9,055,907 B2 * | 6/2015 | Piech | A61B 1/32 |
| 9,168,126 B2 | 10/2015 | Preissman | |
| 9,402,713 B2 | 8/2016 | Keller et al. | |
| 9,414,941 B2 | 8/2016 | Placik et al. | |
| 9,474,545 B1 * | 10/2016 | Kim | A61B 42/10 |
| 9,549,758 B2 * | 1/2017 | Smith | A61B 17/3423 |
| 9,737,395 B2 | 8/2017 | Nguyen et al. | |
| 9,808,284 B2 | 11/2017 | Anderson | |
| 9,808,285 B2 | 11/2017 | Anderson | |
| 10,004,534 B2 | 6/2018 | Anderson | |
| 10,022,475 B2 | 7/2018 | Nguyen et al. | |
| 10,058,415 B2 | 8/2018 | Preissman | |
| 10,092,385 B2 | 10/2018 | Anderson | |
| 10,105,213 B2 | 10/2018 | Weinzweig | |
| 10,136,988 B2 | 11/2018 | Keller et al. | |
| 10,213,294 B2 | 2/2019 | Keller et al. | |
| 11,160,682 B2 * | 11/2021 | Aravalli | A61B 17/3415 |
| 2005/0021058 A1 * | 1/2005 | Negro | A61F 2/0063 606/151 |
| 2007/0276484 A1 | 11/2007 | Abell et al. | |
| 2010/0154803 A1 * | 6/2010 | Haworth | A61B 46/00 128/856 |
| 2011/0257665 A1 * | 10/2011 | Mortarino | A61L 27/3604 606/151 |
| 2012/0157782 A1 * | 6/2012 | Altieri | A61B 17/3423 600/206 |
| 2014/0228951 A1 * | 8/2014 | Zochowski | A61F 2/12 623/8 |
| 2015/0053747 A1 * | 2/2015 | Prior | A61B 46/13 227/179.1 |
| 2015/0297339 A1 * | 10/2015 | Placik | A61F 2/0095 623/8 |
| 2016/0166322 A1 * | 6/2016 | Lowrance | A61B 46/10 128/853 |
| 2016/0287240 A1 * | 10/2016 | Suh | A61B 17/0218 |
| 2016/0374720 A1 * | 12/2016 | Anderson | A61F 2/0095 623/8 |
| 2019/0274818 A1 * | 9/2019 | Hristov | A61B 17/3468 |
| 2020/0282761 A1 * | 9/2020 | Hsu | B43K 8/003 |
| 2022/0160491 A1 * | 5/2022 | Zemmel | A61F 2/12 |

* cited by examiner

BIOFILM PROTECTION IMPLANT SHIELD

CROSS-REFERENCE TO RELATED APPLICATIONS

This application is a continuation of U.S. application Ser. No. 16/709,785, entitled "Biofilm Protection Implant Shield," filed Dec. 10, 2019, which claims the benefit of U.S. Provisional Application Ser. No. 62/847,151, entitled "Biofilm Protection Implant Shield," filed May 13, 2019, the contents of each of which are incorporated by reference herein, for all purposes, in their entirety.

FIELD OF TECHNOLOGY

The present disclosure is directed to the insertion of prosthesis implants into a surgically-created implant pocket of a subject. In some specific instances, the present disclosure is directed to the insertion of breast implants, including un-filled implants and pre-filled implants such as silicone breast implants and pre-filled saline implants. The present disclosure is further directed to methods, devices, and systems for inserting prosthesis implants in the surgically-created implant pocket of a subject as well as methods for preventing capsular contracture resulting from surgical insertion of prosthesis implants.

BACKGROUND

Capsular contracture remains the most common complication of aesthetic breast augmentation despite advances in the understanding of the biological processes which appear to be involved. Capsular contracture is characterized by the tightening and hardening of the capsule surrounding the implant. The role of biofilms in capsular contracture has been reported extensively and is believed to play an important role in the pathogenesis of capsular contracture. Recent advances in antibiotic irrigation as well as the use of skin barriers and nipple shields has assisted in the reduction of capsular contracture. Yet, despite these advances, a significant number of women develop capsular contracture following breast augmentation and require revisional surgery or live with discomfort, deformity, or suboptimal results.

Form-stable implant studies with textured devices have shown lower capsular contracture rates compared to smooth round devices. However, anaplastic large cell lymphoma (ALCL) is an indolent lymphoma found in women with textured implants. Biofilm infection is hypothesized to be involved in the development of both capsular contracture and ALCL. It is suspected that a source of the biofilm infection may be microbes from the skin and/or exposed breast tissue of the patient that come in contact with the sterile implant during insertion into the surgically-created implant pocket. In particular, the subject's endogenous flora present at the time of the surgery, including those bacteria that may be present in the dissection tunnel connecting the skin incision to the surgically-created implant pocket or the skin surface itself, may attach to the surface of the implant during placement in the implant pocket. Following insertion of the implant, the bacteria may colonize the surface of the implant and form a biofilm. If the surface of the implant is colonized by a large number of bacteria, the subject's defenses may be overwhelmed and the biofilm may trigger a chronic inflammatory response leading to subsequent fibrosis and accelerated capsular contracture. Accordingly, methods and devices capable of shielding the implant from microbial contamination, including contamination by the endogenous flora of the subject, during insertion of the implant into the surgically-created implant pocket are desirable.

BRIEF DESCRIPTION OF THE DRAWINGS

In order to describe the manner in which the advantages and features of the disclosure can be obtained, reference is made to embodiments thereof which are illustrated in the appended drawings. One of skill in the art will understand that the reference numbers in the following figures are repeated throughout FIGS. 1-32 so as to refer to the same or substantially the same features. Understanding that these drawings depict only exemplary embodiments of the disclosure and are not therefore to be considered to be limiting of its scope, the principles herein are described and explained with additional specificity and detail through the use of the accompanying drawings in which.

DETAILED DESCRIPTION

Figure 1:
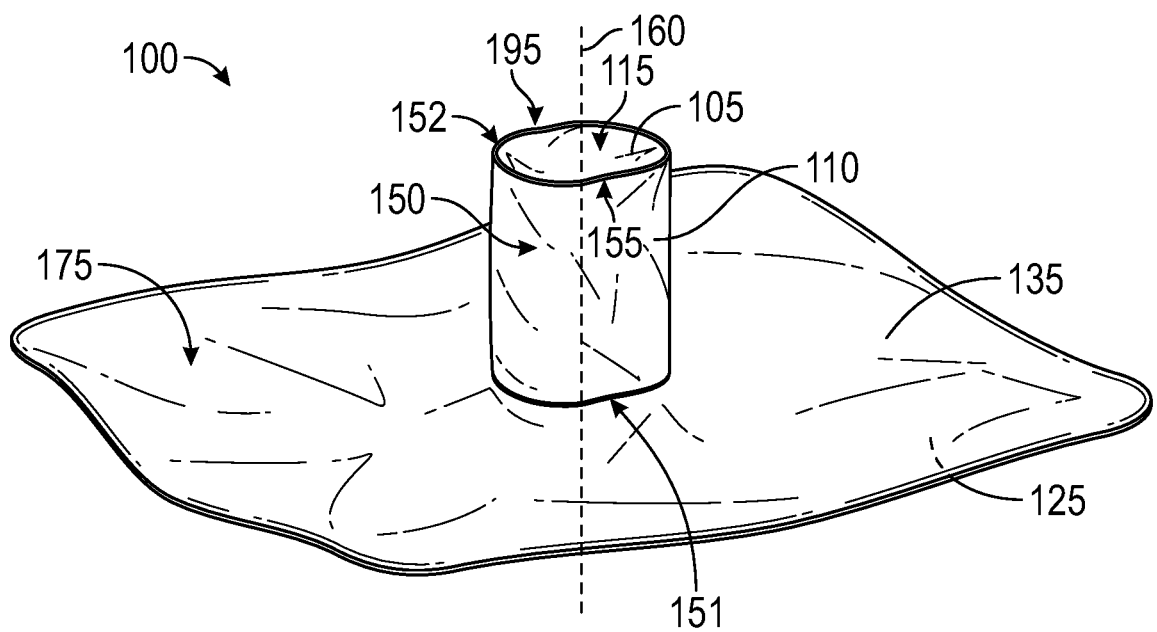
FIG. 1 is an isometric view of the implant shield apparatus, according to an exemplary embodiment of the present disclosure.

It will be appreciated that numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. Also, the description is not to be considered as limiting the scope of the embodiments described herein.

The present disclosure provides apparatus, methods, and systems for inserting prosthesis implants into surgically-created implant pockets in a subject. The presently disclosed apparatus, methods, and systems may be used to deliver any prosthesis implant into a surgically-created implant pocket in a subject. The present disclosure is further directed to methods, devices, and systems for preventing capsular contracture resulting from surgical insertion of prosthesis implants. The prosthesis implant may include, for example, filled implants or pre-filled implants, unfilled implants, saline implants, silicone gel implants, textured implants, smooth implants, highly cohesive silicone gel implants, or oil-filled implants. The prosthesis implant may also be, for example, an implantable device, such as a pacemaker or a joint replacement prosthesis, or the prosthesis implant may be a tissue graft, such as an allograft or an autograft.

In some specific instances, the present disclosure is directed to the insertion of breast implants into the implant pocket in a breast of a subject. In such cases, the breast implant may be an un-filled breast implant or may be a pre-filled breast implant such as a pre-filled saline implant or a pre-filled silicone implant. In particular, the presently disclosed apparatus, methods, and systems are well-suited to the delivery of pre-filled breast implants which require an insertion device capable of withstanding and managing the compressive and frictional forces associated with insertion of the pre-filled implant while still being gentle enough so as to not damage the pre-filled implant during delivery to the implant pocket in the subject. The breast implant may also be, for example, a textured breast implant, a smooth breast implant, a highly cohesive silicone gel breast implant, an oil-filled breast implant, or an un-filled saline breast implant. The present disclosure is further directed to methods, devices, and systems for preventing capsular contracture resulting from surgical insertion of breast implants.

According to at least one aspect of the present disclosure, an apparatus for inserting an implant into a surgically-created implant pocket in a subject is provided. The apparatus may include a base having an upper surface and a lower surface. The base may have an aperture formed therein which extends through the upper surface and the lower surface of the base. The apparatus may also include a tubular member that is coupled to the base. The tubular member may have an inner bore extending longitudinally between a proximal end and a distal end. The inner bore may extend a predetermined length away from the lower surface of the base. The proximal end of the tubular member may be coupled with the base and the inner bore may be substantially aligned with the aperture formed in the base. The inner bore of the tubular member may be operable to receive the implant and has a substantially uniform cross-sectional width over the predetermined length.

According to another aspect of the present disclosure, an apparatus for inserting an implant into a surgically-created implant pocket in a subject is provided. The apparatus includes a base having an upper surface and a lower surface. The apparatus also includes a tubular member extending through the base. The tubular member has an inner bore, a proximal end and a distal end. The inner bore of the tubular member extends longitudinally a predetermined length away from the lower surface of the base and between the proximal end and the distal end. The inner bore is operable to receive an implant therethrough and has a substantially uniform cross-sectional width over the predetermined length.

The presently disclosed apparatus may also be used to prevent capsular contracture in a subject resulting from surgical insertion of a breast implant in a surgically-created implant pocket through a dissection tunnel connecting the implant pocket to an incision on the skin of the subject. The apparatus is capable of shielding the implant from microbial contamination, including contamination by the endogenous flora of the subject, during insertion of the implant into the surgically-created implant pocket.

According to at least one aspect of the present disclosure, a system is provided. The system includes an apparatus for inserting an implant into a surgically-created implant pocket in a subject as described herein. The system further includes an implant that may be inserted by the apparatus.

According to at least one other aspect of the present disclosure, a system is provided. The system includes an apparatus for inserting an implant into a surgically-created implant pocket in a subject as described herein. The system further includes a conical sleeve having an interior cavity, a first terminus, and a second terminus. The first terminus of the conical sleeve has a larger diameter than the second terminus. The second terminus is operable to be inserted into the aperture of the base or inner bore of the tubular member of the apparatus. The conical sleeve is further operable to receive an implant into its interior cavity via the first terminus and deliver the implant through the second terminus into the aperture of the base or the inner bore of the tubular member of the apparatus. In at least some instances, the system further includes an implant that may be inserted by the conical sleeve.

According to at least one aspect of the present disclosure, a kit is provided. The kit includes an apparatus for inserting an implant into a surgically-created implant pocket in a subject, as described herein. Packaged together with the apparatus, the kit further includes an implant that may be inserted by the apparatus.

According to at least one other aspect of the present disclosure, a kit is provided. The kit includes an apparatus for inserting an implant into a surgically-created implant pocket in a subject as described herein. The kit further includes a conical sleeve packaged together with the apparatus. The conical sleeve has an interior cavity, a first terminus, and a second terminus. The first terminus of the conical sleeve has a larger diameter than the second terminus. The second terminus is operable to be inserted into the aperture of the base or the inner bore of the tubular member of the apparatus. The conical sleeve is further operable to receive an implant into its interior cavity via the first terminus and deliver the implant through the second terminus into the aperture of the base or the inner bore of the tubular member of the apparatus. In at least some instances, the kit further includes an implant packaged together with the apparatus and the conical sleeve. The implant is capable of being inserted by the conical sleeve.

According to at least one aspect of the present disclosure, a method for inserting an implant into a surgically-created implant pocket in a subject through a dissection tunnel connecting the implant pocket to an incision on the skin of the subject is disclosed. The method may include providing a sterile biofilm protection implant shield. The implant shield may include a base having an upper surface and a lower surface. The base may further have an aperture formed therein and extending through the upper surface and the lower surface. The implant shield may also have a tubular member coupled with the base. The tubular member may have an inner bore extending longitudinally between a proximal end and a distal end. The inner bore may extend a predetermined length away from the lower surface of the base. The proximal end of the tubular member may be coupled with the base and the inner bore may be substantially aligned with the aperture formed in the base. The inner bore may be operable to receive the implant therethrough and may have a substantially uniform cross-sectional width over the predetermined length. The method may further include inserting the distal end of the tubular member of the implant shield through the incision in the skin of subject and into the dissection tunnel such that the distal end of the tubular member is received in at least a portion of the dissection tunnel or the implant pocket. The method may further include causing the lower surface of the base to substantially engage with at least a portion of the skin adjacent to an incision leading to the implant pocket. The method may also include delivering the implant to the implant pocket by inserting the implant through the aperture of the base and through the inner bore and distal end of the tubular member to the implant pocket. The method may also be used to prevent capsular contracture in a subject resulting from surgical insertion of a breast implant in a surgically created implant pocket through a dissection tunnel connecting the implant pocket to an incision on the skin of the patient.

FIG. 1 depicts an isometric view of a biofilm protection implant shield apparatus 100 for inserting an implant into a surgically-created implant pocket in a subject, according to an exemplary embodiment of the present disclosure. As depicted in FIG. 1, implant shield 100 may include a base 175 having an upper surface 125 and a lower surface 135. The implant shield 100 includes an aperture 120 (not shown in FIG. 1; see FIG. 4) formed in the base 175 and extending through the upper surface 125 and the lower surface 135.

Implant shield 100 further includes a tubular member 150 coupled with the base 175. The tubular member 150 has an inner surface 105, an outer surface 110, a proximal end 151 and a distal end 152. As depicted in FIG. 1, the proximal end 151 is coupled with the base 175 while the distal end 152 of tubular member 150 extends away from the base 175. The tubular member 150 has an inner bore 115 defined by inner surface 105. The outer surface 110 defines an outer bore 195 of tubular member 150 that includes the cross-sectional width of the inner bore 115 as well as the thickness of the wall of the tubular member 150 at the particular portion along the outer surface 110 that the outer bore 195 is determined. The distal end 152 of the tubular member 150 has an aperture 155 that is substantially aligned with inner bore 115 and aperture 120 of the base 175 when the tubular member 150 is extended. As shown in FIG. 1, the inner bore 115 has a longitudinal axis 160 extending therethrough. The longitudinal axis 160 extends substantially perpendicular to the base 175. The inner bore 115 extends longitudinally along the longitudinal axis 160 between the proximal end 151 and the distal end 152 a predetermined length 165 (not shown in FIG. 1; see FIG. 2) away from the lower surface 135 of the base 175. Therefore, the tubular member 150 also extends along the longitudinal axis 160 and substantially orthogonally from the base 175.

As depicted in FIG. 1, the base 175 extends away from tubular member 150 in a direction substantially perpendicular to the longitudinal axis 160. The inner bore 115 is substantially aligned with the aperture 120 formed in the base 175. In at least some instances, the base 175 extends away from tubular member 150 in substantially the same plane as the aperture 120. The aperture 120 and inner bore 115 of tubular member 150 are operable to receive the implant. The proximal end 151 of tubular member 150 is also operable to receive an implant therethrough. The distal end 152 of tubular member 150 is operable to be inserted into an incision in the skin of the subject and further operable to be extended the predetermined length 165 such that the distal end 152 is received into at least a portion of the surgically-created implant pocket or a distal portion of the dissection tunnel connecting an incision in the skin of the subject to the implant pocket. In some instances, at least a portion of the inner bore 115 of the tubular member 150 may extend a second predetermined length above the upper surface 125 of the base 175 (not shown in FIGS. 1-4).

The tubular member 150 of biofilm protection implant shield apparatus 100 is operable to extend along at least a portion of the dissection tunnel during use. The tubular member 150 is also operable to deliver the implant to the implant pocket or a distal portion of the dissection tunnel without the implant contacting the incision site or at least a portion of the dissection tunnel. In some instances, the tubular member 150 of apparatus 100 may be operable to shield the implant from touching any portion of the dissection tunnel or incision site.

Figure 2:
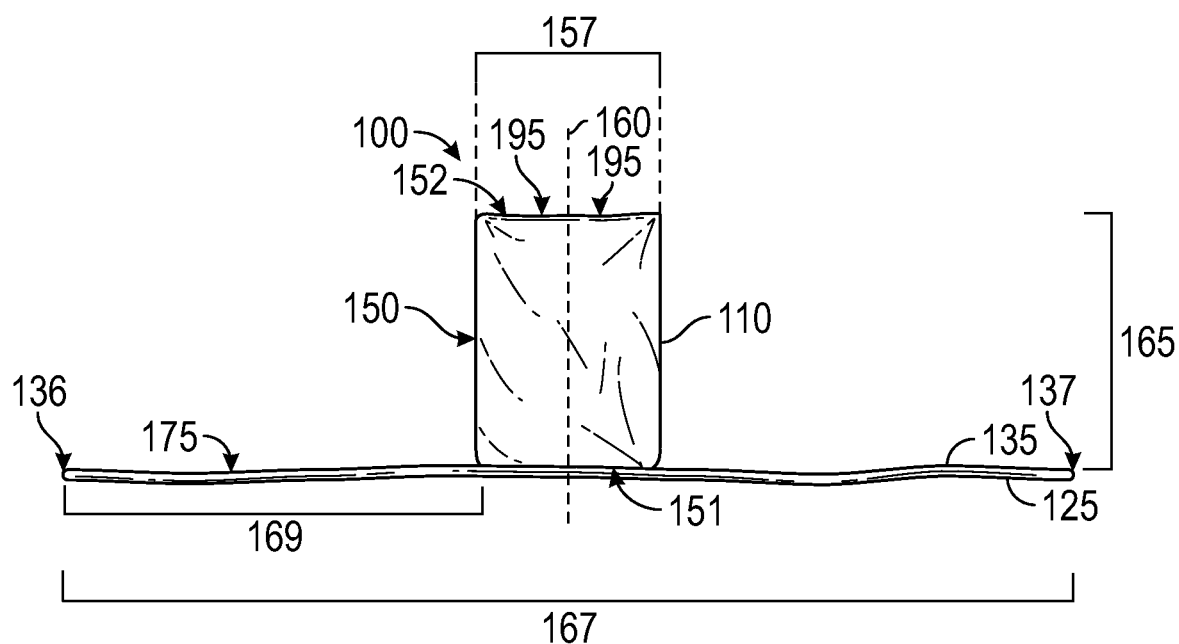
FIG. 2 is a planar view of the implant shield apparatus, according to an exemplary embodiment of the present disclosure.

The inner bore 115 has a substantially uniform cross-sectional width 157 over the predetermined length 165, as depicted in FIG. 2. In at least some instances, the tubular member 150 and/or inner bore 115 is substantially cylindrical in cross-sectional shape. In some instances, the tubular member 150 and/or inner bore 115 may be elliptical in cross-sectional shape. In some cases, the inner bore 115 of tubular member 150 is not tapered along the predetermined length 165. In at least some instances, the distal end 152 has substantially the same cross-sectional width as the cross-sectional width of the proximal end 151. In such cases, the cross-sectional width 157 of the inner bore 115 at the distal end 152 of the tubular member 150 is substantially the same as the cross-sectional width 157 of the inner bore 115 at the proximal end 151 of the tubular member. In some cases, the aperture 155 of the distal end 152 of tubular member 150 has substantially the same cross-sectional width as the cross-sectional width of aperture 120 in base 175. In some cases, the cross-sectional width of the aperture 120 in base 175 may be substantially the same as the cross-sectional width 157 of the inner bore 115 of the tubular member 150.

The cross-sectional width 157 of the inner bore 115 of the tubular member 150 may be any cross-sectional width suitable to receive and facilitate insertion of an implant into the implant pocket of a subject. For example, the cross-sectional width 157 of the inner bore 115 of the tubular member 150 may be from about 3 cm to about 12 cm, or from 3.5 cm to about 9 cm, or from about 3.5 cm to about 8.5 cm, or from about 5 cm to about 8 cm. In at least some instances, the cross-sectional width 157 of the inner bore 115 may be selected based on the size of the implant. In general, pre-filled breast implants are from about 9 cm to about 16 cm (most commonly from about 11 cm to about 12 cm) in diameter but deform and elongate when inserted into the aperture 120 and inner bore 115 of apparatus 100.

As used herein, the term "cross-sectional width" shall include the longest distance between two points on the circumference or edge of the cross-section of an object having a circular and/or non-circular cross-section. The two points may be located on the interior or exterior surface circumference or edge of the cross-section of the object. It should be recognized that "cross-sectional width" of objects having a substantially circular cross-section may be referred to as the "diameter" of the object. The terms "cross-sectional width" and "diameter" may be used interchangeably for objects having a substantially circular cross-section. Understanding that the presently disclosed devices and apparatus, or portions thereof, may be deformable or collapsible or formed from collapsible or deformable materials, the cross-sectional width, as referred to herein, is generally measured in the open and/or extended configuration, such as that typical during use.

While FIGS. 1-4 depict the inner bore 115 of the tubular member 150 as substantially circular in cross-sectional profile, inner bore 115 may have any cross-sectional profile, including conical, elliptical, oval, or circular. Likewise, the outer bore 195 or outer profile of the tubular member 150, as defined by outer surface 110 of the tubular member 150, may be conical, elliptical, oval, or circular. In at least some instances the distal end 152 and the proximal end 151 of inner bore 115 have the same cross-sectional profile, wherein the cross-sectional profile is selected from the group consisting of circular, elliptical, and oval. For example, in cases in which the distal end 152 and the proximal end 151 of inner bore 115 have the same cross-sectional profile, the cross-sectional profile of both the distal end 152 and the proximal end 151 of inner bore 115 could have an elliptical cross-sectional profile, or both could have a circular cross-sectional profile, or both could have an elliptical cross-sectional profile. In other cases, the distal end 152 of inner bore 115 may have a cross-sectional profile that is different than the cross-sectional profile of the proximal end 151. For example, in such cases, the distal end 152 may have a cross-sectional profile that is elliptical while the proximal end 151 may have a circular cross-sectional profile. In cases in which the distal end 152 and the proximal end 151 of inner bore have different cross-sectional profiles, they may still have the substantially the same cross-sectional width. It should be recognized that when the cross-sectional profile of a portion of the inner bore 115 is circular, elliptical, or oval, the three-dimensional profile (e.g., the exterior profile or shape) of a corresponding portion of tubular member 150 may also be, respectively, circular, elliptical, or oval.

According to at least one aspect of the present disclosure, the base 175 is operable to engage the skin of the subject so as to enable the tubular member 150 to stay in place during implant insertion as well as to enable the tubular member 150 to better resist the frictional forces created by insertion of the implant into the inner bore 115 so that the tubular member 150 is operable to shield the implant from the dissection tunnel during transit of the implant along the inner bore to the implant pocket. The lower surface 135 of base 175 is operable to engage the skin of the subject adjacent to an incision so as to resist movement of the base 175 when the implant is inserted into the aperture 120 and the inner bore 115 of tubular member 150. During use, the aperture 120 and inner bore 115 of tubular member 150 substantially overlies at least a portion of the incision. In at least some instances, the lower surface 135 is operable to frictionally engage the skin of a subject. In such cases, the frictional engagement resists movement of the base 175 relative to the skin of the subject during use. In at least some instances, the lower surface 135 may include a textured surface.

In some cases, the lower surface 135 may include a surface operable to engage the skin of a subject once it is wetted with a liquid or a fluid. In such cases, the liquid may be, for example, an aqueous solution, water, a saline solution, or any combination thereof. Other liquids or fluids may also be used to wet the lower surface 135 so long as the wetting of the lower surface by that liquid or fluid provides for sufficient engagement of lower surface 135 with the skin of the subject such that movement of the base 175 is resisted during use. In at least some instances, the liquid or fluid may be disposed on the lower surface 135 of base 175 or may be applied or otherwise disposed on the skin of the subject.

In other cases, an adhesive may be disposed on the lower surface 135. Any adhesive may be used so long as the adhesive provides for sufficient engagement of lower surface 135 with the skin of the subject such that movement of the base 175 is resisted during use. In some instances, the adhesive may be applied to the skin of the subject prior to engagement of the lower surface 135 of base 175 with the skin of the subject.

In at least some instances, a removable backing (not shown in FIGS. 1-4) may be included on the lower surface 135 of base 175. The removable backing may serve to protect or otherwise keep clean the lower surface 135 prior to use. In instances in which an adhesive is disposed on the lower surface 135, the removable backing may cover and protect the adhesive prior to use.

The tubular member 150 is operable to deliver the implant subdermally to the implant pocket, or a distal portion of the dissection tunnel, through the predetermined length 165 of inner bore 115 of the tubular member 150. In at least some instances, the predetermined length 165 may be determined based on a distance between an incision in the skin of a patient and a surgically-created implant pocket formed below the skin. In other cases, the predetermined length 165 may be based on a distance between an incision in the skin and the length of the dissection tunnel or portion of a dissection tunnel connecting the incision to the surgically-created implant pocket. In some instances, the predetermined length 165 between the proximal end 151 and the distal end 152 extends the inner bore 115 operably to deliver an implant subdermally through the aperture 120 and inner bore 115 and into the surgically-created implant pocket or a distal portion of the dissection tunnel or when the lower surface 135 of base 175 is adjacently engaged with the skin of a subject and the distal end 152 is received into at least a portion of the implant pocket or distal portion of the dissection tunnel.

The predetermined length 165 of the inner bore 115 of the tubular member 150 may be adjusted based on the desired depth of insertion into the dissection tunnel, the size of the implant used, the location of the incision, and the characteristics of the subject's breast. In at least some instances, the predetermined length 165 of the inner bore 115 may have a predetermined length 165 equal to or less than the measured length of the dissection tunnel. In some instances, the predetermined length 165 of the inner bore 115 of the tubular member 150 may be greater than 1 cm, or greater than 1.5 cm, or greater than 2 cm, or greater than 2.5 cm, or greater than 3 cm, or greater than 3.5 cm, or greater than 4 cm, or greater than 4.5 cm, or greater than 5 cm, or greater than 5.5 cm, or greater than 6 cm, or greater than 6.5 cm, or greater than 7 cm, or greater than 7.5 cm, or greater than 8 cm. In other instances, the predetermined length 165 may be from about 2 cm to about 10 cm, or from about 3 cm to about 10 cm, or from about 2 cm to about 8 cm, or from about 2 cm to about 5 cm, or from about 3 cm to about 8 cm.

Biofilm protection implant shield apparatus 100, including tubular member 150 and base 175, may be made of any suitable flexible material. For example, the flexible material may include, but is not limited to, plastic-containing fabrics, polymers, plastics, mylar, vinyls, polyvinyl chloride, ethylene and alpha-olefin copolymers, silicone, solid silicone, silicone rubber, and any combination thereof. In some cases, the tubular member 150 and base 175 may be formed from the same material. In some instances, the flexible material may be resistant to stretching. In some instances, the tubular member 150 and the base 175 may be integrally formed. In some instances, the flexible material may be a transparent or semi-transparent flexible material.

In other instances, biofilm protection implant shield apparatus 100, including tubular member 150 and base 175, may be stretchable and/or made of a flexible material that is stretchable. As used herein, the term "stretchable" refers to a material, or property of a device or device component, that may be extensible or elastomeric. That is, a stretchable material, or a stretchable device or device component, may be extended, deformed, or the like, without breaking, and may or may not significantly retract after removal of an extending force. As used herein, the terms "elastomeric" or "elastic" are used interchangeably to refer to that property of a material (or device or device component) where upon removal of an elongating force, the material (or device or device component) is capable of recovering to substantially is unstretched size and shape or the material exhibits a significant retractive force. As used herein, the term "extensible" refers to that property of a material (or device or device component) where upon removal of an elongating force, the material (or device or device component) experiences a substantially permanent deformation or the material does not exhibit a significant retractive force.

In particular, tubular member 150 may be stretchable and/or comprise a stretchable material. Stretchability of the tubular member 150 provides the advantage that when retractors are placed inside of the tubular member 150 during use to open up the dissection tunnel, the tubular member 150 may stretch to allow greater opening of the dissection tunnel as well as engagement of the walls of the dissection tunnel thereby providing effective shielding for the implant as well as reducing the frictional forces associated with implant insertion. The stretchability of the tubular member 150 also provides the advantage of stretching during insertion of the implant so as to reduce the forces associated with implant insertion and to facilitate transit of the implant to the implant pocket while providing the implant shielding function, whether retractors are placed within tubular member 150 during use or not. In at least some instances, the tubular member 150 may be elastic or comprise an elastic material. In other instances, the tubular member 150 may be extensible or comprise an extensible material.

In at least some instances, the tubular member 150 may be made of a material that is different than the material that makes up the base 175. For example, while it is advantageous in at least some instances that the tubular member be stretchable or made of a stretchable material, base 175 does not necessarily need to be stretchable or made of a stretchable material. In other instances, base 175 may comprise the same material as tubular member 150 but the stretchability of tubular member 150 is determined by the thickness of the material. In other words, tubular member 150 may be constructed of a material that is thin enough to be stretchable during use while the base 175 may be constructed of the same material but may not be stretchable due to the chosen thickness of the base 175.

In some cases, the inner bore 115 may include a lubricant along the inner surface 105 that defines the inner bore 115. In such cases, the lubricant along the inner surface 105 of the inner bore 115 may facilitate insertion and passage of the implant into and through aperture 120 and inner bore 115. In some instances, the outer surface 110 of the tubular member 150 may include a lubricant. In such cases, the lubricant on the outer surface 110 may facilitate insertion of the tubular member 150 into the dissection tunnel. The lubricant may be, for example, a sterile lubricant selected from the group consisting of a surgical lubricant, a water-based lubricating jelly, a dry lubricant, a powdered lubricant, a moisture-activated lubricant, and any combination thereof. The lubricant may be disposed on the inner surface 105 and/or the outer surface 110 at the time of manufacturing and packing. In other instances, the lubricant may be applied to the inner surface 105 and/or the outer surface 110 by a physician or technician prior to use so long as the surfaces and the lubricant remain sterile.

In some instances, the inner bore 115 or inner surface 105 of tubular member 150 may include a lubricating coating or a friction-reducing coating that serves a similar function as the lubricant described above. In some cases, the outer surface 110 of the tubular member 150 may include a lubricating coating or a friction-reducing coating that also serves the same or similar function as the lubricant described above.

FIG. 2 is a planar view of the biofilm protection implant shield apparatus 100, according to an exemplary embodiment of the present disclosure. As depicted in FIG. 2, biofilm protection implant shield apparatus 100 includes base 175 and tubular member 150 extending through the base 175 to form aperture 120 (not shown in FIG. 2; see FIG. 4). The tubular member 150 has an inner bore 115, a proximal end 151 and a distal end 152. The base 175 radially extends from at least a portion of the proximal end 151 of tubular member 150. The inner bore 115 has a longitudinal axis 160 therethrough which extends substantially perpendicular and/or orthogonally to the base 175. As shown in FIG. 2, the inner bore 115 extends longitudinally a predetermined length 165 away from the lower surface 135 of the base 175 and between the proximal end 151 and the distal end 152. The tubular member 150 likewise extends along the longitudinal axis 160 a predetermined length 165 away from the lower surface 135 of the base 175 and substantially perpendicular and/or orthogonally to the base 175.

Figure 3:
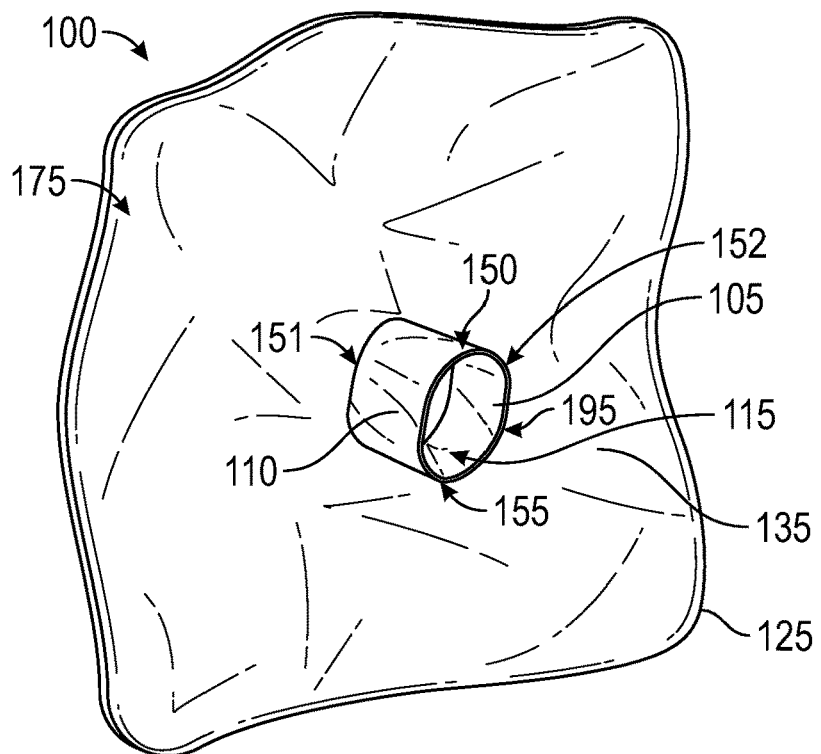
FIG. 3 is a front diagrammatic view of the implant shield apparatus showing the distal end of tubular member and the lower surface of the base, according to an exemplary embodiment of the present disclosure.
Figure 4:
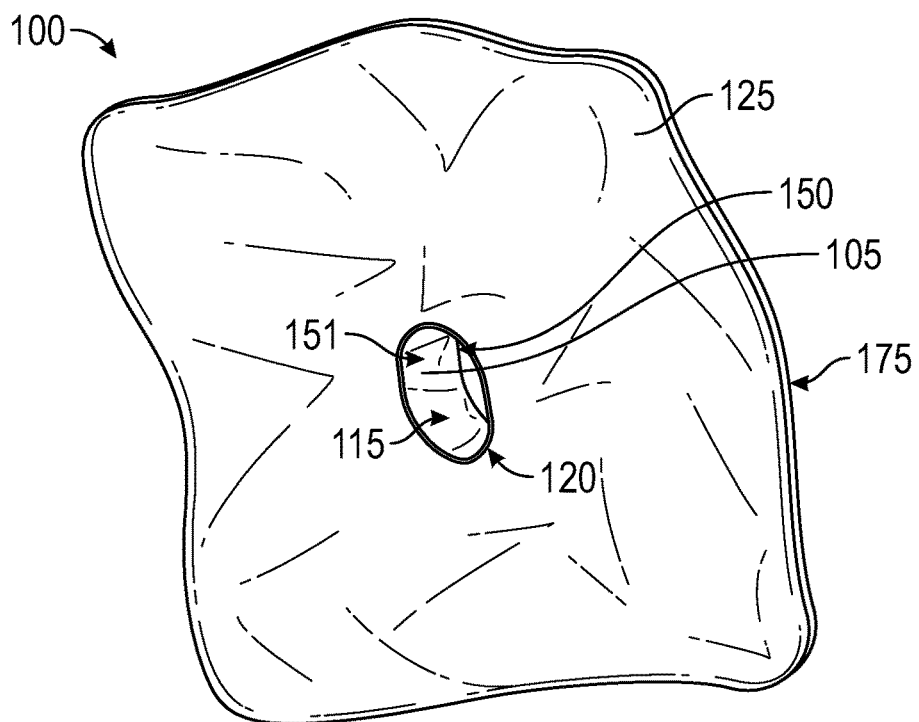
FIG. 4 is a rear diagrammatic view of the implant shield apparatus showing the proximal end of the tubular member and the upper surface of the base, according to an exemplary embodiment of the present disclosure.

FIG. 3 is a front diagrammatic view of the biofilm protection implant shield apparatus 100 showing the distal end 152 of tubular member 150 and the lower surface 135 of the base 175, according to an exemplary embodiment of the present disclosure. As depicted in FIG. 3, the proximal end 151 of tubular member 150 is coupled with base 175 of the biofilm protection implant shield apparatus 100. The distal end 152 of the tubular member 150 comprises aperture 155 through which an implant may exit after transiting through at least a portion of the dissection tunnel during delivery to the implant pocket. FIG. 4 is a rear diagrammatic view of the biofilm protection implant shield apparatus 100 showing base 175 having an aperture 120 formed therein and extending through the upper surface 125 and the lower surface 135.

Figure 5:
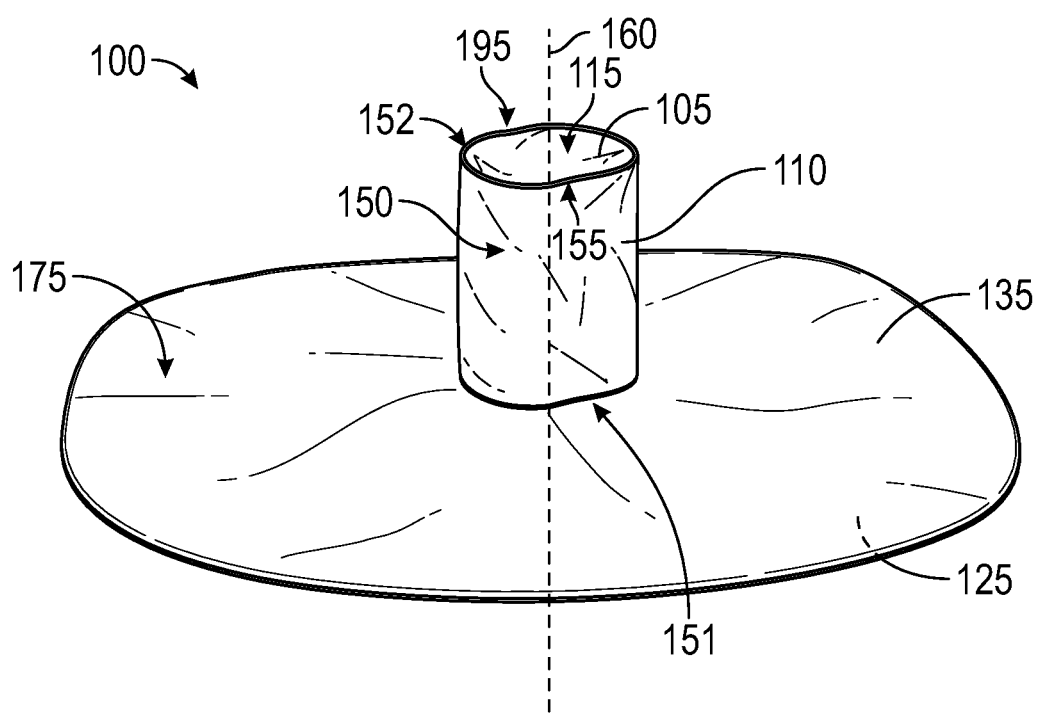
FIG. 5 is an isometric view of an implant shield apparatus having a substantially circular base, according to an exemplary embodiment of the present disclosure.

The base 175 can have any shape, configuration, diameter, or thickness so long as the base 175 is operable to substantially engage with at least a portion of the skin adjacent to an incision leading to the implant pocket, and/or is operable to engage the skin of the subject adjacent to an incision so as to resist movement of the base 175 when the implant is inserted into the aperture 120 and the inner bore 115 of tubular member 150, and/or is operable to substantially protect the implant from contamination from the microbial flora that may be present on the skin of the subject during insertion of the implant into the aperture 120 and the inner bore 115 of tubular member 150. For example, in at least some instances, the base 175 may be substantially rectangular as shown in FIGS. 1-4, or the base 175 may be, for example, substantially circular as shown in FIG. 5.

As depicted in FIG. 2, the base 175 may have a diameter 167. As used herein, the diameter 167 of base 175 is defined as the minimum distance between two opposite outer edges of the base 175 when the base 175 is fully extended away from the tubular member 150 (e.g., the same position or configuration as when the base is engaged with the skin of the subject). For example, as shown in FIG. 2, the diameter 167 of base 175 is the distance between first outer edge 136 and an opposite second outer edge 137. The base 175 may have any diameter sufficient to be operable to engage the skin of the subject and to resist movement of the base 175 when the implant is inserted into the aperture 120 and the inner bore 115 of the tubular member 150. The base 175 may also have any diameter sufficient to substantially protect the implant from contamination from the microbial flora that may be present on the skin of the subject during insertion of the implant into aperture 120. In at least some instances, the base 175 may have a diameter 167 that is at least 3 times greater than the cross-sectional width 157 of the inner bore 115 of the tubular member 150 and/or the aperture 120 and/or the outer bore 195 of the tubular member 150. In other instances, the base 175 may have a diameter 167 that is from about 3 times to about 5 times the cross-sectional width 157 of the inner bore 115 of the tubular member 150 and/or the aperture 120 and/or the outer bore 195 of the tubular member 150. For example, if the cross-sectional width 157 of the inner bore 115 is 5 cm, then the diameter 167 of the base 175 may be from about 15 cm to about 25 cm. In other instances, the diameter 167 of base 175 may be from about 9 cm to about 60 cm, or from about 10.5 cm to about 45 cm, or from about 10.5 cm to about 42.5 cm, or from about 15 cm to about 24 cm, or from about 20 cm to about 32 cm, or from about 25 cm to about 40 cm.

The base 175 may also have a radial length 169, as shown in FIG. 2. As used herein, the radial length 169 of base 175 is defined as the distance between an outer edge (e.g., outer edges 136,137) of the base 175, when the base 175 is fully extended away from the tubular member 150 (e.g., the same position or configuration as when the base is engaged with the skin of the subject), and the outer surface 110 of the proximal end 151 of the tubular member 150 where it is coupled to the base 175. Accordingly, the radial length 169 of the base 175 is the length that the base 175 extends away from the tubular member 150. The base 175 may have any radial length sufficient to be operable to engage the skin of the subject and to resist movement of the base 175 when the implant is inserted into the aperture 120 and the inner bore 115 of the tubular member 150. The base 175 may also have any radial length sufficient to substantially protect the implant from contamination from the microbial flora that may be present on the skin of the subject during insertion of the implant into aperture 120. In at least some instances, the base 175 may have a radial length 169 that is greater than or equal to the cross-sectional width 157 of the inner bore 115 of the tubular member 150 and/or the aperture 120 and/or the outer bore 195 of the tubular member 150. In other instances, the base 175 may have a radial length 169 from about one (1) to about two (2) times the cross-sectional width 157 of the inner bore 115 of the tubular member 150 and/or the aperture 120 and/or the outer bore 195 of the tubular member 150. For example, if the cross-sectional width 157 of the inner bore 115 is 5 cm, then the radial length 169 of the base 175 may be from about 5 cm to about 10 cm. In other instances, the radial length of base 175 may be from about 3 cm to about 12 cm, or from about 3.5 cm to about 18 cm, or from about 3.5 cm to about 17 cm, or from about 5 cm to about 8 cm, or from about 10 cm to about 16 cm, or from about 5 cm to about 16 cm.

Base 175 may have sufficient thickness to provide structural support or rigidity to the biofilm protection implant shield apparatus 100 such that the implant may be easily inserted into aperture 120 and such that the base sufficiently resists the forces associated with implant insertion to provide stability for the tubular member 150 when the base 175 is engaged with the skin of the subject. Base 175 may also have sufficient thickness to provide enough structural support and rigidity to resist movement of the base relative to the skin of the subject, to which the base 175 is engaged, during insertion of the implant into aperture 120 and passage of the implant through the inner bore 115 of the tubular member 150. In some instances, the base 175 may have a thickness (e.g., the distance or thickness between the lower surface 135 and the upper surface 125 of base 175) that is substantially the same as the thickness of the tubular member 150. In other instances, the base 175 may have a thickness that is substantially thicker than the thickness of the tubular member 150. In other instances, the base 175 may have a thickness that is substantially thinner than the thickness of the tubular member 150. In such instances, the tubular member 150 may be thicker than the thickness of the base 175 so that the tubular member 150 has sufficient rigidity or structural integrity to facilitate insertion into the dissection tunnel while resisting the forces created by insertion of the implant into the inner bore 115 such that the tubular member 150 is operable to shield the implant from the dissection tunnel during transit of the implant along the inner bore to the implant pocket.

Importantly, base 175 operably engages with the skin of the subject such that apparatus 100 does not need to be held by a surgeon or assistant during insertion of the implant into aperture 120 and inner bore 115, even during insertion of pre-filled breast implants which are accompanied by much higher forces of insertion. Apparatus 100 is particularly suited to the delivery of pre-filled breast implants because base 175 is operable to protect the implant from contamination from the skin while stabilizing the tubular member 150 and resisting movement during pre-filled implant insertion, which is accompanied by large compressional and frictional forces associated with deformation of the pre-filled implant during insertion and transit along the length of the inner bore 115 to the implant pocket. Base 175 does not displace from the skin of the subject during implant insertion even during insertion of pre-filled implants and when the base 175 or any other portion of the device is not held by a surgeon or assistant.

Figure 6A:
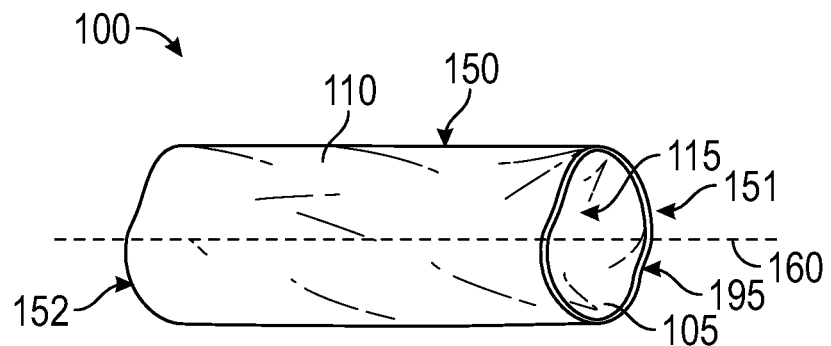
FIG. 6A is a rear diagrammatic view of an implant shield apparatus in an unrolled configuration in which an end of the tubular member may be rolled on itself to form a base, according to an exemplary embodiment of the present disclosure.
Figure 6B:
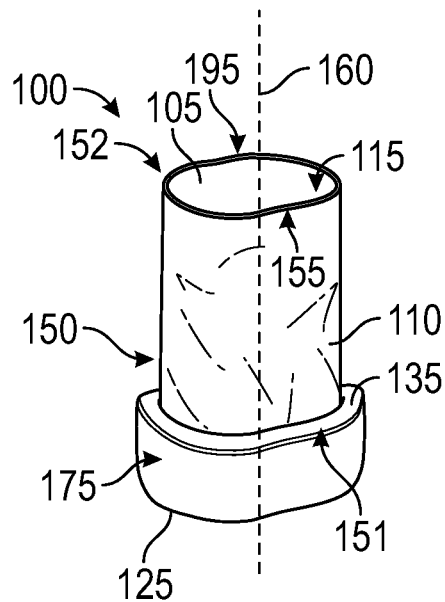
FIG. 6B is an isometric view of an implant shield apparatus in the rolled configuration in which an end of the tubular member is rolled on itself to form a base, according to an exemplary embodiment of the present disclosure.

In some instances, apparatus 100 may include a tubular member 150 that is operable to form a base 175 or otherwise deploy or transition to form a base 175. For example, as shown in FIGS. 6A and 6B, the proximal end 151 of tubular member 150 may be operable to be folded or rolled on itself to form a base 175. In such instances, the base 175 may be formed from successive folds of the proximal end 151 of tubular member 150, as shown in FIG. 6B. Other configurations may be possible in which the tubular member 150 may be deployed or transitioned to form a base 175. All such configurations in which the tubular member 150 may be transitioned from the undeployed configuration shown in FIG. 6A to the deployed configuration shown in FIG. 6B having a suitable base 175 formed from the tubular member 150 are within the scope and spirit of the present disclosure. In at least some instances the length of the inner bore 115 of tubular member 150 may be adjusted by forming the base 175 such that the inner bore 115 has a predetermined length equal to or greater than the length of the dissection tunnel.

Figure 7A:
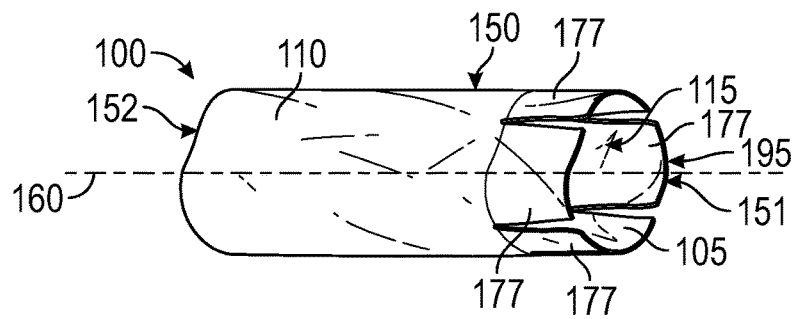
FIG. 7A is a rear diagrammatic view of an implant shield apparatus in the undeployed configuration in which an end of the tubular member is perforated so as to be deployable to form a base, according to an exemplary embodiment of the present disclosure.
Figure 7B:
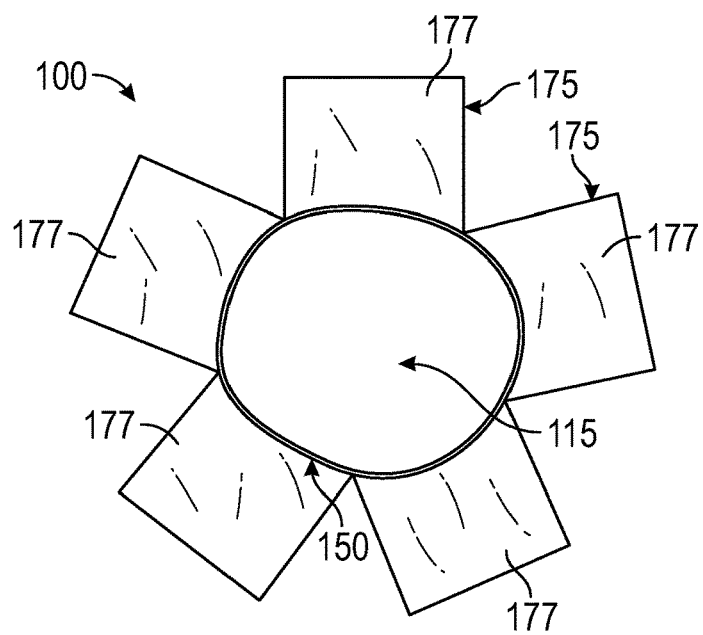
FIG. 7B is a rear end diagrammatic view of an implant shield apparatus in the deployed configuration in which an end of the tubular member is deployed so as to form a base having a plurality of substantially rectangular flanges, according to an exemplary embodiment of the present disclosure.
Figure 7C:
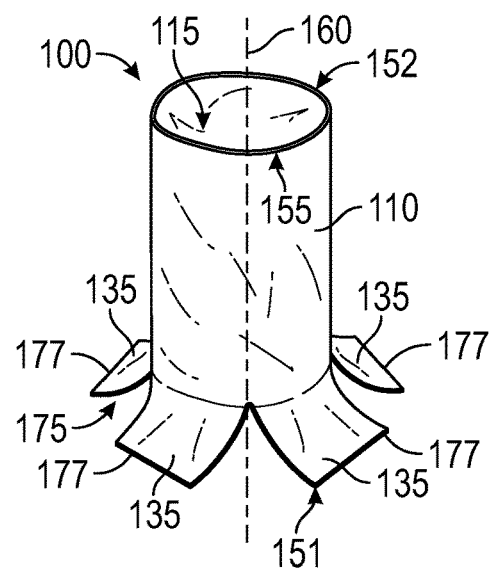
FIG. 7C is an isometric view of an implant shield apparatus in the deployed configuration in which an end of the tubular member is deployed so as to form a base having a plurality of substantially rectangular flanges, according to an exemplary embodiment of the present disclosure.

As depicted in FIGS. 7A-7C, apparatus 100 may include a tubular member 150 that is perforated or perforable at the proximal end 151 such that the tubular member 150 is operable to form a base 175 or otherwise deploy or transition to form a base 175 by the deployment or splaying out of a plurality of flanges 177. FIG. 7A depicts device 100 in the undeployed configuration in which the plurality of flanges 177 are substantially parallel to the longitudinal axis 160. As shown in FIG. 7A, the proximal end 151 of tubular member 150 may comprise a plurality of flanges 177. In at least some instances, a plurality of flanges 177 may be integrally formed on the proximal end 151 of tubular member 150. In some cases, the proximal end 151 of tubular member 150 may be perforated or scored so that a plurality of flanges 177 may be easily separated or formed upon tearing of the perforations or scored portions of tubular member 150, be operable to be folded or rolled on itself to form a base 175.

FIGS. 7B and 7C depict apparatus 100 in the deployed configuration in which the plurality of flanges 177 are splayed out to form base 175 by transitioning from the tubular arrangement in FIG. 7A to the base arrangement in FIG. 7B. As depicted in FIG. 7B, the plurality of flanges 177 extend outward from tubular member 150 such that flanges 177 are perpendicular to the tubular member 150. FIG. 7C depicts the transitioning of the plurality of flanges 177 from the tubular arrangement depicted in FIG. 7A to the base arrangement in which the plurality of flanges 177 are substantially perpendicular to the longitudinal axis 160. In at least some instances, an adhesive may be disposed on the lower surface 135 of each of the plurality of flanges 177. In some instances, the lower surface 135 of each of the plurality of flanges 177 may also include a removable backing that serves to protect or otherwise keep clean the lower surface 135 of each of the plurality of flanges 177 prior to use. In instances in which an adhesive is disposed on the lower surfaces 135, the removable backing may cover and protect the adhesive prior to use.

Figure 8A:
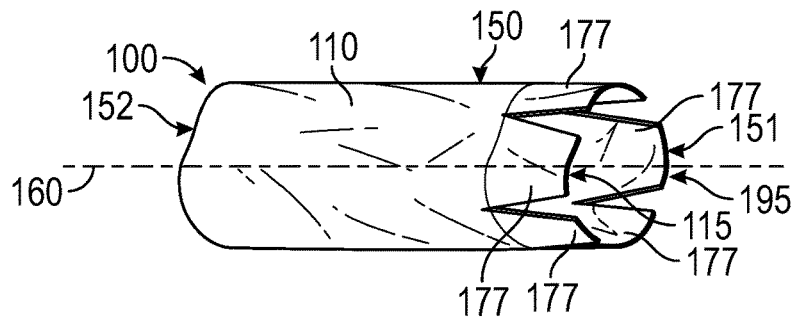
FIG. 8A is a rear diagrammatic view of an implant shield apparatus in the undeployed configuration in which an end of the tubular member is perforated so as to be deployable to form a base, according to an exemplary embodiment of the present disclosure.
Figure 8B:
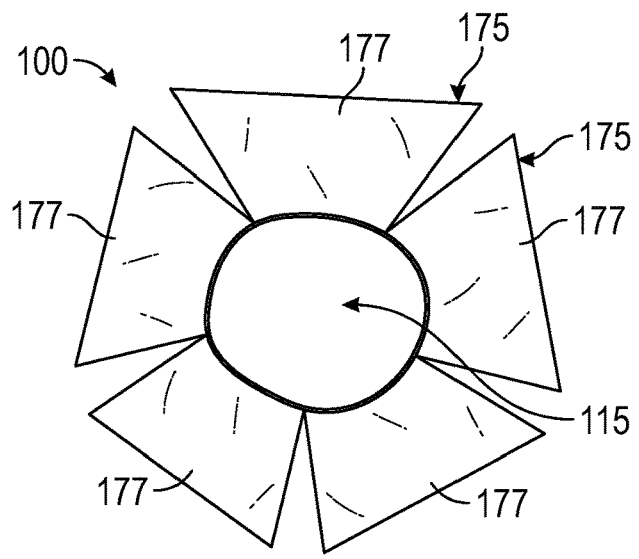
FIG. 8B is a rear end diagrammatic view of an implant shield apparatus in the deployed configuration in which an end of the tubular member is deployed so as to form a base having a plurality of substantially trapezoidal flanges, according to an exemplary embodiment of the present disclosure.
Figure 8C:
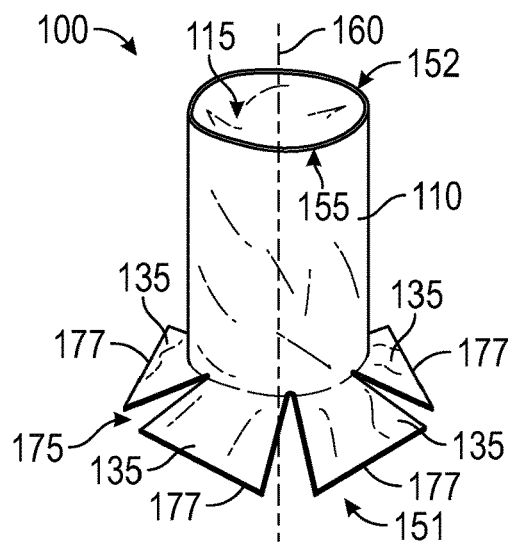
FIG. 8C is an isometric view of an implant shield apparatus in the deployed configuration in which an end of the tubular member is deployed so as to form a base having a plurality of substantially trapezoidal flanges, according to an exemplary embodiment of the present disclosure.

The plurality of flanges 177 may have any shape so long as they are operable to form base 175 as described herein. While the plurality of flanges 177 are depicted in FIGS. 7A-7C as substantially rectangular in shape, the plurality of flanges 177 may have any other shape including a substantially trapezoidal shape depicted in FIGS. 8A-8C.

The present disclosure also provides a system that includes the biofilm protection implant shield apparatus 100 and an implant capable of being inserted by the biofilm protection implant shield apparatus. The present disclosure further provides a system that includes the biofilm protection implant shield apparatus 100 and a conical sleeve. The conical sleeve has an interior cavity, a first terminus, and a second terminus. The first terminus of the conical sleeve has a larger diameter than the second terminus. Therefore the conical sleeve is tapered along its length. The second terminus of the conical sleeve is operable to be inserted into the aperture 120 or inner bore 115 of the tubular member 150 of the apparatus 100. The conical sleeve is further operable to receive an implant into its interior cavity via the first terminus and deliver the implant through the second terminus into the inner bore 115 of the apparatus 100 when the lower surface 135 of the base 175 is engaged with the skin of the subject. In at least some instances, the system further includes an implant that may be inserted by the conical sleeve.

The present disclosure also provides a kit that includes the biofilm protection implant shield apparatus 100 packaged together with an implant capable of being inserted by the biofilm protection implant shield apparatus. The present disclosure further provides a kit that includes the biofilm protection implant shield apparatus 100 packaged together with a conical sleeve. The conical sleeve has an interior cavity, a first terminus, and a second terminus. The first terminus of the conical sleeve has a larger diameter than the second terminus. Therefore the conical sleeve is tapered along its length. The second terminus of the conical sleeve is operable to be inserted into the aperture 120 or inner bore 115 of the tubular member 150 of the apparatus 100. The conical sleeve is further operable to receive an implant into its interior cavity via the first terminus and deliver the implant through the second terminus into the inner bore 115 of the apparatus 100 when the lower surface 135 of the base 175 is engaged with the skin of the subject. In at least some instances, the kit further includes an implant that may be inserted by the conical sleeve.

The apparatus, systems, kits, and methods of the present disclosure may be used with any implants. For example, the implant may be, but is not limited to, filled implants, unfilled implants, saline implants, silicone gel implants, textured implants, smooth implants, highly cohesive silicone gel implants, oil-filled implants, and prosthesis implants. The subject may be any subject in need of an implant. The subject may be, for example, but not limited to, a mammal or a human. In some cases, the subject may be a human and the implant may be a breast implant. While FIGS. 9-32 illustrate methods of using the presently disclosed apparatus and techniques of using the apparatus for inserting a breast implant into a human subject, one of skill in the art will understand and appreciated the depicted methods may be used for any type of implant in any type of subject in need thereof. FIGS. 9-32 illustrate methods for inserting an implant into a surgically-created implant pocket in a subject using the biofilm protection implant shield apparatus 100 disclosed herein. FIGS. 9-16, 18-20, and 29-31 depict methods for use of the presently disclosed biofilm protection implant shield apparatus 100 in the case of a periareolar incision and implant insertion, whereas FIGS. 17, 21-28, and 32 depict methods for use of the implant shield apparatus 100 in the case of an inframammary incision and implant insertion.

Figure 9:
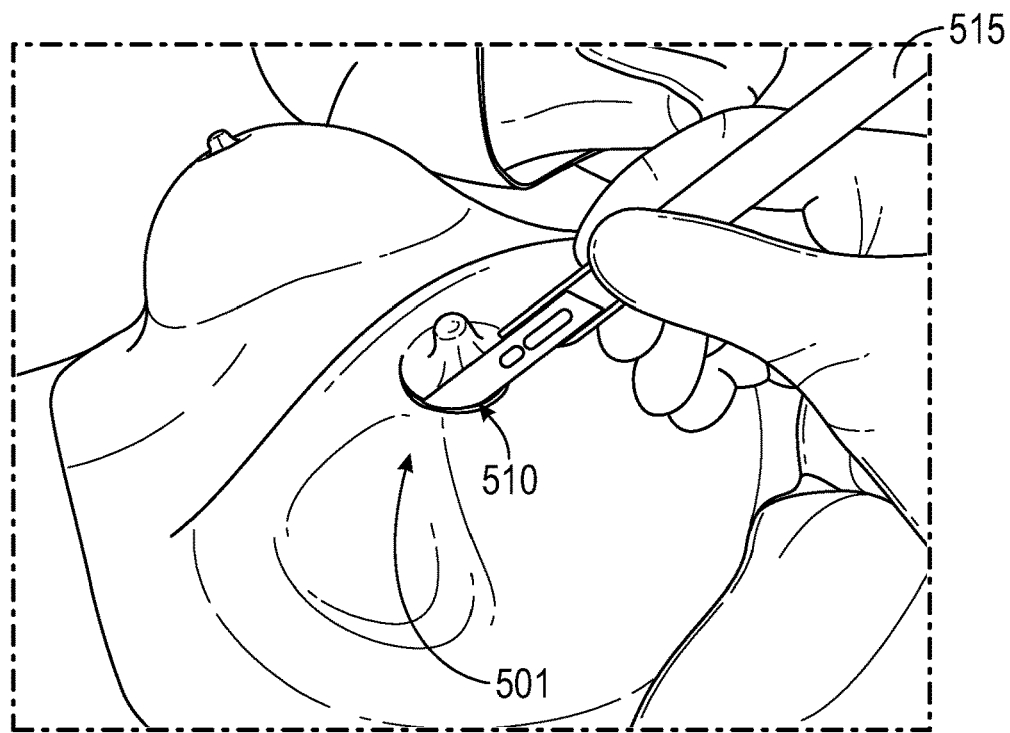
FIG. 9 is an illustration depicting the creation of a periareolar incision in the breast of a subject; according to an exemplary embodiment of the present disclosure.

In order for the implant to be inserted into the surgically-created implant pocket it must first pass through the incision in the skin of the subject and through the dissection tunnel connecting the implant pocket to the incision. As depicted in FIG. 9, a periareolar incision 510 in the skin 501 of the subject is created by scalpel 515.

Figure 10:
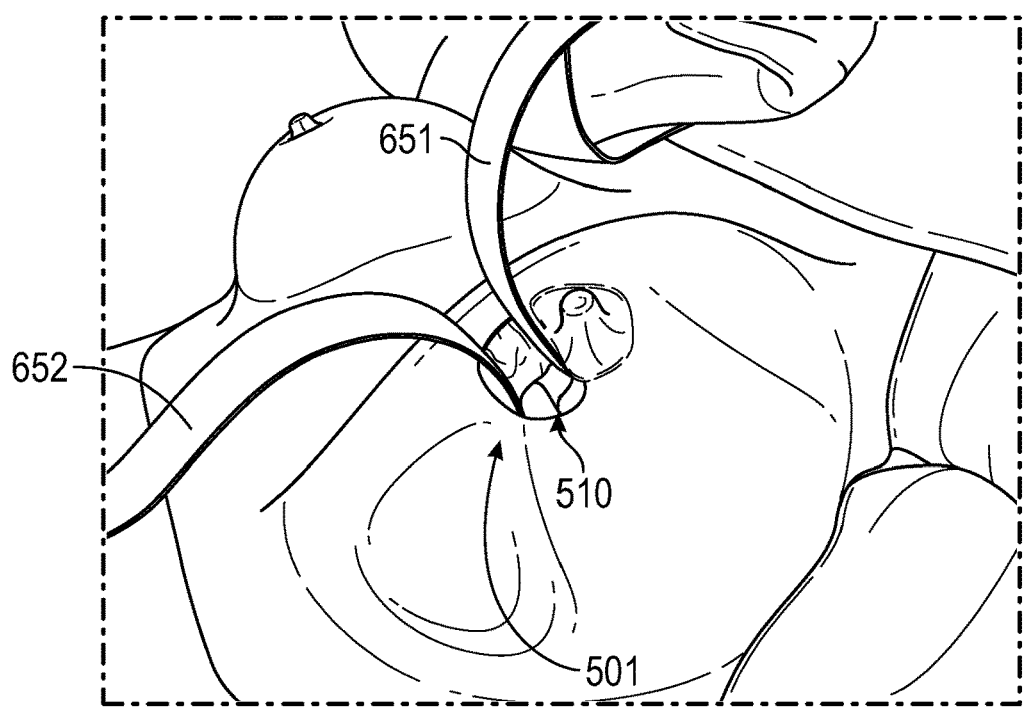
FIG. 10 is an illustration depicting the opening of the periareolar incision using two retractors, according to an exemplary embodiment of the present disclosure.

FIG. 10 depicts the use of retractors 651, 652 to open the periareolar incision 510 and to facilitate full surgical dissection of the implant pocket and the dissection tunnel connecting the implant pocket to the incision. Apparatus 100 is a shield rather than a retractor and is not capable of dilating the incision or holding open the incision during use like a retractor. However, unlike a retractor, the tubular member 150 of apparatus 100 is much quicker and easier to insert into the incision and dissection tunnel and therefore requires less manipulation. The less required manipulation and speed and ease of use of apparatus 100 results in less contamination risk to the implant and greater effectiveness of biofilm shielding. Additionally, since the distal end 152 of the tubular member 150 does not include or require a retracting member, apparatus 100 provides for easy adjustment of the predetermined length 165 prior to use by cutting the distal end 152 of the tubular member 150 to the desired predetermined length 165. Apparatus 100 may be used in conjunction with separate retractors, such as retractors 651, 652 shown in FIG. 11, which allows the dissection tunnel and implant pocket to be opened up and reduces the resistance of the implant to insertion as well as reduces the external force required for insertion and delivery of the implant to the implant pocket.

Figure 11:
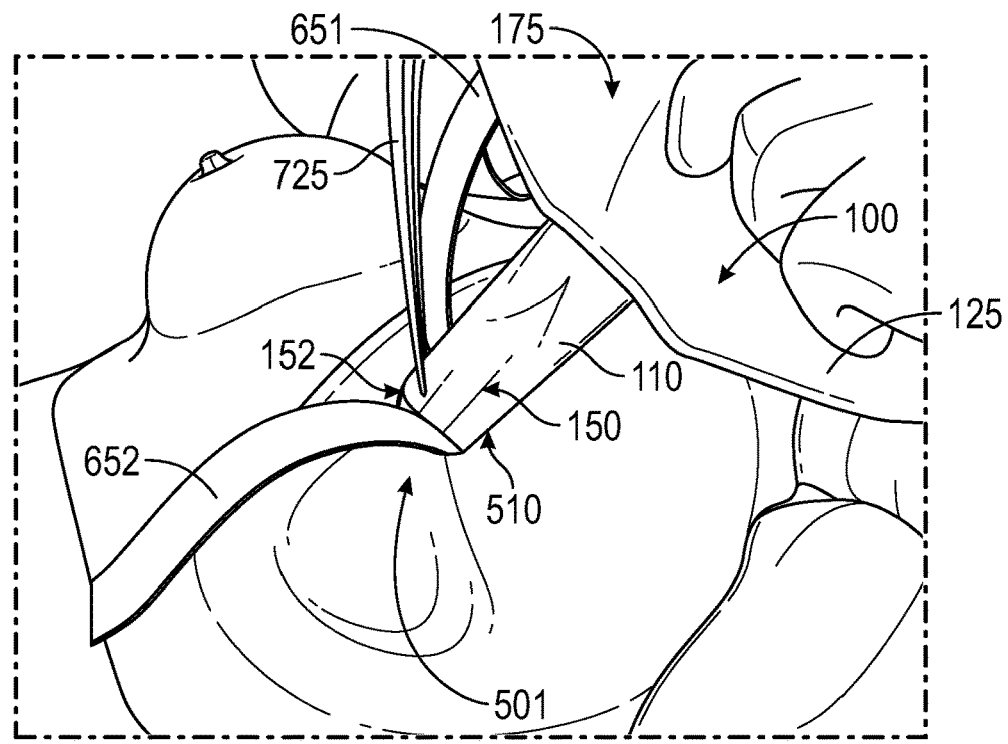
FIG. 11 is an illustration depicting insertion of the distal end of the tubular member of the implant shield into the dissection tunnel connecting the periareolar incision to the surgically-created implant pocket, according to an exemplary embodiment of the present disclosure.

While FIG. 11 depicts the use of retractors during use of apparatus 100, one of skill in the art will understand that in other instances, apparatus 100 may be used without retractors particularly depending on the type, nature, and size of the implant being inserted. Additionally, tubular member 150 may be stretchable or comprise a stretchable material providing for expansion of the dissection tunnel during insertion of the implant into the stretchable tubular member 150. In such cases, the tubular member 150 may stretch to accommodate the implant as well as to engage the walls of the dissection tunnel so that the dissection tunnel is opened sufficient for implant insertion while the tubular member 150 shields the implant from the dissection tunnel or a portion thereof. The stretchability of the tubular member 150 also provides the advantage that when retractors are placed inside of the tubular member 150 during use to open up the dissection tunnel, the tubular member 150 may stretch to allow greater opening of the dissection tunnel as well as engagement of the walls of the dissection tunnel thereby providing effective shielding for the implant as well as reducing the frictional forces associated with implant insertion. The stretchability of the tubular member 150 also provides the advantage of stretching during insertion of the implant so as to reduce the forces associated with implant insertion and to facilitate transit of the implant to the implant pocket while providing the implant shielding function, whether retractors are placed within tubular member 150, placed between the tubular member 150 and the walls of the dissection tunnel, or not used at all.

Figure 12:
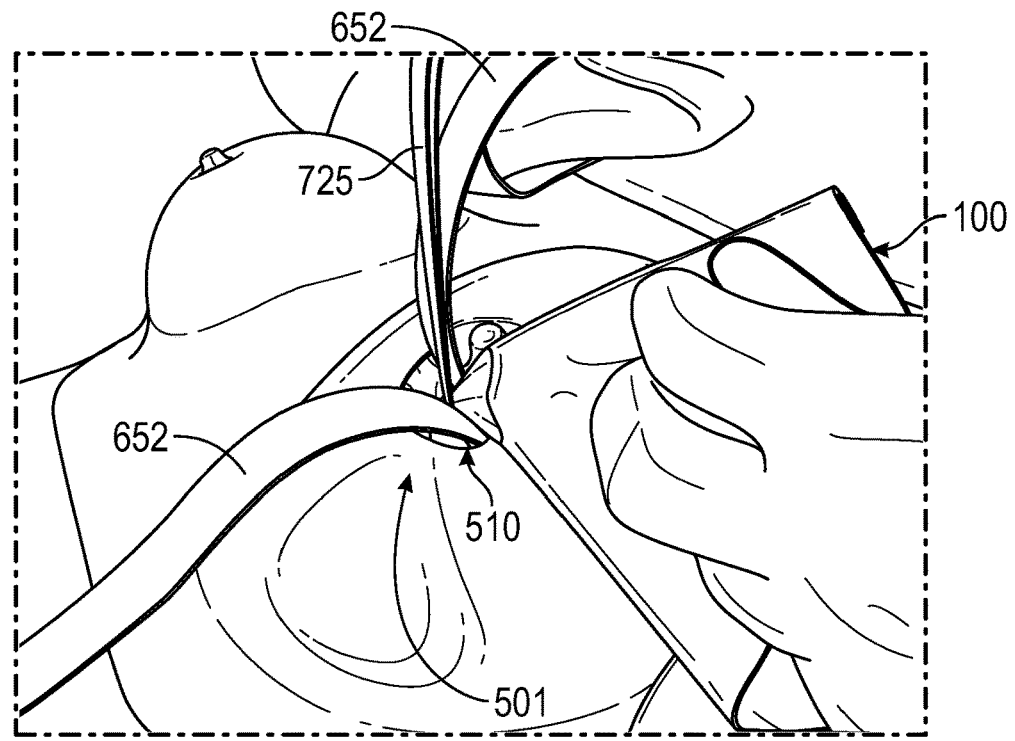
FIG. 12 is an illustration depicting further insertion of the tubular member into the dissection tunnel, according to an exemplary embodiment of the present disclosure.

As depicted in FIG. 11, the incision 510 and the dissection tunnel are further opened using retractors 651, 652 to facilitate insertion of the tubular member 150 of apparatus 100. In particular, the distal end 152 of the tubular member 150 is inserted through the incision 510 and into the dissection tunnel using any suitable sterile insertion tool, such as forceps 725. As shown in FIG. 12, the tubular member 150 is further inserted into the dissection tunnel such that the distal end 152 of the tubular member 150 is received in at least a portion of the dissection tunnel or the implant pocket.

The distal end 152 of the tubular member 150 is generally inserted into the dissection tunnel to a depth greater than 1 cm below the incision so as to sufficiently shield the implant during insertion into the dissection tunnel and implant pocket. In general, it is not necessary for the tubular member 150 to shield the implant from the entire length of the dissection tunnel since often only a portion of the dissection tunnel is formed through breast tissue (glandular tissue) which may be colonized by microbes, thereby posing a risk of microbial contamination to the otherwise sterile implant. Often, the remaining portions of the dissection tunnel are formed through sterile muscle or adipose tissue that do not pose a significant contamination risk to the implant during its transit to the implant pocket. Generally, the upper dissection tunnel comprises breast tissue and/or glandular tissue while the lower dissection tunnel comprises tissue other than breast or glandular tissue, such as muscle or adipose tissue. As used herein, the upper dissection tunnel refers to the portion of the dissection tunnel beginning at the incision in the skin of the patient and extending downward for so long as the walls of the dissection tunnel are formed through breast and/or glandular tissue. The lower dissection tunnel, as used herein, refers to the portion of the dissection tunnel beginning at the first instance of tissue other than breast and/or glandular tissue, such as muscle or adipose tissue and extending to the implant pocket. Therefore, the upper dissection tunnel is the upper most portion of the dissection tunnel connecting the incision in the skin of the patient to the lower dissection tunnel which in turn extends to the implant pocket. The length of the upper dissection tunnel can be measured intraoperatively and used to determine the predetermined length of the inner bore 115 and tubular member 150. In at least some instances, the distal end 152 of tubular member 150 is inserted into the dissection tunnel such that the entire length of the upper dissection tunnel is shielded from the implant during transit of the implant to the implant pocket. In such cases, the distal end 152 is inserted into the dissection tunnel to a depth equal to or greater than the length of the upper dissection tunnel. In other instances, the distal end 152 may be inserted into the dissection tunnel such that at least a portion of the upper dissection tunnel is shielded from the implant during transit of the implant to the implant pocket.

In at least some instances, the distal end 152 of the tubular member 150 is inserted greater than 1.5 cm, or greater than 2 cm, or greater than 2.5 cm, or greater than 3 cm, or greater than 3.5 cm, or greater than 4 cm, or greater than 4.5 cm, or greater than 5 cm, or greater than 5.5 cm, or greater than 6 cm, or greater than 6.5 cm, or greater than 7 cm, or greater than 7.5 cm, or greater than 8 cm, below the incision. In at least some instances, the distal end 152 of the tubular member 150 is inserted into the dissection tunnel to a depth of from about 2 cm to about 10 cm, or from about 3 cm to about 10 cm, or from about 2 cm to about 8 cm, or from about 2 cm to about 5 cm, or from about 3 cm to about 8 cm, below the incision. The depth of insertion will generally depend on the size of the implant used, the location of the incision, and the characteristics of the subject's breast. In at least some instances, insertion of the implant into the tubular member 150 may extend the distal end 152 of the tubular member 150 deeper into the dissection tunnel such that the implant is shielded from a greater portion of the dissection tunnel during its transit to the implant pocket.

In at least some instances, the predetermined length 165 of the inner bore 115 of the tubular member 150 may be adjusted based on the desired depth of insertion into the dissection tunnel. In such instances, intraoperative measurements of the length of the dissection tunnel may be used to determine the predetermined length 165 of the inner bore 115 of the tubular member 150 necessary to shield the implant from at least a portion of the dissection tunnel. In such cases, the predetermined length 165 of the inner bore 115 may be adjusted or cut to a predetermined length 165 equal to or less than the measured length of the dissection tunnel.

Figure 13:
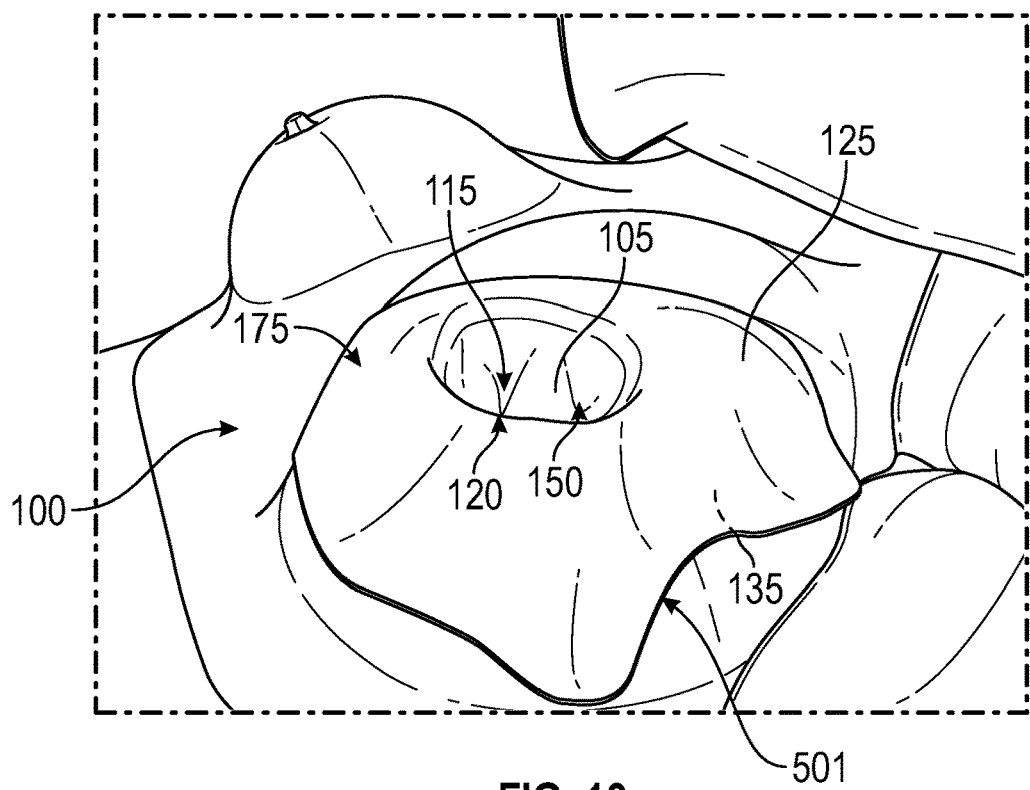
FIG. 13 is an illustration depicting engagement of the lower surface of the base of the implant shield with at least a portion of the skin adjacent to the incision, according to an exemplary embodiment of the present disclosure.

Once the tubular member 150 is sufficiently inserted into the dissection tunnel, the base 175 of apparatus 100 may be engaged with the surface of the skin 501 of the subject so that apparatus 100 may be anchored in place during insertion of the implant. As shown in FIG. 13, the lower surface 135 (opposite of upper surface 125) of base 175 is engaged with the skin 501 of the subject. As described above, the lower surface 135 of the base 175 may be engaged with the skin 501 of the subject by any number of techniques, including, but not limited to, frictional engagement by a textured surface or by wetting with a suitable liquid and by attaching to the skin 501 of the subject using an adhesive exposed by the removal of a removable backing. Once apparatus 100 is securely engaged with the skin 501 of the subject, aperture 120 and inner bore 115 substantially overlie at least a portion of the incision. In some instances, the distal end 152 of the tubular member 150 may be further positioned by inserting the insertion tool or retractors through the aperture 120 of the base 175 and within the inner bore 115 of tubular member 150. In this manner, the distal end 152 may be further inserted such that it is sufficiently received in a portion of either the dissection tunnel or the implant pocket.

Figure 14:
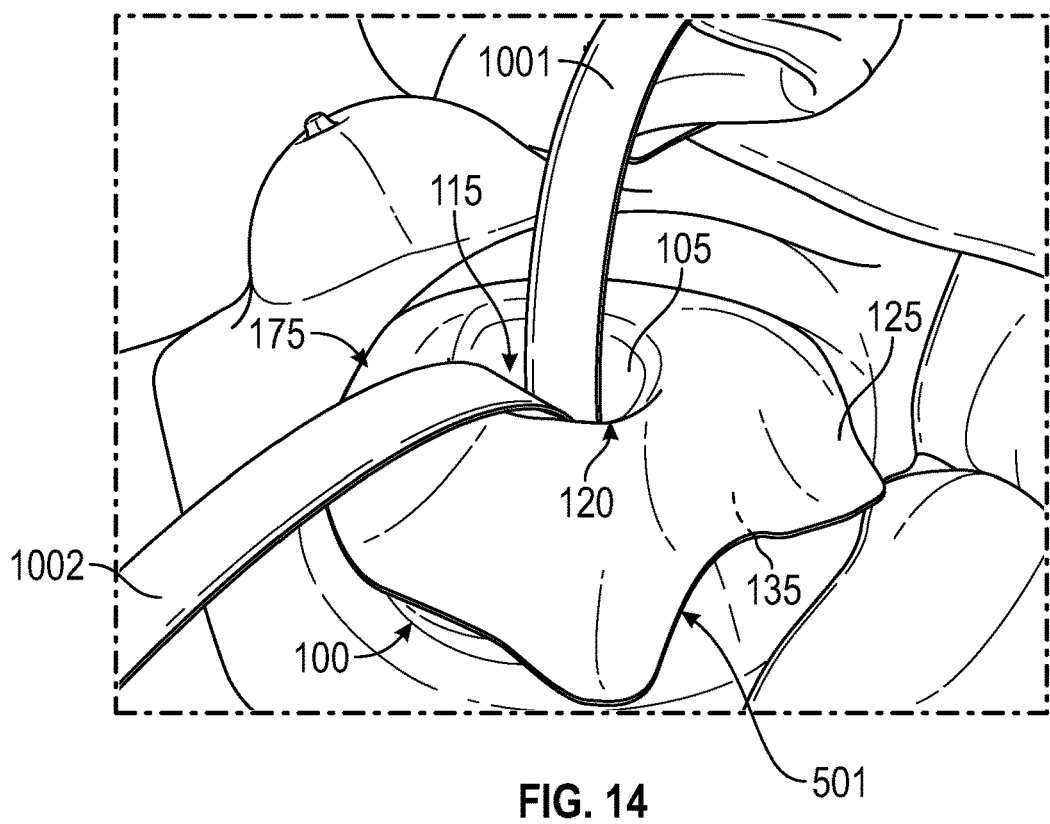
FIG. 14 is an illustration depicting opening of the inner bore of the tubular member and dissection tunnel using sterile retractors inserted into the inner bore of the implant shield with the implant shield in place to provide a shielded path for the implant to the implant pocket or dissection tunnel, according to an exemplary embodiment of the present disclosure.
Figure 15A:
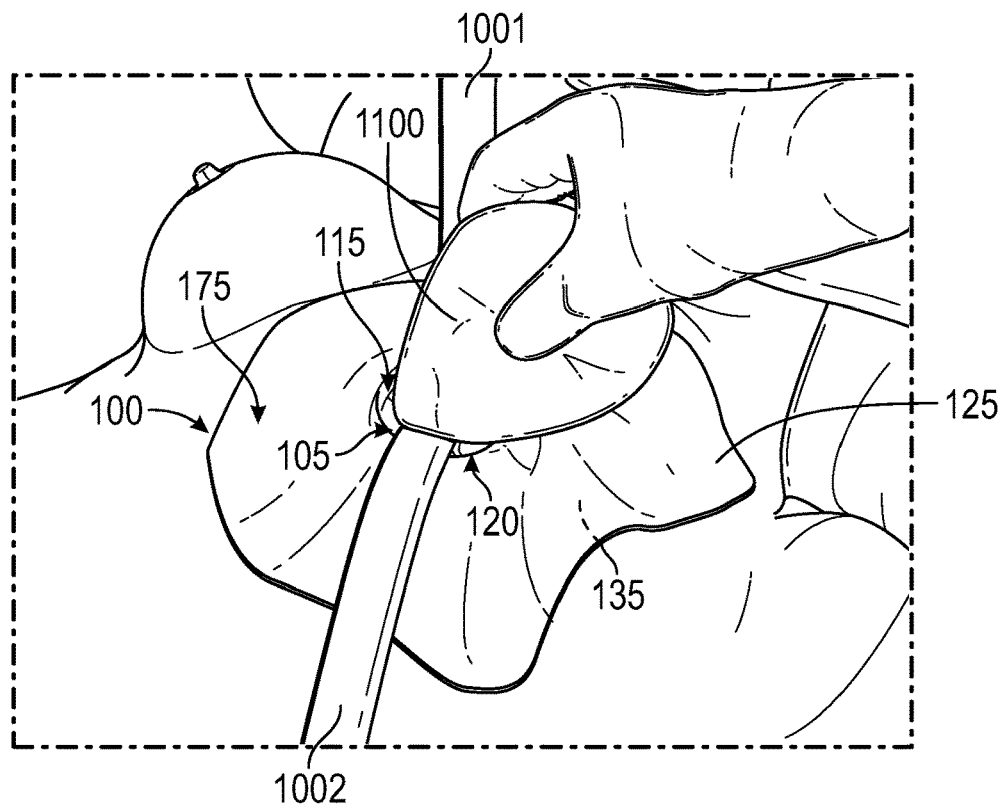
FIG. 15A is an illustration depicting insertion of the implant through the aperture of the base of the implant shield with the inner bore of the tubular member held open by sterile retractors inserted into the inner bore of the implant shield, according to an exemplary embodiment of the present disclosure.
Figure 15B:
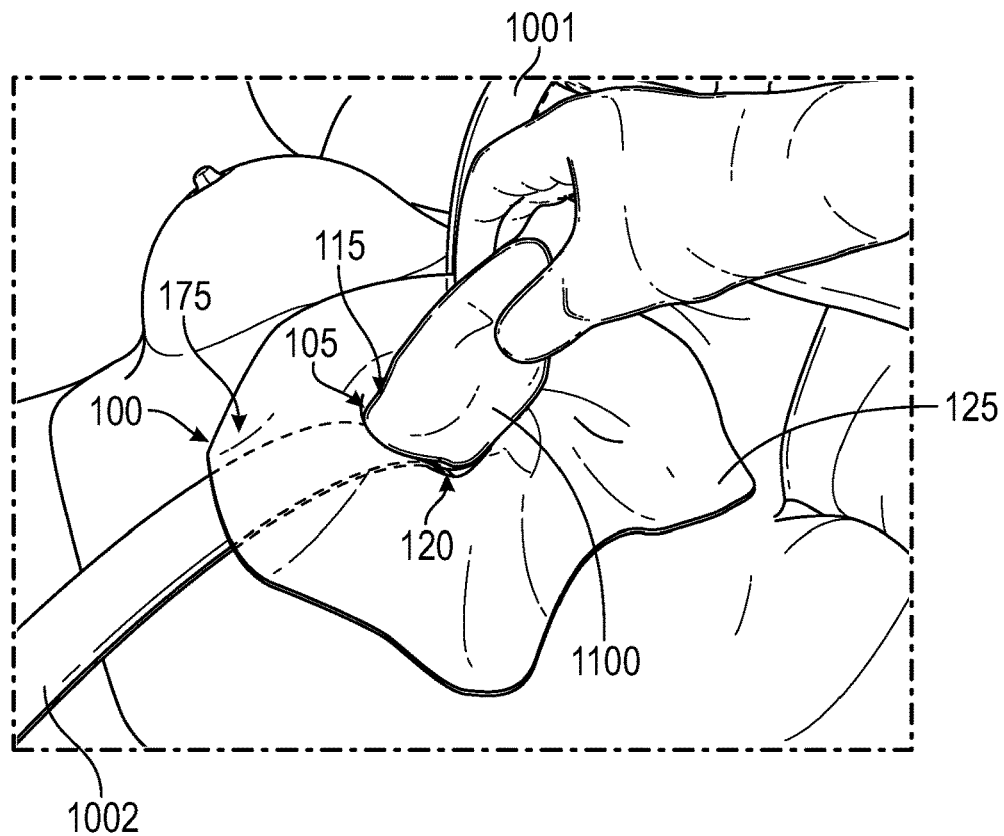
FIG. 15B is an illustration depicting delivery of the implant through the aperture of the base of the implant shield with the dissection tunnel held open by sterile retractors placed in the dissection tunnel outside the tubular member of the implant shield and between the walls of the dissection tunnel and the outer surface of the tubular member, according to an exemplary embodiment of the present disclosure.

In FIG. 14, the aperture 120 and the inner bore 115 of the tubular member 150 are opened up by sterile retractors 1001, 1002 so that the implant 1100 may be inserted into the aperture 120 and inner bore 115 of the apparatus 100, as shown in FIGS. 15A and 15B. As depicted in FIGS. 15A and 15B there are at least two methods by which the dissection tunnel may be opened sufficient for implant insertion into the breast. In FIG. 15A, the retractors 1001, 1002 are placed through aperture 120 and into inner bore 115 of the tubular member 150 in order to open the dissection tunnel and the inner bore 115 in order to facilitate insertion of implant 1100. FIG. 15B depicts an alternative method in which retractors 1001, 1002 are placed in the dissection tunnel outside the tubular member 150 and in between the walls of the dissection tunnel and the outer surface 110 of tubular member 150.

Figure 16:
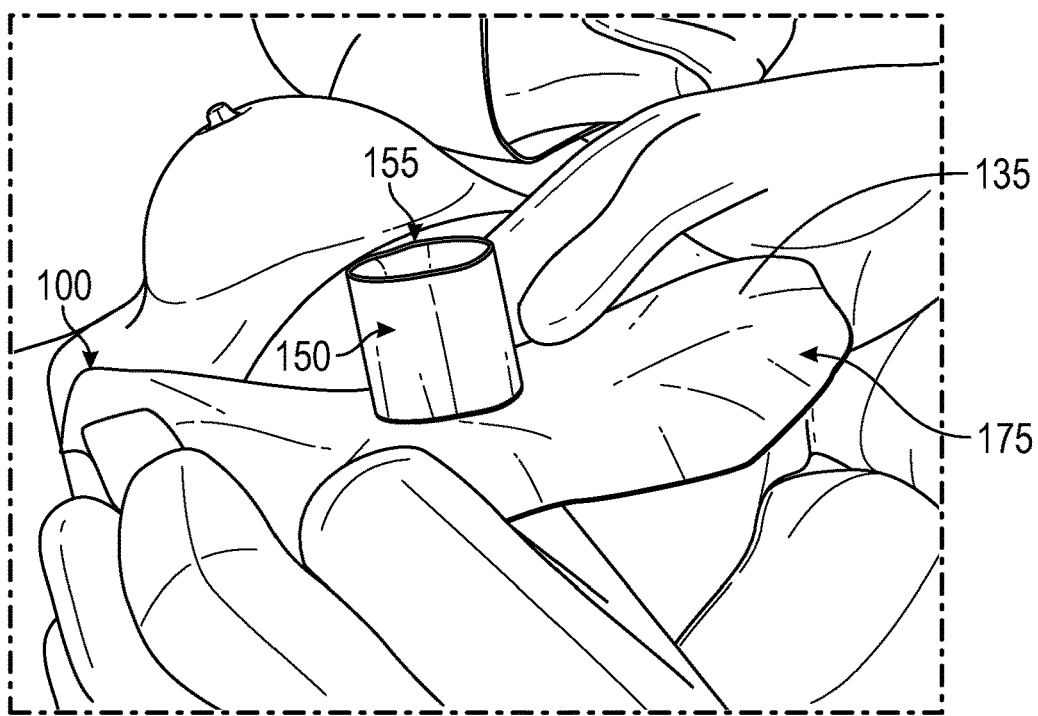
FIG. 16 is an illustration depicting disengagement of the lower surface of the base of the implant shield from the skin of the subject and removal of the tubular member from the dissection tunnel, according to an exemplary embodiment of the present disclosure.
Figure 17:
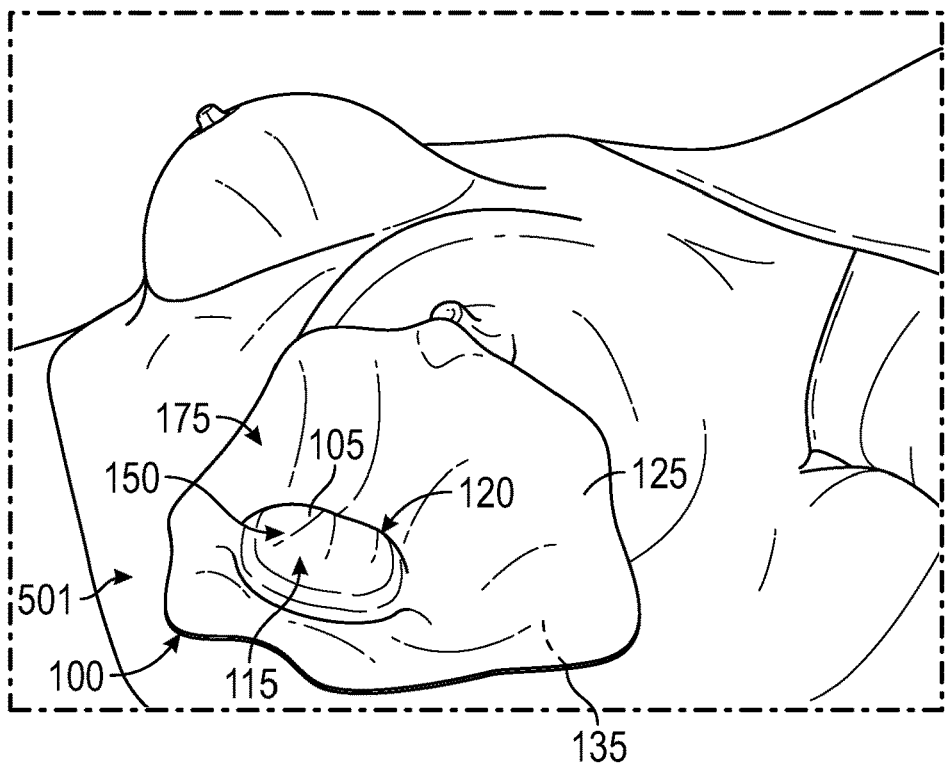
FIG. 17 is an illustration depicting insertion of the tubular member of the implant shield into an inframammary incision in skin of the subject, rather than the periareolar incision depicted in FIGS. 9-16, according to an exemplary embodiment of the present disclosure.

After the implant 1100 is inserted into the implant pocket while being shielded from the endogenous flora of the subject by biofilm protection implant shield apparatus 100, as described above, the base 175 of the apparatus 100 may be disengaged from the skin 501 of the subject and the tubular member 150 may be withdrawn from the dissection tunnel, as depicted in FIG. 16. While FIGS. 9-16 depict the use of periareolar incision carrying out the presently disclosed methods and techniques, any suitable incision may be used and still be within the spirit and scope of the present disclosure. For example, the incision may be a periareolar incision, an inframammary incision, an axillary incision, a vertical incision, and a transumbilical incision, or any other incision that may be made for the purpose of breast implant insertion. FIG. 17 depicts the non-limiting example of apparatus 100 used in the context of an inframammary incision in the skin of a subject in which the lower surface 135 (opposite of upper surface 125) of base 175 is engaged with the skin 501 of the subject and aperture 120 and inner bore 115 substantially overlie at least a portion of the inframammary incision.

Figure 18:
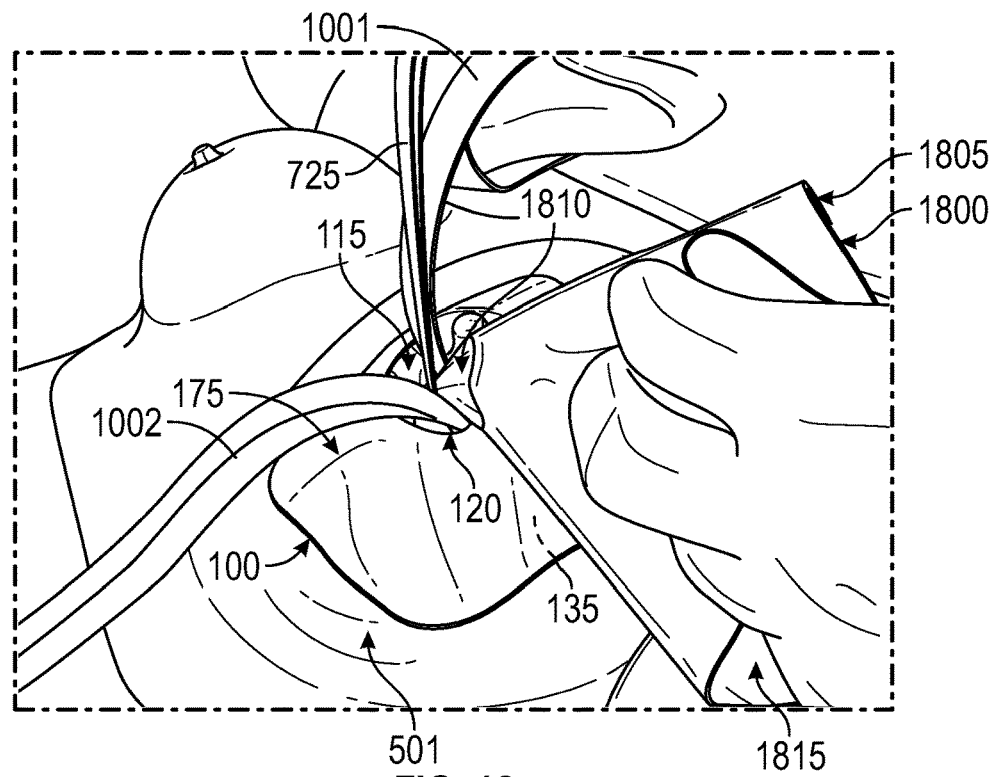
FIG. 18 is an illustration depicting insertion of the terminus of a conical sleeve through the aperture of the base and into the inner bore of the tubular member while the inner bore of the tubular member is held open using sterile retractors placed inside the inner bore of the tubular member, according to an exemplary embodiment of the present disclosure.
Figure 19:
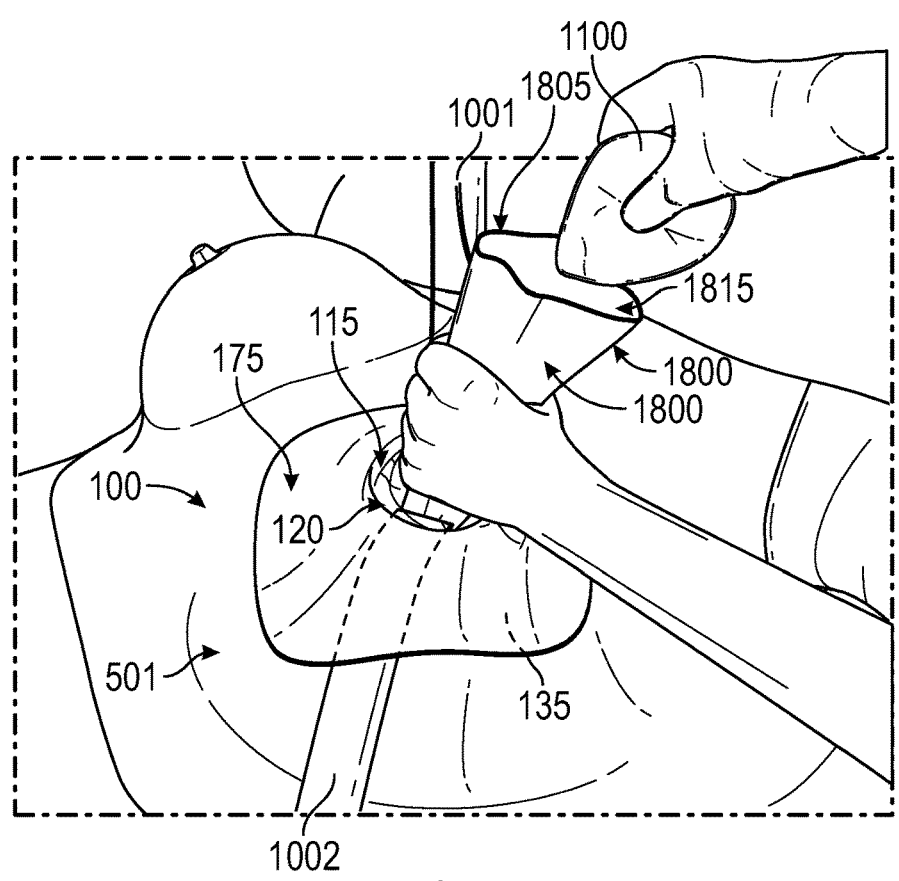
FIG. 19 is an illustration depicting insertion of the terminus of a conical sleeve through the aperture of the base and into the inner bore of the tubular member while the dissection tunnel is held open by sterile retractors placed in the dissection tunnel between the walls of the dissection tunnel and the outer surface of the tubular member of the implant shield, according to an exemplary embodiment of the present disclosure.
Figure 20:
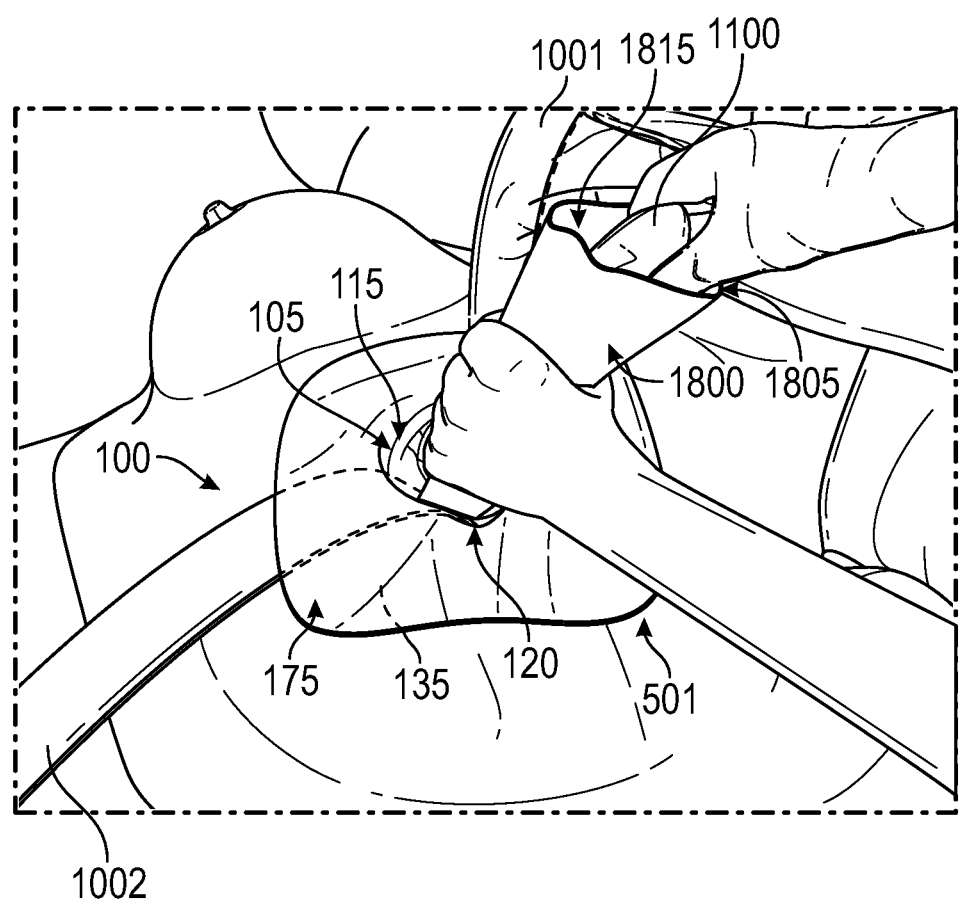
FIG. 20 is an illustration depicting insertion of an implant into a conical sleeve having a terminus disposed within the inner bore of the tubular member so that the implant may be delivered to the surgical pocket while being shielded by the implant shield.

FIGS. 18-20 depict an alternative embodiment for inserting the implant 1100 into the aperture 120 of the tubular member 150 of implant shield apparatus 100 once the lower surface 135 of the base 175 is engaged with the skin 501 of the subject. As depicted in FIGS. 18-20, a conical sleeve 1800 may be used to deliver the implant 1100 through aperture 120 and into inner bore 115 of tubular member 150. The conical sleeve 1800 may have an interior cavity 1815, a first terminus 1805, and a second terminus 1810, where the first terminus 1805 has a larger diameter than the second terminus 1810. The second terminus 1810 of conical sleeve 1800 may be inserted into the aperture 120 and inner bore 115 of the tubular member 150 of apparatus 100, as depicted in FIG. 18. The conical sleeve 1800 is operable to receive implant 1100 into its interior cavity 1815 via the first terminus 1805 and deliver the implant 1100 through the second terminus 1810 into the inner bore 115 of apparatus 100, as shown in FIGS. 19-20.

Figure 21:
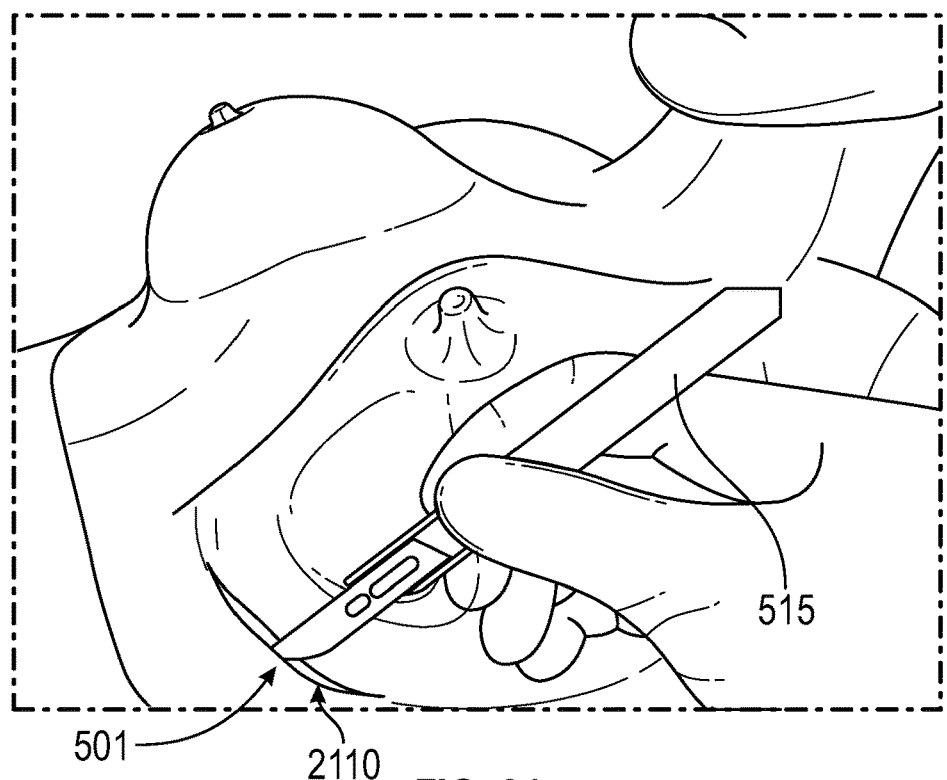
FIG. 21 is an illustration depicting the creation of an inframammary incision in the breast of a subject; according to an exemplary embodiment of the present disclosure.
Figure 22:
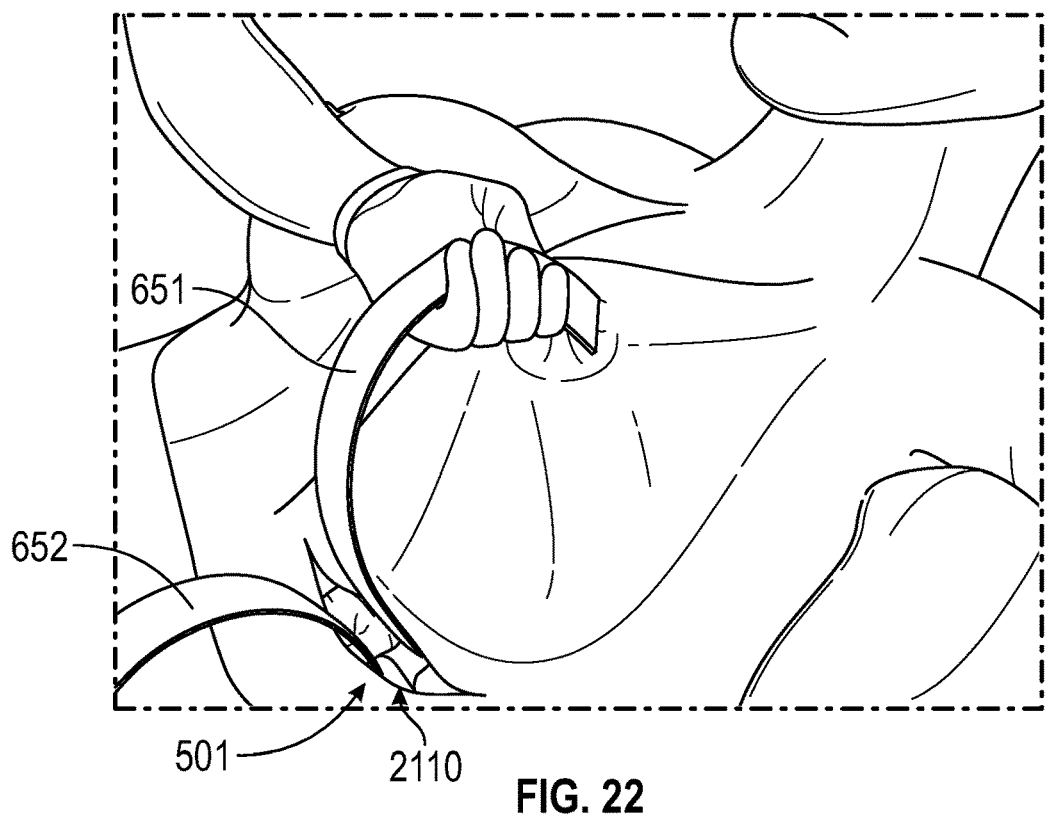
FIG. 22 is an illustration depicting the opening of the inframammary incision using two retractors, according to an exemplary embodiment of the present disclosure.
Figure 23:
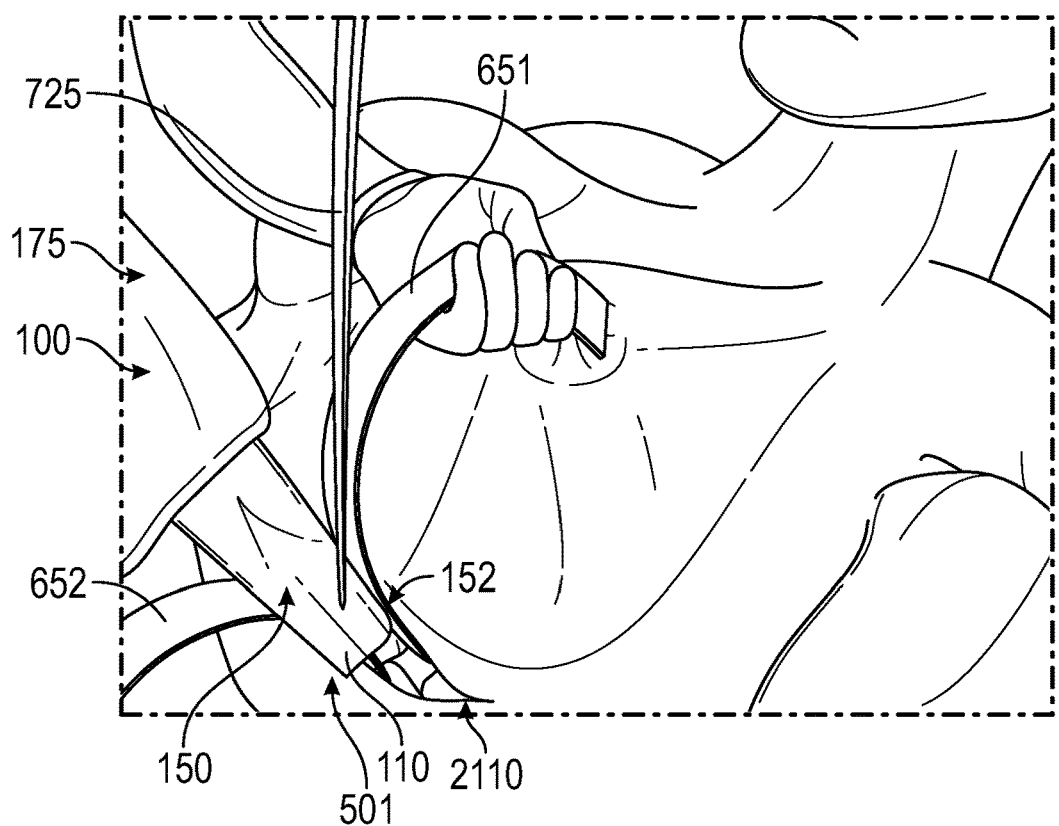
FIG. 23 is an illustration depicting insertion of the distal end of the tubular member of the implant shield into the dissection tunnel connecting the inframammary incision to the surgically-created implant pocket, according to an exemplary embodiment of the present disclosure.
Figure 24:
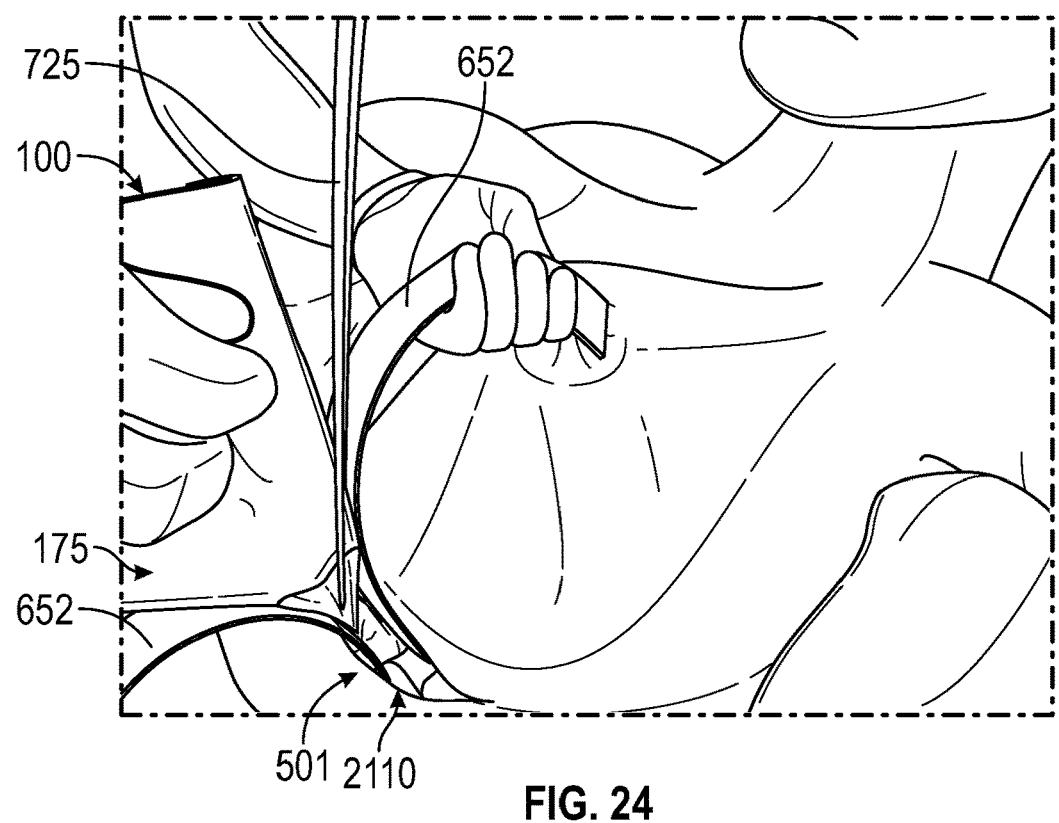
FIG. 24 is an illustration depicting further insertion of the tubular member into the dissection tunnel, according to an exemplary embodiment of the present disclosure.

FIGS. 21-28 illustrate methods for the use of the presently disclosed biofilm protection implant shield apparatus 100 in the case of inframammary incision and implant insertion. As depicted in FIG. 21, an inframammary incision 2110 in the skin 501 of the subject is created by scalpel 515. FIG. 22 depicts the use of retractors 651, 652 to open the inframammary incision 2110 and to facilitate full surgical dissection of the implant pocket and the dissection tunnel connecting the implant pocket to the incision. As depicted in FIG. 23, the inframammary incision 2110 and the dissection tunnel are further opened using retractors 651, 652 to facilitate insertion of the tubular member 150 of apparatus 100. In particular, the distal end 152 of the tubular member 150 is inserted through the incision 2110 and into the dissection tunnel using any suitable sterile insertion tool, such as forceps 725. As shown in FIG. 24, the tubular member 150 is further inserted into the dissection tunnel such that the distal end 152 of the tubular member 150 is received in at least a portion of the dissection tunnel or the implant pocket.

Figure 25:
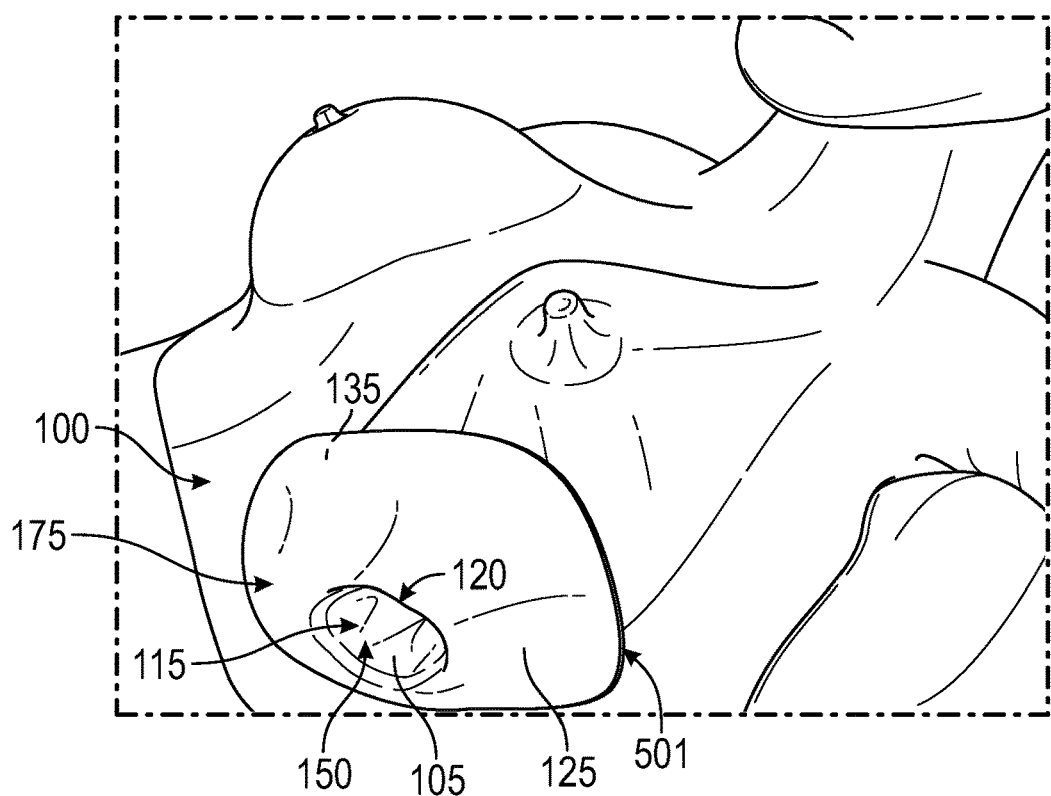
FIG. 25 is an illustration depicting engagement of the lower surface of the base of the implant shield with at least a portion of the skin adjacent to the incision, according to an exemplary embodiment of the present disclosure.

Once the tubular member 150 is sufficiently inserted into the dissection tunnel, the base 175 of apparatus 100 may be engaged with the surface of the skin 501 of the subject so that apparatus 100 may be anchored in place during insertion of the implant. As shown in FIG. 25, the lower surface 135 (opposite of upper surface 125) of base 175 is engaged with the skin 501 of the subject. As described above, the lower surface 135 of the base 175 may be engaged with the skin 501 of the subject by any number of techniques, including, but not limited to, frictional engagement by a textured surface or by wetting with a suitable liquid and by attaching to the skin 501 of the subject using an adhesive exposed by the removal of a removable backing. Once apparatus 100 is securely engaged with the skin 501 of the subject, aperture 120 and inner bore 115 substantially overlie at least a portion of the incision. In some instances, the distal end 152 of the tubular member 150 may be further positioned by inserting the insertion tool or retractors through the aperture 120 of the base 175 and within the inner bore 115 of tubular member 150. In this manner, the distal end 152 may be further inserted such that it is sufficiently received in a portion of either the dissection tunnel or the implant pocket.

Figure 26:
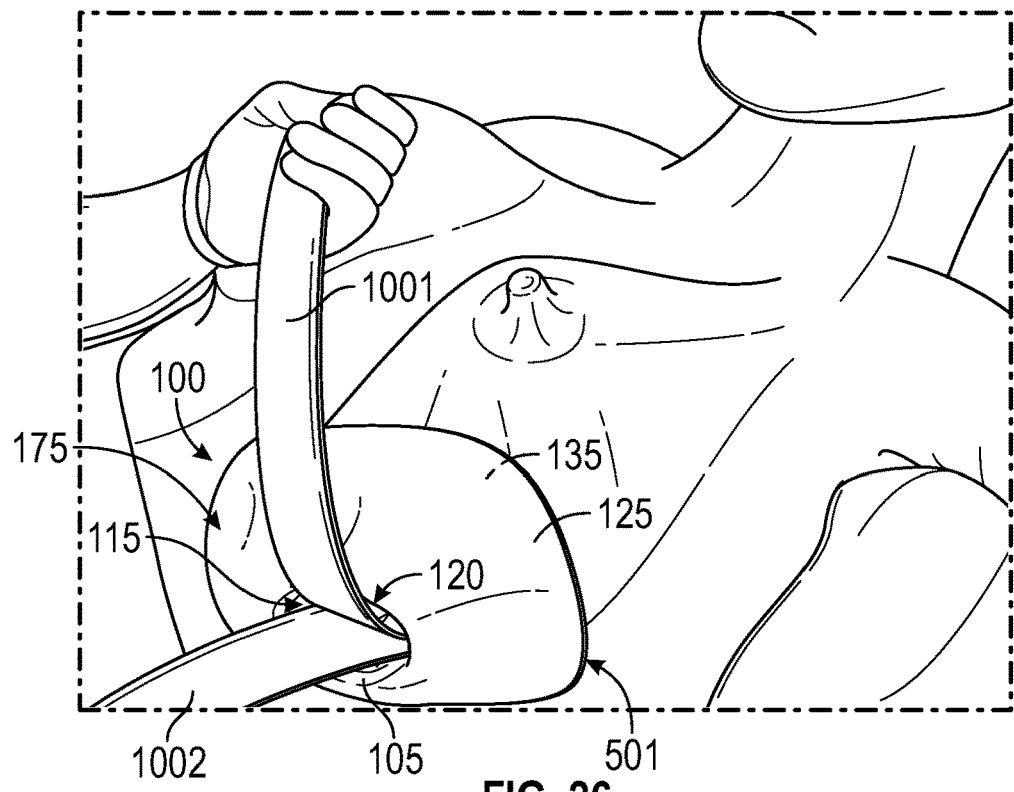
FIG. 26 is an illustration depicting opening of the inner bore of the tubular member and dissection tunnel using sterile retractors inserted into the inner bore of the implant shield with the implant shield in place to provide a shielded path for the implant to the implant pocket or dissection tunnel, according to an exemplary embodiment of the present disclosure.
Figure 27A:
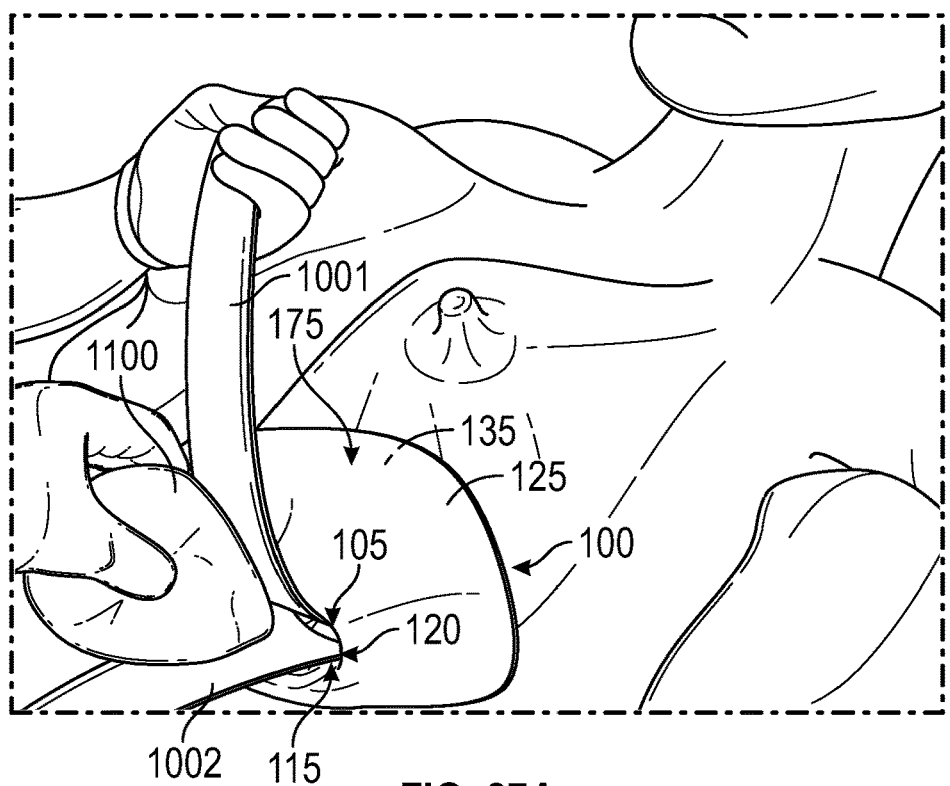
FIG. 27A is an illustration depicting insertion of the implant through the aperture of the base of the implant shield with the inner bore of the tubular member held open by sterile retractors inserted into the inner bore of the implant shield, according to an exemplary embodiment of the present disclosure.
Figure 27B:
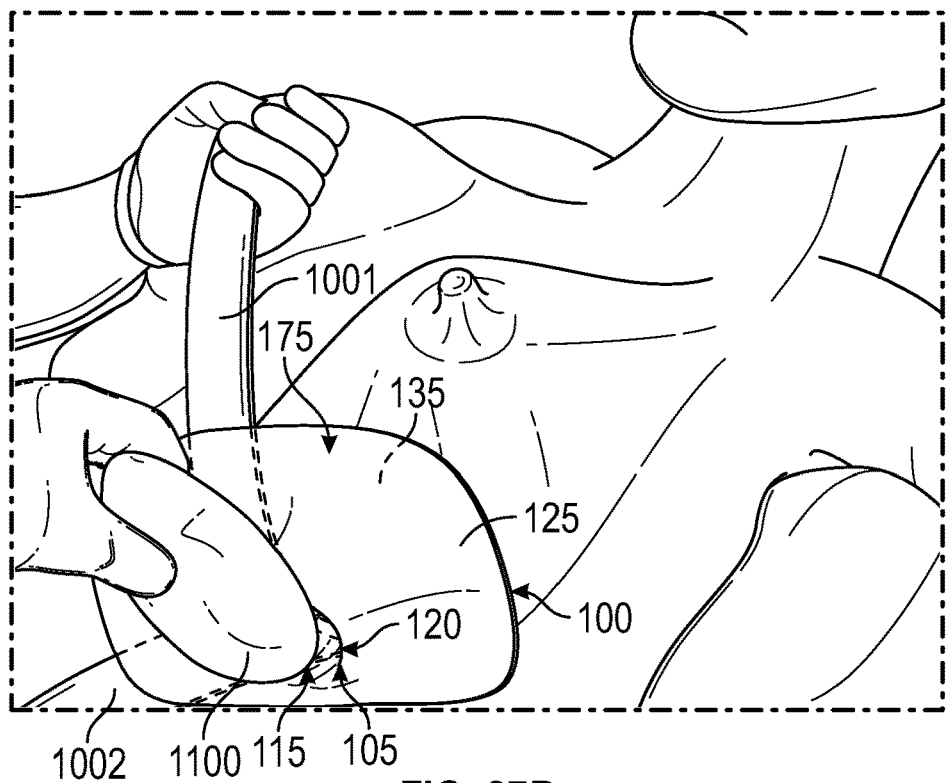
FIG. 27B is an illustration depicting delivery of the implant through the aperture of the base of the implant shield with the dissection tunnel held open by sterile retractors placed in the dissection tunnel outside the tubular member of the implant shield and between the walls of the dissection tunnel and the outer surface of the tubular member, according to an exemplary embodiment of the present disclosure.

In FIG. 26, the aperture 120 and the inner bore 115 of the tubular member 150 are opened up by sterile retractors 1001, 1002 so that the implant 1100 may be inserted into the aperture 120 and inner bore 115 of the apparatus 100, as shown in FIGS. 27A and 27B. As depicted in FIGS. 27A and 27B there are at least two methods by which the dissection tunnel may be opened sufficient for implant insertion into the breast. In FIG. 27A, the retractors 1001, 1002 are placed through aperture 120 and into inner bore 115 of the tubular member 150 in order to open the dissection tunnel and the inner bore 115 in order to facilitate insertion of implant 1100. FIG. 27B depicts an alternative method in which retractors 1001, 1002 are placed in the dissection tunnel outside the tubular member 150 and in between the walls of the dissection tunnel and the outer surface 110 of tubular member 150.

Figure 28:
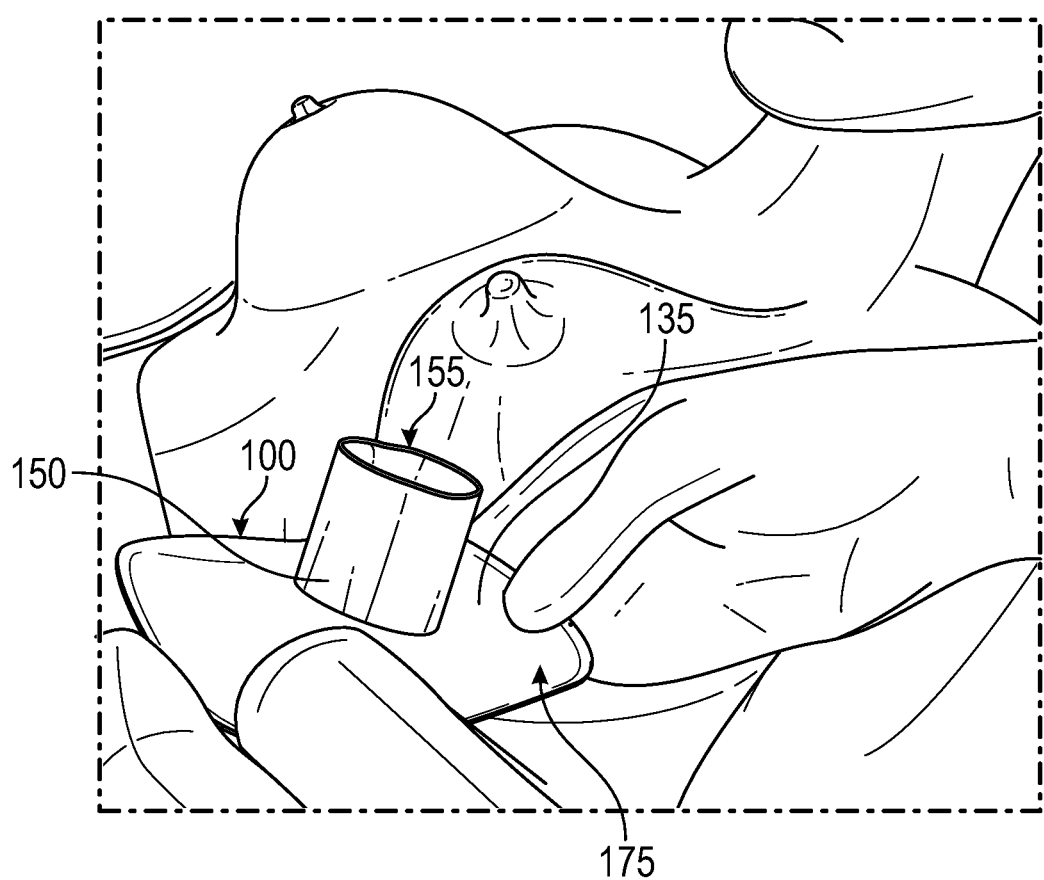
FIG. 28 is an illustration depicting disengagement of the lower surface of the base of the implant shield from the skin of the subject and removal of the tubular member from the dissection tunnel, according to an exemplary embodiment of the present disclosure.

After the implant 1100 is inserted into the implant pocket while being shielded from the endogenous flora of the subject by biofilm protection implant shield apparatus 100, as described above, the base 175 of the apparatus 100 may be disengaged from the skin 501 of the subject and the tubular member 150 may be withdrawn from the dissection tunnel, as depicted in FIG. 28.

Figure 29:
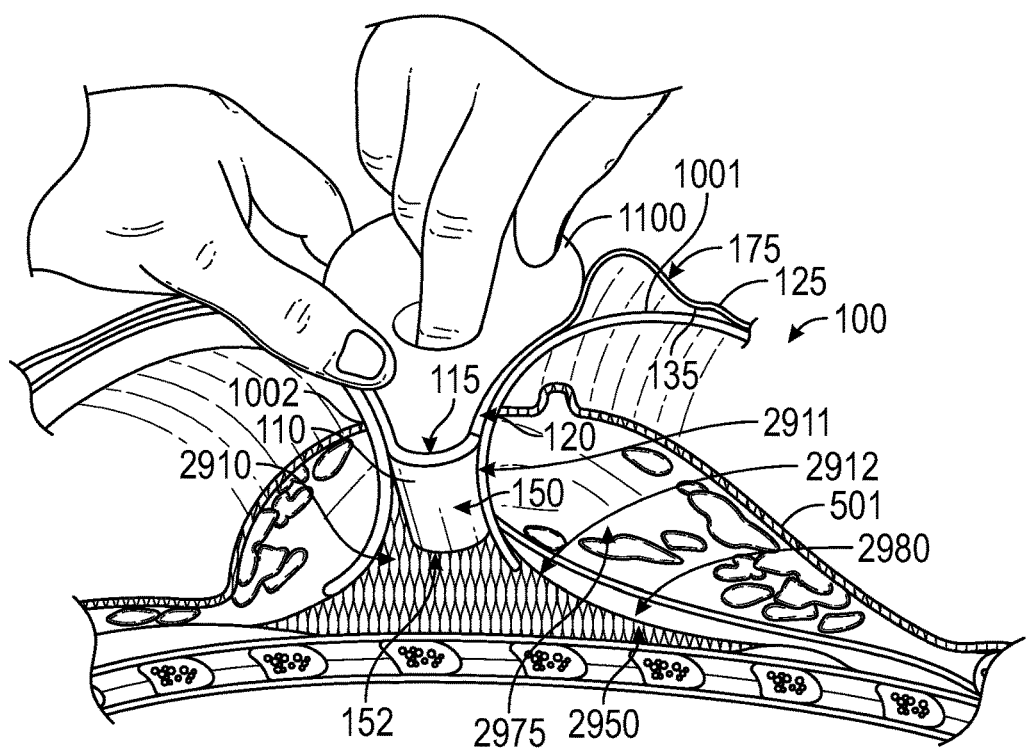
FIG. 29 is a partial cross-sectional view of the periareolar insertion of an implant through the aperture of the base of an implant shield engaged with the skin of a subject and through the tubular member of the implant shield towards the implant pocket with the retractors holding open the dissection tunnel by being placed outside the tubular member, according to an exemplary embodiment of the present disclosure.

FIGS. 29-32 are partial cross-sectional views illustrating methods for the use of the presently disclosed biofilm protection implant shield apparatus 100. In particular, FIG. 29 depicts periareolar insertion of an implant 1100 through aperture 120 of base 175 of the implant shield apparatus 100. As depicted in FIG. 29, the lower surface 135 of base 175 is engaged with the skin 501 of the subject while the dissection tunnel 2910 is held open by retractors 1001, 1002 placed outside the tubular member 150 and between the outer surface 110 of the tubular member 150 and the walls 2915 of dissection tunnel 2910. As shown in FIG. 29, insertion of the implant 1100 through aperture 120 and into the inner bore 115 of tubular member 150 provides for shielding of the implant 1100 from contamination by the breast tissue 2975 comprising the upper dissection tunnel 2911 and the endogenous flora of the subject during transit through the dissection tunnel 2910 to the implant pocket 2950. The lower dissection tunnel 2912 is formed by pectoral muscle tissue 2980, as shown by FIG. 29.

Figure 30:
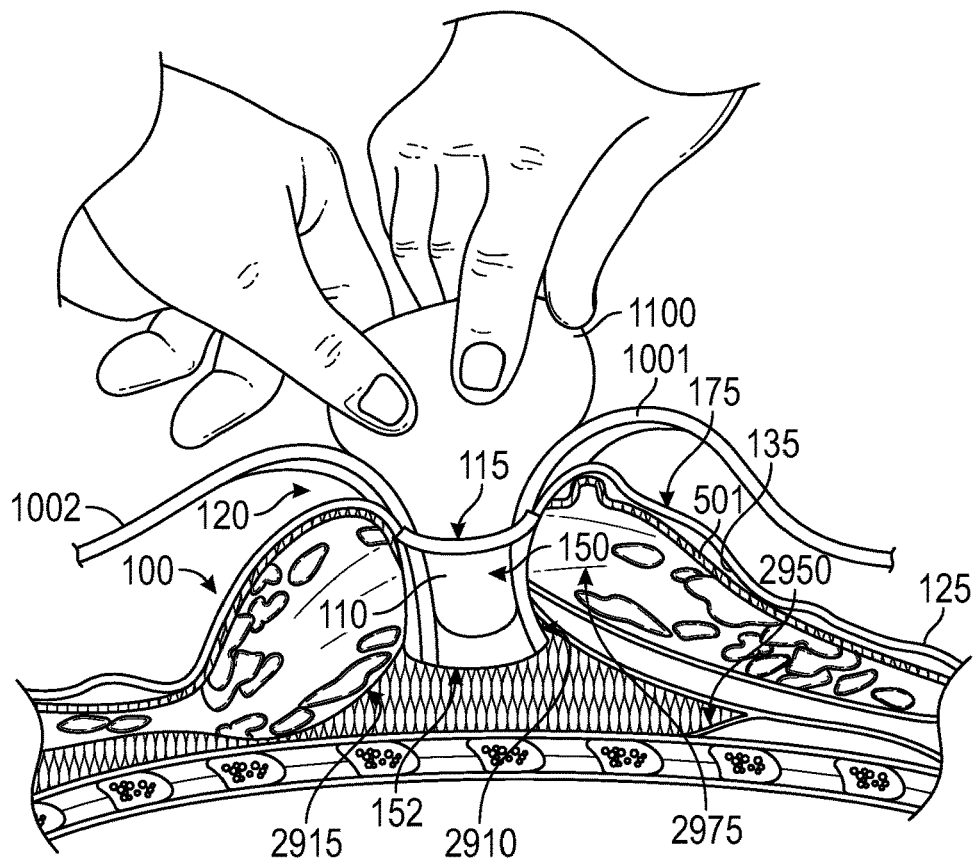
FIG. 30 is a partial cross-sectional view of the periareolar insertion of an implant through the aperture of the base of an implant shield engaged with the skin of a subject and through the tubular member of the implant shield towards the implant pocket with the retractors holding open the tubular member by being placed inside the inner bore of the tubular member, according to an exemplary embodiment of the present disclosure.

FIG. 30 depicts a similar periareolar insertion as shown in FIG. 29, except that retractors 1101, 1102, are placed inside of the inner bore 115 of tubular member 150 so as to hold open the inner bore 115 during insertion of the implant 1100 through aperture 120 of tubular member 150. As depicted in FIG. 30, tubular member 150 having outer surface 110 shields the implant 1100 from contamination by the breast tissue 2975 and the endogenous flora of the subject during transit of the implant 1100 through the dissection tunnel 2910 to the implant pocket 2950.

Figure 31:
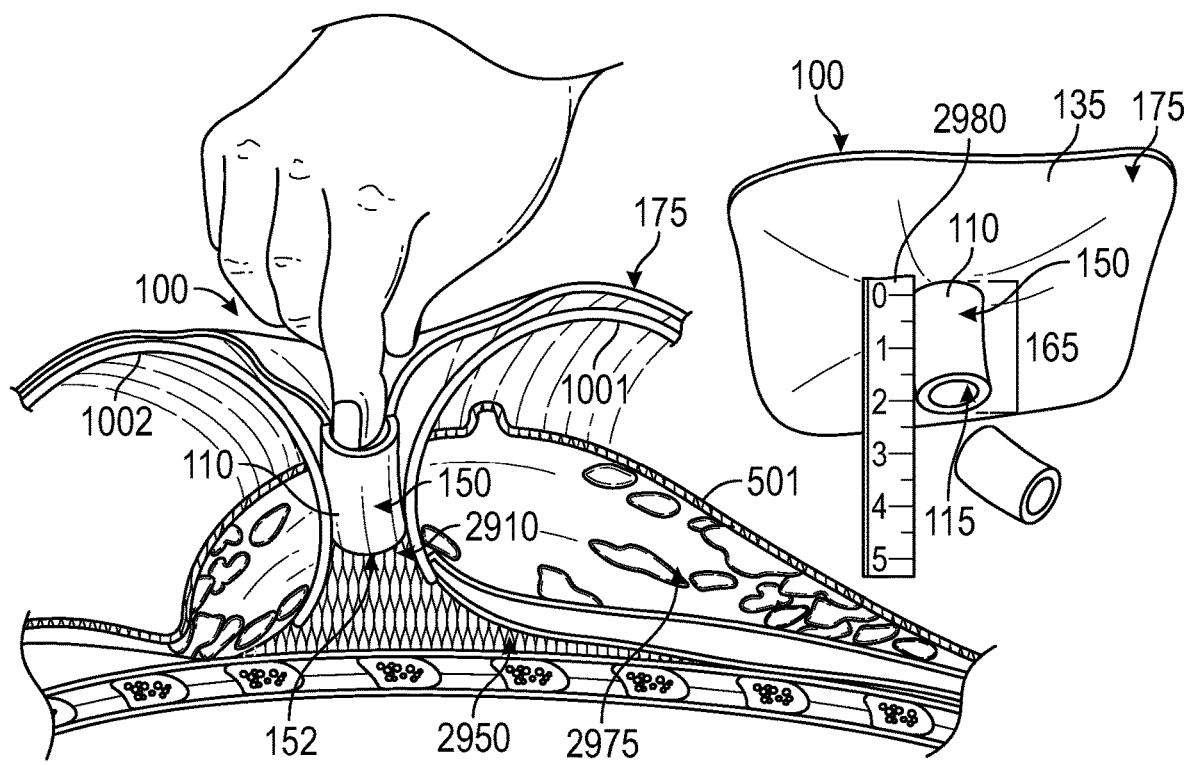
FIG. 31 is a partial cross-sectional view of the periareolar insertion of the implant shield into a distal portion of the dissection tunnel after adjusting the predetermined length of the inner bore of the tubular member based on a measured length of the dissection tunnel connecting the implant pocket to the periareolar incision on the skin of the subject, according to an exemplary embodiment of the present disclosure.

FIG. 31 depicts insertion of the distal end 152 of tubular member 150 into the dissection tunnel 2910 connecting a periareolar incision to the implant pocket 2950. As shown in FIG. 31, the distal end 152 of the tubular member 150 is generally inserted into the dissection tunnel to a depth greater than 1 cm below the incision so as to sufficiently shield the implant 1100 during insertion into the dissection tunnel 2910 and implant pocket 2950. The tubular member 150 and inner bore 115 of tubular member 150 have a predetermined length 165 that may be adjusted (e.g., from about 1.5 cm to about 10 cm) based on the length of the dissection tunnel 2910, the desired depth of insertion into the dissection tunnel 2910, the size of the implant used, the location of the incision, and the characteristics of the subject's breast.

Figure 32:
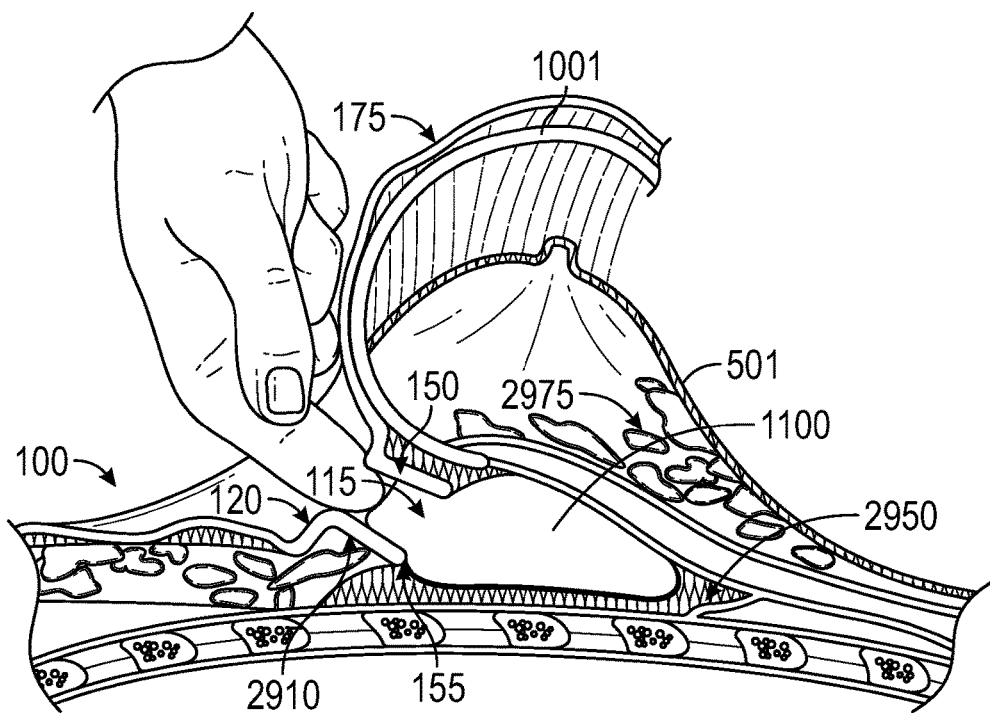
FIG. 32 is a partial cross-sectional view of the inframammary insertion of an implant through the aperture of the base of an implant shield engaged with the skin of a subject through the tubular member of the implant shield into a distal portion of the dissection tunnel and the implant pocket, according to an exemplary embodiment of the present disclosure.

FIG. 32 depicts a partial cross-sectional view of the inframammary insertion of an implant 1100 through the aperture 120 of the base 175 of an implant shield 100 engaged with the skin 501 of a subject. As depicted in FIG. 32, the implant 1100 transits the inner bore 115 of tubular member 150 which shields the implant 1100 from at least a portion of the dissection tunnel 2910 as the implant 1100 exits the aperture 155 of the tubular member 150 and enters the implant pocket 2950.

Statements of the Present Disclosure

Numerous examples are provided herein to enhance understanding of the present disclosure. A specific set of statements are provided as follows.

Statement 1: An apparatus for inserting an implant into a surgically-created implant pocket in a subject, the apparatus comprising: a base having an upper surface and a lower surface, the base having an aperture formed therein and extending through the upper surface and the lower surface; and a tubular member coupled with the base, the tubular member having an inner bore extending longitudinally between a proximal end and a distal end, the inner bore extending a predetermined length away from the lower surface of the base; wherein the proximal end of the tubular member is coupled with the base and the inner bore is substantially aligned with the aperture formed in the base; and wherein the inner bore is operable to receive the implant therethrough and has a substantially uniform cross-sectional width over the predetermined length.

Statement 2: The apparatus according to Statement 1, wherein the inner bore has a longitudinal axis therethrough, the tubular member extending along the longitudinal axis.

Statement 3: The apparatus according to Statement 1 or Statement 2, wherein the inner bore extends longitudinally along a longitudinal axis a predetermined length away from the lower surface of the base.

Statement 4: The apparatus according to Statement 2 or Statement 3, wherein the longitudinal axis extends substantially perpendicular to the base.

Statement 5: The apparatus according to Statement 1, wherein the tubular member extends longitudinally along a longitudinal axis substantially perpendicular to the base.

Statement 6: The apparatus according to any one of the preceding Statements 1-5, wherein the tubular member extends substantially orthogonally from the base.

Statement 7: The apparatus according to any one of the preceding Statements 1-6, wherein the base extends away from the tubular member in a direction substantially perpendicular to the longitudinal axis.

Statement 8: The apparatus according to any one of the preceding Statements 1-7, wherein the tubular member is substantially cylindrical in cross-sectional shape.

Statement 9: The apparatus according to any one of the preceding Statements 1-7, wherein the tubular member is elliptical in cross-sectional shape.

Statement 10: The apparatus according to any one of the preceding Statements 1-9, wherein at least a portion of the inner bore of tubular member extends a second predetermined length above the upper surface of the base.

Statement 11: The apparatus according to any one of the preceding Statements 1-10, wherein the lower surface of the base is operable to engage with a skin of the subject.

Statement 12: The apparatus according to any one of the preceding Statements 1-11, wherein the lower surface of the base is operable to engage a skin of the subject adjacent to an incision, wherein the inner bore of tubular member substantially overlies at least a portion of the incision.

Statement 13: The apparatus according to any one of the preceding Statements 1-12, wherein the lower surface of the base is operable to engage with a skin of the subject so as to resist movement of the base with respect to the skin when engaged with the skin.

Statement 14: The apparatus according to any one of the preceding Statements 1-13, wherein the lower surface is operable to frictionally engage the skin of a subject, wherein the frictional engagement resists movement of the base relative to the skin.

Statement 15: The apparatus according to any one of the preceding Statements 1-14, wherein the lower surface comprises a textured surface.

Statement 16: The apparatus according to any one of the preceding Statements 1-15, wherein the lower surface comprises a surface operable to frictionally engage the skin of a subject once wetted.

Statement 17: The apparatus according to any one of the preceding Statements 1-15, wherein a fluid is disposed on one of the lower surface and/or the skin of the patient, the fluid operable to form a frictional engagement between the lower surface and the skin.

Statement 18: The apparatus according to any one of the preceding Statements 1-15, wherein an adhesive is disposed on the lower surface.

Statement 19: The apparatus according to Statement 18, wherein the lower surface further comprises a removable backing, the removable backing operable to expose the adhesive.

Statement 20: The apparatus according to any one of the preceding Statements 1-19, wherein the predetermined length is determined based on a distance between an incision in the skin of a patient and a surgically-created implant pocket formed below the skin.

Statement 21: The apparatus according to any one of the preceding Statements 1-20, wherein the predetermined length between the proximal end and the distal end extends the inner bore operably to deliver an implant subdermally through the aperture and inner bore and into the surgically-created implant pocket when the lower surface of base is adjacently engaged with the skin of a patient and the distal end is received into at least a portion of the implant pocket.

Statement 22: The apparatus according to any one of the preceding Statements 1-21, wherein the proximal end of tubular member is operable to receive an implant therethrough.

Statement 23: The apparatus according to Statement 22, wherein the tubular member is further operable to deliver the implant subdermally to the implant pocket through the predetermined length of inner bore of the tubular member.

Statement 24: The apparatus according to any one of the preceding Statements 1-23, wherein the distal end of tubular member is operable to be inserted into an incision in the skin of the subject, and the tubular member is operable to be extended the predetermined length such that the distal end is received into at least a portion of the surgically-created implant pocket.

Statement 25: The apparatus according to Statement 24, wherein tubular member extends along at least a portion of a dissection tunnel formed between the incision and the implant pocket.

Statement 26: The apparatus according to Statement 24 or Statement 25, wherein the tubular member is operable to deliver the implant to the implant pocket through a dissection tunnel connecting the incision to the implant pocket without the implant contacting the dissection tunnel.

Statement 27: The apparatus according to any one of the preceding Statements 1-26, wherein the tubular member comprises an inner surface and an outer surface, the inner surface defining the inner bore of tubular member.

Statement 28: The apparatus according to any one of the preceding Statements 1-27, wherein the tubular member and the base are formed from the same material.

Statement 29: The apparatus according to any one of the preceding Statements 1-28, wherein the tubular member and base are formed from a flexible material.

Statement 30: The apparatus according to Statement 29, wherein the flexible material is resistant to stretching.

Statement 31: The apparatus according to Statement 29, wherein the flexible material is capable of stretching.

Statement 32: The apparatus according to Statement 29, wherein the flexible material is operable to stretch when an implant is inserted and/or physically manipulated through the longitudinal length of the inner bore of the tubular member.

Statement 33: The apparatus according to any one of Statements 29-32, wherein the flexible material is selected from the group consisting of plastic-containing fabrics, polymers, plastics, mylar, vinyls, polyvinyl chloride, ethylene and alpha-olefin copolymers, silicone, solid silicone, silicone rubber, and any combination thereof.

Statement 34: The apparatus according to any one of the preceding Statements 1-33, wherein the tubular member and the base are integrally formed.

Statement 35: The apparatus according to any one of the preceding Statements 1-34, wherein the inner bore of tubular member is not tapered along the predetermined length.

Statement 36: The apparatus according to any one of the preceding Statements 1-35, wherein the implant is selected from the group consisting of a breast implant, a pre-filled breast implant, a pre-filled saline breast implant, a pre-filled silicone breast implant, an un-filled breast implant, a saline breast implant, a silicone breast implant, a textured breast implant, a smooth breast implant, a highly cohesive silicone gel breast implant, an oil-filled breast implant, and an un-filled saline breast implant.

Statement 37: The apparatus according to any one of the preceding Statements 1-36, wherein the inner bore comprises a lubricant.

Statement 38: The apparatus according to any one of the preceding Statements 1-36, wherein the inner surface of the tubular member comprises a lubricant.

Statement 39: The apparatus according to any one of the preceding Statements 1-36, wherein the outer surface of the tubular member comprises a lubricant.

Statement 40: The apparatus according to any one of the preceding Statements 37-39, wherein the lubricant is a sterile lubricant selected from the group consisting of a surgical lubricant, a water-based lubricating jelly, a dry lubricant, a powdered lubricant, a moisture-activated lubricant, and any combination thereof.

Statement 41: The apparatus according to any one of the preceding Statements 1-40, wherein the inner bore comprises a lubricating coating or a friction-reducing coating.

Statement 42: The apparatus according to any one of the preceding Statements 1-36, wherein the inner surface of the tubular member comprises a lubricating coating or a friction-reducing coating.

Statement 43: The apparatus according to any one of the preceding Statements 1-36, wherein the outer surface of the tubular member comprises a lubricating coating or a friction-reducing coating.

Statement 44: The apparatus according to any one of the preceding Statements 1-43, wherein the predetermined length of the inner bore is equal to or less than a measured length of the dissection tunnel.

Statement 45: The apparatus according to any one of the preceding Statements 1-43, wherein the predetermined length of the inner bore is equal to or less than a measured length of the upper dissection tunnel.

Statement 46: The apparatus according to any one of the preceding Statements 1-45, wherein the predetermined length of the inner bore is greater than 1 cm.

Statement 47: The apparatus according to any one of the preceding Statements 1-45, wherein the predetermined length of the inner bore is greater than 1.5 cm.

Statement 48: The apparatus according to any one of the preceding Statements 1-45, wherein the predetermined length of the inner bore is greater than 2 cm.

Statement 49: The apparatus according to any one of the preceding Statements 1-45, wherein the predetermined length of the inner bore is greater than 2.5 cm.

Statement 50: The apparatus according to any one of the preceding Statements 1-45, wherein the predetermined length of the inner bore is greater than 3 cm.

Statement 51: The apparatus according to any one of the preceding Statements 1-45, wherein the predetermined length of the inner bore is greater than 3.5 cm.

Statement 52: The apparatus according to any one of the preceding Statements 1-45, wherein the predetermined length of the inner bore is greater than 4 cm.

Statement 53: The apparatus according to any one of the preceding Statements 1-45, wherein the predetermined length of the inner bore is greater than 4.5 cm.

Statement 54: The apparatus according to any one of the preceding Statements 1-45, wherein the predetermined length of the inner bore is greater than 5 cm.

Statement 55: The apparatus according to any one of the preceding Statements 1-45, wherein the predetermined length of the inner bore is from about 1.5 cm to about 10 cm.

Statement 56: The apparatus according to any one of the preceding Statements 1-45, wherein the predetermined length of the inner bore is from about 1.5 cm to about 5 cm or from about 3 cm to about 8 cm.

Statement 57: The apparatus according to any one of the preceding Statements 1-56, wherein the distal end of the tubular member comprises a second aperture that is substantially aligned with the inner bore and the aperture of the base when the tubular member is extended.

Statement 58: The apparatus according to any one of the preceding Statements 1-57, wherein the distal end has substantially the same cross-sectional width as the cross-sectional width of the proximal end.

Statement 59: The apparatus according to any one of the preceding Statements 1-58, wherein the cross-sectional width of the inner bore at the distal end of the tubular member is substantially the same as the cross-sectional width of the inner bore at the proximal end of the tubular member.

Statement 60: The apparatus according to any one of the preceding Statements 57-59, wherein the second aperture at the distal end of the tubular member has substantially the same cross-sectional width as the cross-sectional width of the aperture in the base.

Statement 61: The apparatus according to any one of the preceding Statements 1-60, wherein the distal end and the proximal end of the inner bore have the same cross-sectional profile, wherein the cross-sectional profile is selected from the group consisting of circular, elliptical, and oval.

Statement 62: The apparatus according to any one of the preceding Statements 1-60, wherein the distal end and the proximal end of the inner bore have a different cross-sectional profile, wherein the cross-sectional profile is selected from the group consisting of circular, elliptical, and oval.

Statement 63: The apparatus according to Statement 62, wherein the distal end and the proximal end of the inner bore have substantially the same cross-sectional width.

Statement 64: An apparatus for inserting an implant into a surgically-created implant pocket in a subject, the apparatus comprising: a base having an upper surface and a lower surface; and a tubular member extending through the base, the tubular member having an inner bore, a proximal end and a distal end, the inner bore extending longitudinally a predetermined length away from the lower surface of the base and between the proximal end and the distal end; and wherein the tubular member comprises a first aperture at the proximal end and a second aperture at the distal end, wherein the inner bore is operable to receive an implant at the first aperture and deliver the implant therethrough at the second aperture, and wherein the inner bore has a substantially uniform cross-sectional width over the predetermined length.

Statement 65: The apparatus according to Statement 64, wherein the base radially extends from at least a portion of the proximal end of the tubular member.

Statement 66: The apparatus according to Statement 64 or Statement 65, wherein the inner bore has a longitudinal axis therethrough, the tubular member extending along the longitudinal axis.

Statement 67: The apparatus according to any one of the preceding Statements 64-66, wherein the inner bore extends longitudinally along a longitudinal axis a predetermined length away from the lower surface of the base.

Statement 68: The apparatus according to Statement 66 or Statement 67, wherein the longitudinal axis extends substantially perpendicular to the base.

Statement 69: The apparatus according to any one of the preceding Statements 64-68, wherein the tubular member extends longitudinally along a longitudinal axis substantially perpendicular to the base.

Statement 70: The apparatus according to any one of the preceding Statements 64-69, wherein the tubular member extends substantially orthogonally from the base.

Statement 71: The apparatus according to any one of the preceding Statements 64-70, wherein the base extends away from the tubular member in a direction substantially perpendicular to the longitudinal axis.

Statement 72: The apparatus according to any one of the preceding Statements 64-71, wherein the tubular member is substantially cylindrical in cross-sectional shape.

Statement 73: The apparatus according to any one of the preceding Statements 64-71, wherein the tubular member is elliptical in cross-sectional shape.

Statement 74: The apparatus according to any one of the preceding Statements 64-73, wherein at least a portion of the inner bore of tubular member extends a second predetermined length above the upper surface of the base.

Statement 75: The apparatus according to any one of the preceding Statements 64-74, wherein the lower surface of the base is operable to engage with a skin of the subject.

Statement 76: The apparatus according to any one of the preceding Statements 64-75, wherein the lower surface of the base is operable to engage a skin of the subject adjacent to an incision, wherein the inner bore of tubular member substantially overlies at least a portion of the incision.

Statement 77: The apparatus according to any one of the preceding Statements 64-76, wherein the lower surface of the base is operable to engage with a skin of the subject so as to resist movement of the base with respect to the skin when engaged with the skin.

Statement 78: The apparatus according to any one of the preceding Statements 64-77, wherein the lower surface is operable to frictionally engage the skin of a subject, wherein the frictional engagement resists movement of the base relative to the skin.

Statement 79: The apparatus according to any one of the preceding Statements 64-78, wherein the lower surface comprises a textured surface.

Statement 80: The apparatus according to any one of the preceding Statements 64-79, wherein the lower surface comprises a surface operable to frictionally engage the skin of a subject once wetted.

Statement 81: The apparatus according to any one of the preceding Statements 64-79, wherein a fluid is disposed on one of the lower surface and/or the skin of the patient, the fluid operable to form a frictional engagement between the lower surface and the skin.

Statement 82: The apparatus according to any one of the preceding Statements 64-79, wherein an adhesive is disposed on the lower surface.

Statement 83: The apparatus according to Statement 82, wherein the lower surface further comprises a removable backing, the removable backing operable to expose the adhesive.

Statement 84: The apparatus according to any one of the preceding Statements 64-83, wherein the predetermined length is determined based on a distance between an incision in the skin of a patient and a surgically-created implant pocket formed below the skin.

Statement 85: The apparatus according to any one of the preceding Statements 64-84, wherein the predetermined length between the proximal end and the distal end extends the inner bore operably to deliver an implant subdermally through the first aperture, inner bore, and second aperture into the surgically-created implant pocket when the lower surface of base is adjacently engaged with the skin of a patient and the distal end is received into at least a portion of the implant pocket.

Statement 86: The apparatus according to any one of the preceding Statements 64-85, wherein the proximal end of tubular member is operable to receive an implant therethrough.

Statement 87: The apparatus according to Statement 86, wherein the tubular member is further operable to deliver the implant subdermally to the implant pocket through the predetermined length of inner bore of the tubular member.

Statement 88: The apparatus according to any one of the preceding Statements 64-87, wherein the distal end of tubular member is operable to be inserted into an incision in the skin of the subject, and the tubular member is operable to be extended the predetermined length such that the distal end is received into at least a portion of the surgically-created implant pocket.

Statement 89: The apparatus according to Statement 88, wherein tubular member extends along at least a portion of a dissection tunnel formed between the incision and the implant pocket.

Statement 90: The apparatus according to Statement 88 or Statement 89, wherein the tubular member is operable to deliver the implant to the implant pocket through a dissection tunnel connecting the incision to the implant pocket without the implant contacting the dissection tunnel.

Statement 91: The apparatus according to any one of the preceding Statements 64-90, wherein the tubular member comprises an inner surface and an outer surface, the inner surface defining the inner bore of tubular member.

Statement 92: The apparatus according to any one of the preceding Statements 64-91, wherein the tubular member and the base are formed from the same material.

Statement 93: The apparatus according to any one of the preceding Statements 64-92, wherein the tubular member and base are formed from a flexible material.

Statement 94: The apparatus according to Statement 93, wherein the flexible material is resistant to stretching.

Statement 95: The apparatus according to Statement 93, wherein the flexible material is capable of stretching.

Statement 96: The apparatus according to Statement 93, wherein the flexible material is operable to stretch when an implant is inserted and/or physically manipulated through the longitudinal length of the inner bore of the tubular member.

Statement 97: The apparatus according to any one of the preceding Statements 93-96, wherein the flexible material is selected from the group consisting of plastic-containing fabrics, polymers, plastics, mylar, vinyls, polyvinyl chloride, ethylene and alpha-olefin copolymers, silicone, solid silicone, silicone rubber, and any combination thereof.

Statement 98: The apparatus according to any one of the preceding Statements 64-97, wherein the tubular member and the base are integrally formed.

Statement 99: The apparatus according to any one of the preceding Statements 64-98, wherein the inner bore of tubular member is not tapered along the predetermined length.

Statement 100: The apparatus according to any one of the preceding Statements 64-99, wherein the inner bore comprises a lubricant.

Statement 101: The apparatus according to any one of the preceding Statements 64-99, wherein the inner surface of the tubular member comprises a lubricant.

Statement 102: The apparatus according to any one of the preceding Statements 64-99, wherein the outer surface of the tubular member comprises a lubricant.

Statement 103: The apparatus according to any one of the preceding Statements 100-102, wherein the lubricant is a sterile lubricant selected from the group consisting of a surgical lubricant, a water-based lubricating jelly, a dry lubricant, a powdered lubricant, a moisture-activated lubricant, and any combination thereof.

Statement 104: The apparatus according to any one of the preceding Statements 64-103, wherein the inner bore comprises a lubricating coating or a friction-reducing coating.

Statement 105: The apparatus according to any one of the preceding Statements 64-103, wherein the inner surface of the tubular member comprises a lubricating coating or a friction-reducing coating.

Statement 106: The apparatus according to any one of the preceding Statements 64-103, wherein the outer surface of the tubular member comprises a lubricating coating or a friction-reducing coating.

Statement 107: The apparatus according to any one of the preceding Statements 64-106, wherein the predetermined length of the inner bore is equal to or less than a measured length of the dissection tunnel.

Statement 108: The apparatus according to any one of the preceding Statements 64-106, wherein the predetermined length of the inner bore is equal to or less than a measured length of the upper dissection tunnel.

Statement 109: The apparatus according to any one of the preceding Statements 64-108, wherein the predetermined length of the inner bore is greater than 1 cm.

Statement 110: The apparatus according to any one of the preceding Statements 64-108, wherein the predetermined length of the inner bore is greater than 1.5 cm.

Statement 111: The apparatus according to any one of the preceding Statements 64-108, wherein the predetermined length of the inner bore is greater than 2 cm.

Statement 112: The apparatus according to any one of the preceding Statements 64-108, wherein the predetermined length of the inner bore is greater than 2.5 cm.

Statement 113: The apparatus according to any one of the preceding Statements 64-108, wherein the predetermined length of the inner bore is greater than 3 cm.

Statement 114: The apparatus according to any one of the preceding Statements 64-108, wherein the predetermined length of the inner bore is greater than 3.5 cm.

Statement 115: The apparatus according to any one of the preceding Statements 64-108, wherein the predetermined length of the inner bore is greater than 4 cm.

Statement 116: The apparatus according to any one of the preceding Statements 64-108, wherein the predetermined length of the inner bore is greater than 4.5 cm.

Statement 117: The apparatus according to any one of the preceding Statements 64-108, wherein the predetermined length of the inner bore is greater than 5 cm.

Statement 118: The apparatus according to any one of the preceding Statements 64-108, wherein the predetermined length of the inner bore is from about 1.5 cm to about 10 cm.

Statement 119: The apparatus according to any one of the preceding Statements 64-108, wherein the predetermined length of the inner bore is from about 1.5 cm to about 5 cm.

Statement 120: The apparatus according to any one of the preceding Statements 64-108, wherein the predetermined length of the inner bore is from about 3 cm to about 8 cm.

Statement 121: The apparatus according to any one of the preceding Statements 64-120, wherein the second aperture that is substantially aligned with the first aperture when the tubular member is fully extended.

Statement 122: The apparatus according to any one of the preceding Statements 64-121, wherein the distal end has substantially the same cross-sectional width as the cross-sectional width of the proximal end.

Statement 123: The apparatus according to any one of the preceding Statements 64-122, wherein the cross-sectional width of the inner bore at the distal end of the tubular member is substantially the same as the cross-sectional width of the inner bore at the proximal end of the tubular member.

Statement 124: The apparatus according to any one of the preceding Statements 64-123, wherein the second aperture has substantially the same cross-sectional width as the first aperture.

Statement 125: The apparatus according to any one of the preceding Statements 64-124, wherein the distal end and the proximal end of the inner bore have the same cross-sectional profile, wherein the cross-sectional profile is selected from the group consisting of circular, elliptical, and oval.

Statement 126: The apparatus according to any one of the preceding Statements 64-124, wherein the distal end and the proximal end of the inner bore have a different cross-sectional profile, wherein the cross-sectional profile is selected from the group consisting of circular, elliptical, and oval.

Statement 127: The apparatus according to Statement 126, wherein the distal end and the proximal end of the inner bore have substantially the same cross-sectional width.

Statement 128: The apparatus according to any one of the preceding Statements 64-124, wherein the first aperture and the second aperture have the same cross-sectional profile, wherein the cross-sectional profile is selected from the group consisting of circular, elliptical, and oval.

Statement 129: The apparatus according to any one of the preceding Statements 64-124, wherein the first aperture and the second aperture have a different cross-sectional profile, wherein the cross-sectional profile is selected from the group consisting of circular, elliptical, and oval.

Statement 130: The apparatus according to Statement 129, wherein the first aperture and the second aperture have substantially the same cross-sectional width.

Statement 131: A system comprising: an apparatus for inserting an implant into a surgically-created implant pocket in a subject according to any one of the preceding Statements 1-130, 245-274, and 283; and an implant.

Statement 132: A system comprising: an apparatus for inserting an implant into a surgically-created implant pocket in a subject according to any one of Statements 1-130, 245-274, and 283; and a conical sleeve having a an interior cavity, a first terminus, and a second terminus, wherein the first terminus has a larger diameter than the second terminus; wherein the second terminus is operable to be inserted into the aperture or inner bore of the tubular member of the apparatus, the conical sleeve further operable to receive an implant into its interior cavity via the first terminus and deliver the implant through the second terminus into the inner bore of the apparatus.

Statement 133: The system according to Statement 132, further comprising an implant.

Statement 134: A kit comprising: an apparatus for inserting an implant into a surgically-created implant pocket in a subject according to any one of Statements 1-130, 245-274, and 283; and an implant; wherein the apparatus and the implant are packaged together.

Statement 135: A kit comprising: an apparatus for inserting an implant into a surgically-created implant pocket in a subject according to any one of Statements 1-130, 245-274, and 283; and a conical sleeve having a an interior cavity, a first terminus, and a second terminus, wherein the first terminus has a larger diameter than the second terminus; wherein the second terminus is operable to be inserted into the aperture or inner bore of the tubular member of the apparatus, the conical sleeve further operable to receive an implant into its interior cavity via the first terminus and deliver the implant through the second terminus into the inner bore of the apparatus; wherein the apparatus and the implant are packaged together.

Statement 136: The kit according to Statement 135, further comprising an implant.

Statement 137: The apparatus according to any one of Statements 1-130, 245-274, and 283, wherein the implant is selected from the group consisting of a filled implant or a pre-filled implant, an unfilled implant, a saline implant, a silicone gel implant, a textured implant, a smooth implant, a highly cohesive silicone gel implant, an oil-filled implant, a pacemaker, a joint replacement prosthesis, an allograft, an autograft, and a prosthesis implant.

Statement 138: The system according to any one of the preceding Statements 131-133, wherein the implant is selected from the group consisting of a filled implant or a pre-filled implant, an unfilled implant, a saline implant, a silicone gel implant, a textured implant, a smooth implant, a highly cohesive silicone gel implant, an oil-filled implant, a pacemaker, a joint replacement prosthesis, an allograft, an autograft, and a prosthesis implant.

Statement 139: The kit according to any one of the preceding Statements 134-136, wherein the implant is selected from the group consisting of a filled implant or a pre-filled implant, an unfilled implant, a saline implant, a silicone gel implant, a textured implant, a smooth implant, a highly cohesive silicone gel implant, an oil-filled implant, a pacemaker, a joint replacement prosthesis, an allograft, an autograft, and a prosthesis implant.

Statement 140: A method for inserting an implant into a surgically-created implant pocket in a subject through a dissection tunnel connecting the implant pocket to an incision on the skin of the subject, the method comprising: providing a sterile biofilm protection implant shield, the implant shield comprising: a base having an upper surface and a lower surface, the base further having an aperture formed therein and extending through the upper surface and the lower surface; and a tubular member coupled with the base, the tubular member having an inner bore extending longitudinally between a proximal end and a distal end, the inner bore extending a predetermined length away from the lower surface of the base; wherein the proximal end of the tubular member is coupled with the base and the inner bore is substantially aligned with the aperture formed in the base; and wherein the inner bore is operable to receive the implant therethrough and has a substantially uniform cross-sectional width over the predetermined length; inserting the distal end of the tubular member of the implant shield through the incision in the skin of subject and into the dissection tunnel such that the distal end of the tubular member is received in at least a portion of the dissection tunnel or the implant pocket; causing the lower surface of the base to substantially engage with at least a portion of the skin adjacent to an incision leading to the implant pocket; and delivering the implant to the implant pocket by inserting the implant through the aperture of the base and through the inner bore and distal end of the tubular member to the implant pocket.

Statement 141: The method according to Statement 140, further comprising: opening the dissection tunnel using one or more retractors during inserting the tubular member of the implant shield into the implant pocket or a portion of a dissection tunnel.

Statement 142: The method according to Statement 140 or Statement 141, wherein inserting the tubular member of the implant shield into the implant pocket or a portion of a dissection tunnel connecting the implant pocket to an incision on a skin of the subject comprises inserting the tubular member or a distal end thereof using forceps or a similar device.

Statement 143: The method according to any one of the preceding Statements 140-142, further comprising: causing the lower surface of the base to engage the skin of the subject so as to resist movement of the base with respect to the skin when engaged with the skin.

Statement 144: The method according to Statement 143, wherein the base is frictionally engaged with the skin of the subject.

Statement 145: The method according to Statement 143 or Statement 144, further comprising wetting the lower surface of the base to cause the engagement with the skin of the subject.

Statement 146: The method according to Statement 143, wherein the base is engaged with the skin of the subject by an adhesive disposed on the lower surface of the base.

Statement 147: The method according to Statement 146, further comprising: exposing the adhesive disposed on the lower surface of the base by removing a removable backing disposed on the lower surface of the base.

Statement 148: The method according to any one of the preceding Statements 140-148, further comprising: attaching the lower surface of the base to the skin of the subject so as to arrest movement of the base with respect to the skin during use.

Statement 149: The method according to any one of the preceding Statements 143-148, wherein the aperture substantially overlies at least a portion of the incision.

Statement 150: The method according to any one of the preceding Statements 140-149, further comprising: inserting the tubular member of the implant shield into the implant pocket or a portion of a dissection tunnel connecting the implant pocket to an incision on a skin of the subject, such that the lower surface of the base substantially engages with at least a portion of the skin adjacent to the incision; and extending the tubular member of the implant shield through the full length of the dissection tunnel such that the distal end extends at least partially into the implant pocket.

Statement 151: The method according to Statement 150, wherein the tubular member of the implant shield is extended through the dissection tunnel using one or more retractors inserted through the aperture and into the inner bore of the tubular member.

Statement 152: The method according to Statement 150, wherein the tubular member of the implant shield is extended through the dissection tunnel using one or more retractors placed outside the aperture and between the tubular member and a tissue forming the dissection tunnel.

Statement 153: The method according to any one of the preceding Statements 150-152, wherein prior to delivering the implant to the implant pocket, the method further comprises: inserting one or more retractors through the aperture and into the inner bore of the tubular member so as to open the inner bore and dissection tunnel for implant insertion.

Statement 154: The method according to any one of the preceding Statements 140-153, wherein the implant is delivered to the implant pocket such that the entire tissue path between an incision on the subject's skin and the implant pocket is shielded from the tissue forming a dissection tunnel connecting the incision to the implant pocket.

Statement 155: The method according to any one of the preceding Statements 140-154, wherein the implant does not contact the tissue forming the dissection tunnel during delivery to the implant pocket.

Statement 156: The method according to any one of the preceding Statements 140-154, wherein the implant shield substantially minimizes the contact of the implant with the tissue forming the dissection tunnel.

Statement 157: The method according to any one of the preceding Statements 140-156, wherein the inner bore of the tubular member forms a sterile path by which the implant may be inserted and delivered to the implant pocket.

Statement 158: The method according to any one of the preceding Statements 140-157, wherein the inner bore of the tubular member forms a sterile path, through which the implant may be delivered, from an incision in a skin of the patient to the implant pocket through a dissection tunnel connecting the incision to the implant pocket.

Statement 159: The method according to any one of the preceding Statements 140-158, further comprising: causing the lower surface of the base to disengage from the skin of subject; and removing the tubular member and implant shield from the subject.

Statement 160: The method according to any one of the preceding Statements 140-159, further comprising: closing the incision.

Statement 161: The method according to any one of the preceding Statements 140-160, further comprising: selecting a biofilm protection implant shield having an inner bore with a cross-sectional width great than the diameter of the implant.

Statement 162: The method according to any one of the preceding Statements 140-161, further comprising: sterilizing the biofilm protection implant shield.

Statement 163: The method according to any one of the preceding Statements 140-162, further comprising: selecting a biofilm protection implant shield having a predetermined length of the inner bore of the tubular member sufficiently long that the tubular member is operable to shield the implant from the upper dissection tunnel and/or a substantial length of the dissection tunnel upon insertion of the implant into the inner bore of the tubular member and transit of the implant to the implant pocket in a subject.

Statement 164: The method according to Statement 163, wherein the substantial length of the dissection tunnel corresponds to at least the entire portion of the dissection tunnel that comprises breast tissue.

Statement 165: The method according to any one of the preceding Statements 140-162, further comprising: selecting a biofilm protection implant shield having a predetermined length of the inner bore of the tubular member equal to or less than a length of a dissection tunnel connecting the implant pocket to an incision on a skin of the subject.

Statement 166: The method according to any one of the preceding Statements 140-162, further comprising: selecting a biofilm protection implant shield having a predetermined length of the inner bore of the tubular member equal to or greater than a length of a dissection tunnel connecting the implant pocket to an incision on a skin of the subject.

Statement 167: The method according to any one of the preceding Statements 140-162, further comprising: measuring a length of a dissection tunnel and/or upper dissection tunnel connecting the implant pocket to an incision on a skin of the subject; and adjusting the predetermined length of the inner bore of the tubular member such that it has a length equal to or less than the length of the dissection tunnel or upper dissection tunnel.

Statement 168: The method according to Statement 167, wherein adjusting the predetermined length comprises cutting the tubular member such that the predetermined length of the inner bore of the tubular member has a length equal to or less than the length of the dissection tunnel or upper dissection tunnel.

Statement 169: The method according to any one of the preceding Statements 140-162, further comprising: measuring a length of a dissection tunnel or upper dissection tunnel connecting the implant pocket to an incision on a skin of the subject; and adjusting the predetermined length of the inner bore of the tubular member such that it has a length equal to or greater than the length of the dissection tunnel or upper dissection tunnel.

Statement 170: The method according to Statement 169, wherein adjusting the predetermined length comprises cutting the tubular member such that the predetermined length of the inner bore of the tubular member has a length equal to or greater than the length of the dissection tunnel or upper dissection tunnel.

Statement 171: The method according to any one of the preceding Statements 140-170, further comprising: creating an incision in the skin of the subject; and surgically-creating an implant pocket and a dissection tunnel connecting the incision to the surgically-created implant pocket.

Statement 172: The method according to any one of the preceding Statements 140-171, wherein delivering the implant to the implant pocket comprises: providing a conical sleeve having a an interior cavity, a first terminus, and a second terminus, wherein the first terminus has a larger diameter than the second terminus; placing the implant into the interior cavity of the conical sleeve; inserting the second terminus through the aperture of the base and into the inner bore of the tubular member such that the terminus of the conical sleeve is received in the implant shield proximal to the implant pocket; and applying pressure to the conical sleeve such that the implant exits the second terminus of the conical sleeve and is delivered to the implant pocket.

Statement 173: The method according to Statement 172, wherein the conical sleeve is a tapered sleeve.

Statement 174: The method according to any one of the preceding Statements 140-173, wherein the subject is a mammal.

Statement 175: The method according to any one of the preceding Statements 140-173, wherein the subject is a human.

Statement 176: The method according to any one of the preceding Statements 140-175, wherein the implant is selected from the group consisting of a breast implant, a pre-filled implant, a pre-filled saline breast implant, a pre-filled silicone breast implant, an un-filled breast implant, a saline breast implant, a silicone breast implant, a textured breast implant, a smooth breast implant, a highly cohesive silicone gel breast implant, an oil-filled breast implant, and an un-filled saline breast implant.

Statement 177: The method according to any one of the preceding Statements 140-176, wherein the incision is a periareolar incision.

Statement 178: The method according to any one of the preceding Statements 140-176, wherein the incision is an inframammary incision.

Statement 179: The method according to any one of the preceding Statements 140-176, wherein the incision is an axillary incision.

Statement 180: The method according to any one of the preceding Statements 140-176, wherein the incision is a transumbilical incision.

Statement 181: The method according to any one of the preceding Statements 140-176, wherein the incision is a vertical incision.

Statement 182: A method of preventing capsular contracture in a subject resulting from surgical insertion of a breast implant in a surgically created implant pocket through a dissection tunnel connecting the implant pocket to an incision on the skin of the patient, the method comprising: providing a sterile biofilm protection implant shield, the implant shield comprising: a base having an upper surface and a lower surface, the base further having an aperture formed therein and extending through the upper surface and the lower surface; and a tubular member coupled with the base, the tubular member having an inner bore extending longitudinally between a proximal end and a distal end, the inner bore extending a predetermined length away from the lower surface of the base; wherein the proximal end of the tubular member is coupled with the base and the inner bore is substantially aligned with the aperture formed in the base; and wherein the inner bore is operable to receive the implant therethrough and has a substantially uniform cross-sectional width over the predetermined length; inserting the distal end of the tubular member of the implant shield through the incision in the skin of subject and into the dissection tunnel such that the distal end of the tubular member is received in at least a portion of the dissection tunnel or the implant pocket; causing the lower surface of the base to substantially engage with at least a portion of the skin adjacent to an incision leading to the implant pocket; and delivering the implant to the implant pocket by inserting the implant through the aperture of the base and through the inner bore and distal end of the tubular member to the implant pocket.

Statement 183: The method according to Statement 182, further comprising: opening the dissection tunnel using one or more retractors during inserting the tubular member of the implant shield into the implant pocket or a portion of a dissection tunnel.

Statement 184: The method according to Statement 182, wherein inserting the tubular member of the implant shield into the implant pocket or a portion of a dissection tunnel connecting the implant pocket to an incision on a skin of the subject comprises inserting the tubular member or a distal end thereof using forceps or a similar device.

Statement 185: The method according to Statement 182, further comprising: causing the lower surface of the base to engage the skin of the subject so as to resist movement of the base with respect to the skin when engaged with the skin.

Statement 186: The method according to Statement 185, wherein the base is frictionally engaged with the skin of the subject.

Statement 187: The method according to Statement 185, wherein the base is engaged with the skin of the subject by an adhesive disposed on the lower surface of the base.

Statement 188: The method according to Statement 187, further comprising: exposing the adhesive disposed on the lower surface of the base by removing a removable backing disposed on the lower surface of the base.

Statement 189: The method according to any one of the preceding Statements 182-188, further comprising: attaching the lower surface of the base to the skin of the subject so as to arrest movement of the base with respect to the skin during use.

Statement 190: The method according to any one of the preceding Statements 182-189, wherein the aperture substantially overlies at least a portion of the incision.

Statement 191: The method according to any one of the preceding Statements 182-190, further comprising: inserting the tubular member of the implant shield into the implant pocket or a portion of a dissection tunnel connecting the implant pocket to an incision on a skin of the subject, such that the lower surface of the base substantially engages with at least a portion of the skin adjacent to the incision; and extending the tubular member of the implant shield through the full length of the dissection tunnel such that the distal end extends at least partially into the implant pocket.

Statement 192: The method according to Statement 191, wherein the tubular member of the implant shield is extended through the dissection tunnel using one or more retractors inserted through the aperture and into the inner bore of the tubular member.

Statement 193: The method according to Statement 191, wherein the tubular member of the implant shield is extended through the dissection tunnel using one or more retractors placed outside the aperture and between the tubular member and a tissue forming the dissection tunnel.

Statement 194: The method according to any one of the preceding Statements 191-193, wherein prior to delivering the implant to the implant pocket, the method further comprises: inserting one or more retractors through the aperture and into the inner bore of the tubular member so as to open the inner bore and dissection tunnel for implant insertion.

Statement 195: The method according to any one of the preceding Statements 182-194, wherein the implant is delivered to the implant pocket such that the entire tissue path between an incision on the subject's skin and the implant pocket is shielded from the tissue forming a dissection tunnel connecting the incision to the implant pocket.

Statement 196: The method according to any one of the preceding Statements 182-195, wherein the implant does not contact the tissue forming the dissection tunnel during delivery to the implant pocket.

Statement 197: The method according to any one of the preceding Statements 182-195, wherein the implant shield substantially minimizes the contact of the implant with the tissue forming the dissection tunnel.

Statement 198: The method according to any one of the preceding Statements 182-197, wherein the inner bore of the tubular member forms a sterile path by which the implant may be inserted and delivered to the implant pocket.

Statement 199: The method according to any one of the preceding Statements 182-198, wherein the inner bore of the tubular member forms a sterile path, through which the implant may be delivered, from an incision in a skin of the patient to the implant pocket through a dissection tunnel connecting the incision to the implant pocket.

Statement 200: The method according to any one of the preceding Statements 182-199, further comprising: causing the lower surface of the base to disengage from the skin of subject; and removing the tubular member and implant shield from the subject.

Statement 201: The method according to any one of the preceding Statements 182-200, further comprising: closing the incision.

Statement 202: The method according to any one of the preceding Statements 182-201, further comprising: selecting a biofilm protection implant shield having an inner bore with a cross-sectional width great than the diameter of the implant.

Statement 203: The method according to any one of the preceding Statements 182-202, further comprising: sterilizing the biofilm protection implant shield.

Statement 204: The method according to any one of the preceding Statements 182-202, further comprising: selecting a biofilm protection implant shield having a predetermined length of the inner bore of the tubular member sufficiently long that the tubular member is operable to shield the implant from the upper dissection tunnel and/or a substantial length of the dissection tunnel upon insertion of the implant into the inner bore of the tubular member and transit of the implant to the implant pocket in a subject.

Statement 205: The method according to Statement 204, wherein the substantial length of the dissection tunnel corresponds to at least the entire portion of the dissection tunnel that comprises breast tissue.

Statement 206: The method according to any one of the preceding Statements 182-203, further comprising: selecting a biofilm protection implant shield having a predetermined length of the inner bore of the tubular member equal to or less than a length of a dissection tunnel or an upper dissection tunnel connecting the implant pocket to an incision on a skin of the subject.

Statement 207: The method according to any one of the preceding Statements 182-203, further comprising: selecting a biofilm protection implant shield having a predetermined length of the inner bore of the tubular member equal to or greater than a length of a dissection tunnel or an upper dissection tunnel connecting the implant pocket to an incision on a skin of the subject.

Statement 208: The method according to any one of the preceding Statements 182-203, further comprising: measuring a length of a dissection tunnel or upper dissection tunnel connecting the implant pocket to an incision on a skin of the subject; and adjusting the predetermined length of the inner bore of the tubular member such that it has a length equal to or less than the length of the dissection tunnel or upper dissection tunnel.

Statement 209: The method according to Statement 208, wherein adjusting the predetermined length comprises cutting the tubular member such that the predetermined length of the inner bore of the tubular member has a length equal to or less than the length of the dissection tunnel or upper dissection tunnel.

Statement 210: The method according to any one of the preceding Statements 182-203, further comprising: measuring a length of a dissection tunnel or upper dissection tunnel connecting the implant pocket to an incision on a skin of the subject; and adjusting the predetermined length of the inner bore of the tubular member such that it has a length equal to or greater than the length of the dissection tunnel or upper dissection tunnel.

Statement 211: The method according to Statement 210, wherein adjusting the predetermined length comprises cutting the tubular member such that the predetermined length of the inner bore of the tubular member has a length equal to or greater than the length of the dissection tunnel or upper dissection tunnel.

Statement 212: The method according to any one of the preceding Statements 182-211, further comprising: creating an incision in the skin of the subject; and surgically-creating an implant pocket and a dissection tunnel connecting the incision to the surgically-created implant pocket.

Statement 213: The method according to any one of the preceding Statements 182-212, wherein delivering the implant to the implant pocket comprises: providing a conical sleeve having a an interior cavity, a first terminus, and a second terminus, wherein the first terminus has a larger diameter than the second terminus; placing the implant into the interior cavity of the conical sleeve; inserting the second terminus through the aperture of the base and into the inner bore of the tubular member such that the terminus of the conical sleeve is received in the implant shield proximal to the implant pocket; and applying pressure to the conical sleeve such that the implant exits the second terminus of the conical sleeve and is delivered to the implant pocket.

Statement 214: The method according to Statement 213, wherein the conical sleeve is a tapered sleeve.

Statement 215: The method according to any one of the preceding Statements 182-214, wherein the subject is a mammal.

Statement 216: The method according to any one of the preceding Statements 182-214, wherein the subject is a human.

Statement 217: The method according to any one of the preceding Statements 182-216, wherein the implant is selected from the group consisting of a breast implant, a pre-filled breast implant, a pre-filled saline breast implant, a pre-filled silicone breast implant, an un-filled breast implant, a saline breast implant, a silicone breast implant, a textured breast implant, a smooth breast implant, a highly cohesive silicone gel breast implant, an oil-filled breast implant, and an un-filled saline breast implant.

Statement 218: The method according to any one of the preceding Statements 182-217, wherein the incision is a periareolar incision.

Statement 219: The method according to any one of the preceding Statements 182-217, wherein the incision is an inframammary incision.

Statement 220: The method according to any one of the preceding Statements 182-217, wherein the incision is an axillary incision.

Statement 221: The method according to any one of the preceding Statements 182-217, wherein the incision is a transumbilical incision.

Statement 222: The method according to any one of the preceding Statements 182-217, wherein the incision is a vertical incision.

Statement 223: The method according to any one of the preceding Statements 140-222, wherein the implant is selected from the group consisting of a filled implant or a pre-filled implant, an unfilled implant, a saline implant, a silicone gel implant, a textured implant, a smooth implant, a highly cohesive silicone gel implant, an oil-filled implant, a pacemaker, a joint replacement prosthesis, an allograft, an autograft, and a prosthesis implant.

Statement 224: The method according to any one of the preceding Statements 140-223, wherein the implant is an unfilled implant and the implant has a cross-sectional width smaller than the cross-sectional width of the tubular member of the implant shield.

Statement 225: The method according to any one of the preceding Statements 140-223, wherein the implant has a cross-sectional width smaller than the cross-sectional width of the tubular member of the implant shield due to the deformation forces during insertion of the implant into the aperture and inner bore of the implant shield.

Statement 226: The method according to any one of the preceding Statements 140-225, wherein the distal end of the tubular member is inserted greater than 1.5 cm below the incision.

Statement 227: The method according to any one of the preceding Statements 140-225, wherein the distal end of the tubular member is inserted greater than 2 cm below the incision.

Statement 228: The method according to any one of the preceding Statements 140-225, wherein the distal end of the tubular member is inserted greater than 2.5 cm below the incision.

Statement 229: The method according to any one of the preceding Statements 140-225, wherein the distal end of the tubular member is inserted greater than 3 cm below the incision.

Statement 230: The method according to any one of the preceding Statements 140-225, wherein the distal end of the tubular member is inserted greater than 3.5 cm below the incision.

Statement 231: The method according to any one of the preceding Statements 140-225, wherein the distal end of the tubular member is inserted greater than 4.5 cm below the incision.

Statement 232: The method according to any one of the preceding Statements 140-225, wherein the distal end of the tubular member is inserted greater than 5 cm below the incision.

Statement 233: The method according to any one of the preceding Statements 140-225, wherein the distal end of the tubular member is inserted into the dissection tunnel to a depth of from about 2 cm to about 10 cm below the incision.

Statement 234: The method according to any one of the preceding Statements 140-225, wherein the distal end of the tubular member is inserted into the dissection tunnel to a depth of from about 2 cm to about 5 cm below the incision.

Statement 235: The method according to any one of the preceding Statements 140-225, wherein the distal end of the tubular member is inserted into the dissection tunnel to a depth of from about 3 cm to about 8 cm below the incision.

Statement 236: The method according to any one of the preceding Statements 140-225, wherein the distal end of the tubular member is inserted such that at least 1.5 cm of the length of the dissection tunnel is shielded from the implant during insertion of the implant into the implant pocket.

Statement 237: The method according to any one of the preceding Statements 140-225, wherein the distal end of the tubular member is inserted such that at least 2 cm of the length of the dissection tunnel is shielded from the implant during insertion of the implant into the implant pocket.

Statement 238: The method according to any one of the preceding Statements 140-225, wherein the distal end of the tubular member is inserted such that at least 2.5 cm of the length of the dissection tunnel is shielded from the implant during insertion of the implant into the implant pocket.

Statement 239: The method according to any one of the preceding Statements 140-225, wherein the distal end of the tubular member is inserted such that at least 3 cm of the length of the dissection tunnel is shielded from the implant during insertion of the implant into the implant pocket.

Statement 240: The method according to any one of the preceding Statements 140-225, wherein the distal end of the tubular member is inserted such that at least 3.5 cm of the length of the dissection tunnel is shielded from the implant during insertion of the implant into the implant pocket.

Statement 241: The method according to any one of the preceding Statements 140-225, wherein the distal end of the tubular member is inserted such that at least 4 cm of the length of the dissection tunnel is shielded from the implant during insertion of the implant into the implant pocket.

Statement 242: The method according to any one of the preceding Statements 140-225, wherein the distal end of the tubular member is inserted such that at least 4.5 cm of the length of the dissection tunnel is shielded from the implant during insertion of the implant into the implant pocket.

Statement 243: The method according to any one of the preceding Statements 140-225, wherein the distal end of the tubular member is inserted such that at least 5 cm of the length of the dissection tunnel is shielded from the implant during insertion of the implant into the implant pocket.

Statement 244: The method according to any one of the preceding Statements 140-225, wherein the distal end of the tubular member is inserted into the dissection tunnel such that the entire upper dissection tunnel is shielded from the implant during insertion of the implant into the implant pocket.

Statement 245: The apparatus according to any one of the preceding Statements 1-130, wherein the base extends away from the tubular member in substantially the same plane as the aperture of the base.

Statement 246: The apparatus according to any one of the preceding Statements 1-130 and 245, wherein the cross-sectional width of the inner bore of the tubular member is from about 3 cm to about 12 cm.

Statement 247: The apparatus according to any one of the preceding Statements 1-130 and 245, wherein the cross-sectional width of the inner bore of the tubular member is from about 5 cm to about 8 cm.

Statement 248: The apparatus according to any one of the preceding Statements 1-130 and 245, wherein the cross-sectional width of the inner bore of the tubular member is from about 3.5 cm to about 9 cm.

Statement 249: The apparatus according to any one of the preceding Statements 1-130 and 245-248, wherein the base comprises a diameter that is at least three times greater than the cross-sectional width of the inner bore of the tubular member.

Statement 250: The apparatus according to any one of the preceding Statements 1-130 and 245-248, wherein the base comprises a diameter that is at least three times greater than the cross-sectional width of the aperture of the base.

Statement 251: The apparatus according to any one of the preceding Statements 1-130 and 245-248, wherein the base comprises a diameter that is at least three times greater than the cross-sectional width of the outer bore of the tubular member.

Statement 252: The apparatus according to any one of the preceding Statements 1-130 and 245-248, wherein the base comprises a diameter that is from about three (3) to five (5) times greater than the cross-sectional width of the inner bore of the tubular member.

Statement 253: The apparatus according to any one of the preceding Statements 1-130 and 245-248, wherein the base comprises a diameter that is from about three (3) to five (5) times greater than the cross-sectional width of the aperture of the base.

Statement 254: The apparatus according to any one of the preceding Statements 1-130 and 245-248, wherein the base comprises a diameter that is from about three (3) to five (5) times greater than the cross-sectional width of the outer bore of the tubular member.

Statement 255: The apparatus according to any one of the preceding Statements 1-130 and 245-248, wherein the base comprises a diameter that is from about 9 cm to about 60 cm.

Statement 256: The apparatus according to any one of the preceding Statements 1-130 and 245-248, wherein the base comprises a diameter that is from about 10.5 cm to about 45 cm.

Statement 257: The apparatus according to any one of the preceding Statements 1-130 and 245-248, wherein the base comprises a diameter that is from about 15 cm to about 40 cm.

Statement 258: The apparatus according to any one of the preceding Statements 1-130 and 245-248, wherein the base comprises a radial length that is greater than or equal to the cross-sectional width of the inner bore of the tubular member.

Statement 259: The apparatus according to any one of the preceding Statements 1-130 and 245-248, wherein the base comprises a radial length that is greater than or equal to the cross-sectional width of the aperture of the base.

Statement 260: The apparatus according to any one of the preceding Statements 1-130 and 245-248, wherein the base comprises a radial length that is greater than or equal to the cross-sectional width of the outer bore of the tubular member.

Statement 261: The apparatus according to any one of the preceding Statements 1-130 and 245-248, wherein the base comprises a radial length that from about one (1) to about two (2) times cross-sectional width of the inner bore of the tubular member.

Statement 262: The apparatus according to any one of the preceding Statements 1-130 and 245-248, wherein the base comprises a radial length that from about one (1) to about two (2) times the cross-sectional width of the aperture of the base.

Statement 263: The apparatus according to any one of the preceding Statements 1-130 and 245-248, wherein the base comprises a radial length that from about one (1) to about two (2) times the cross-sectional width of the outer bore of the tubular member.

Statement 264: The apparatus according to any one of the preceding Statements 1-130 and 245-248, wherein the base comprises a radial length from about 3 cm to about 12 cm.

Statement 265: The apparatus according to any one of the preceding Statements 1-130 and 245-248, wherein the base comprises a radial length from about 3 cm to about 18 cm.

Statement 266: The apparatus according to any one of the preceding Statements 1-130 and 245-248, wherein the base comprises a radial length from about 5 cm to about 8 cm.

Statement 267: The apparatus according to any one of the preceding Statements 1-130 and 245-248, wherein the base comprises a radial length from about 10 cm to about 16 cm.

Statement 268: The apparatus according to any one of the preceding Statements 1-130 and 245-248, wherein the base comprises a radial length from about 5 cm to about 16 cm.

Statement 269: The apparatus according to any one of the preceding Statements 1-130 and 245-268, wherein the tubular member is stretchable.

Statement 270: The apparatus according to any one of the preceding Statements 1-130 and 245-268, wherein the tubular member comprises a stretchable material.

Statement 271: The apparatus according to any one of the preceding Statements 1-130 and 245-268, wherein the tubular member is elastic.

Statement 272: The apparatus according to any one of the preceding Statements 1-130 and 245-268, wherein the tubular member comprises an elastic material.

Statement 273: The apparatus according to any one of the preceding Statements 1-130 and 245-268, wherein the tubular member is extensible.

Statement 274: The apparatus according to any one of the preceding Statements 1-130 and 245-268, wherein the tubular member comprises an extensible material.

Statement 275: The method according to any one of the preceding Statements 140-244, wherein the tubular member is operable to stretch during insertion of the implant into the inner bore of the tubular member.

Statement 276: The method according to any one of the preceding Statements 140-244, wherein the tubular member is stretchable.

Statement 277: The method according to any one of the preceding Statements 140-244, wherein the tubular member comprises a stretchable material.

Statement 278: The method according to any one of the preceding Statements 140-244, wherein the tubular member is elastic.

Statement 279: The method according to any one of the preceding Statements 140-244, wherein the tubular member comprises an elastic material.

Statement 280: The method according to any one of the preceding Statements 140-244, wherein the tubular member is extensible.

Statement 281: The method according to any one of the preceding Statements 140-244, wherein the tubular member comprises an extensible material.

Statement 282: The method according to any one of the preceding Statements 140-244 and 275-281, wherein the aperture of the base has a cross-sectional width that is substantially the same as the cross-sectional width of the inner bore of the tubular member.

Statement 283: The apparatus according to any one of the preceding Statements 1-130 and 245-274, wherein the aperture of the base has a cross-sectional width that is substantially the same as the cross-sectional width of the inner bore of the tubular member.

What is claimed is:

1. An apparatus for inserting a breast implant into a surgically-created implant pocket in a breast of a subject, the apparatus comprising:
    a base having an upper surface and a lower surface, the base having an aperture formed therein and extending through the upper surface and the lower surface, wherein the aperture is operable to receive the breast implant therethrough; and
    a tubular member coupled with the base, the tubular member having an inner bore extending longitudinally between a proximal end having a proximal opening and a distal end having a distal opening, the inner bore extending a predetermined length away from the lower surface of the base;
    wherein the proximal end of the tubular member is coupled with the lower surface of the base and the distal end of the tubular member extends a predetermined length away from the lower surface of the base;
    wherein the inner bore of the tubular member is substantially aligned with the aperture formed in the base;
    wherein the inner bore is operable to receive the breast implant therethrough and has a substantially uniform cross-sectional width over the predetermined length;
    wherein the upper surface of the base forms the proximal most end of the apparatus and the distal end of the tubular member forms the distal most end of the apparatus; and
    wherein the base comprises a diameter that is at least three times greater than the cross-sectional width of the inner bore of the tubular member.

2. The apparatus according to claim 1, wherein the lower surface of the base is operable to frictionally engage the skin of a subject, wherein the frictional engagement resists movement of the base relative to the skin.

3. The apparatus according to claim 2, wherein the lower surface comprises a surface operable to frictionally engage the skin of a subject once wetted.

4. The apparatus according to claim 1, wherein an adhesive is disposed on the lower surface of the base.

5. The apparatus according to claim 4, wherein the lower surface further comprises a removable backing, the removable backing operable to expose the adhesive.

6. The apparatus according to claim 1, wherein the predetermined length is determined based on a distance between an incision in the skin of a patient and a surgically-created implant pocket formed below the skin.

7. The apparatus according to claim 1, wherein the tubular member comprises an inner surface and an outer surface, the inner surface comprising a lubricant and defining the inner bore of tubular member.

8. The apparatus according to claim 1, wherein the predetermined length is greater than 1 cm.

9. The apparatus according to claim 1, wherein the predetermined length is from about 2 cm to about 10 cm.

10. The apparatus according to claim 1, wherein the base extends away from the tubular member in substantially the same plane as the aperture of the base.

11. The apparatus according to claim 1, wherein the base comprises a diameter that is from about three (3) to five (5) times greater than the cross-sectional width of the inner bore of the tubular member.

12. The apparatus according to claim 1, wherein the tubular member is stretchable.

13. The apparatus according to claim 1, wherein the base and the tubular member are formed from a flexible material, the flexible material selected from the group consisting of plastic-containing fabrics, polymers, plastics, polyethylene terephthalate, vinyls, polyvinyl chloride, ethylene and alpha-olefin copolymers, silicone, solid silicone, silicone rubber, and any combination thereof.

14. The apparatus according to claim 1, wherein the lower surface of the base is operable to removably engage the skin of the subject so as to substantially resist movement of the base relative to the skin of the subject during implant insertion into the aperture and inner bore.

15. An apparatus for shielding an implant from a dissection tunnel in a subject during insertion of the implant into a surgically-created implant pocket connected to an incision in the skin of the subject by the dissection tunnel, the apparatus comprising:
   a base having an upper surface and a lower surface, the base having an aperture formed therein and extending through the upper surface and the lower surface, wherein the aperture is operable to receive the implant therethrough; and
   a tubular member coupled with the base, the tubular member having an inner bore extending longitudinally between a proximal end having a proximal opening and a distal end having a distal opening, the inner bore extending a predetermined length away from the lower surface of the base;
   wherein the proximal end of the tubular member is coupled with the lower surface of the base and the distal end of the tubular member extends a predetermined length away from the lower surface of the base, the distal end of the tubular member operable to be inserted into the dissection tunnel in the subject connecting the incision in the skin of the subject to the surgically-created implant pocket;
   wherein the inner bore of the tubular member is substantially aligned with the aperture formed in the base;
   wherein the inner bore is operable to receive the implant therethrough and has a substantially uniform cross-sectional width over the predetermined length;
   wherein the upper surface of the base forms the proximal most end of the apparatus and the distal end of the tubular member forms the distal most end of the apparatus; and
   wherein the base comprises a diameter that is at least three times greater than the cross-sectional width of the inner bore of the tubular member.

16. The apparatus according to claim 15, wherein the aperture of the base is configured to receive sterile retractors such that the retractors may be used to hold open the tubular member during insertion of the implant.

17. The apparatus according to claim 15, wherein the aperture of the base is configured to receive the terminus of a conical sleeve used to deliver the implant through the aperture of the base.

18. The apparatus according to claim 15, wherein the lower surface of the base is operable to frictionally engage the skin of a subject, wherein the frictional engagement resists movement of the base relative to the skin.

19. The apparatus according to claim 18, wherein the lower surface comprises a surface operable to frictionally engage the skin of a subject once wetted.

20. The apparatus according to claim 15, wherein an adhesive is disposed on the lower surface of the base.

21. The apparatus according to claim 20, wherein the lower surface further comprises a removable backing, the removable backing operable to expose the adhesive.

22. The apparatus according to claim 15, wherein the predetermined length is determined based on a distance between an incision in the skin of a patient and a surgically-created implant pocket formed below the skin.

23. The apparatus according to claim 15, wherein the tubular member comprises an inner surface and an outer surface, the inner surface comprising a lubricant and defining the inner bore of tubular member.

24. The apparatus according to claim 15, wherein the predetermined length is greater than 1 cm.

25. The apparatus according to claim 15, wherein the predetermined length is from about 2 cm to about 10 cm.

26. The apparatus according to claim 15, wherein the base extends away from the tubular member in substantially the same plane as the aperture of the base.

27. The apparatus according to claim 15, wherein the base comprises a diameter that is from about three (3) to five (5) times greater than the cross-sectional width of the inner bore of the tubular member.

28. The apparatus according to claim 15, wherein the tubular member is stretchable.

29. The apparatus according to claim 15, wherein the base and the tubular member are formed from a flexible material, the flexible material selected from the group consisting of plastic-containing fabrics, polymers, plastics, polyethylene terephthalate, vinyls, polyvinyl chloride, ethylene and alpha-olefin copolymers, silicone, solid silicone, silicone rubber, and any combination thereof.

30. The apparatus according to claim 15, wherein the lower surface of the base is operable to removably engage the skin of the subject so as to substantially resist movement of the base relative to the skin of the subject during implant insertion into the aperture and inner bore.

* * * * *